(12) United States Patent
Sparrow et al.

(10) Patent No.: US 8,344,114 B2
(45) Date of Patent: Jan. 1, 2013

(54) ANTAGONISTS OF PCSK9

(75) Inventors: Carl P. Sparrow, Westfield, NJ (US);
Ayesha Sitlani, Metuchen, NJ (US);
Shilpa Pandit, Edison, NJ (US); Jon H.
Condra, Doylestown, PA (US); Holly A
Hammond, Telford, PA (US)

(73) Assignee: Merck Sharp & Dohme Corp.,
Rahway, NJ (US)

( * ) Notice: Subject to any disclaimer, the term of this patent is extended or adjusted under 35 U.S.C. 154(b) by 0 days.

(21) Appl. No.: 13/242,744

(22) Filed: Sep. 23, 2011

(65) Prior Publication Data
US 2012/0082679 A1 Apr. 5, 2012

Related U.S. Application Data

(63) Continuation of application No. 12/312,397, filed as application No. PCT/US2007/023214 on Nov. 2, 2007, now abandoned.

(60) Provisional application No. 60/857,293, filed on Nov. 7, 2006, provisional application No. 60/857,248, filed on Nov. 7, 2006.

(51) Int. Cl.
*C07K 16/40* (2006.01)
*C07K 16/00* (2006.01)
*A61K 39/395* (2006.01)
*C12N 15/00* (2006.01)
*C12N 15/85* (2006.01)
*C07H 21/04* (2006.01)

(52) U.S. Cl. ............. 530/388.26; 530/387.1; 530/388.1; 536/23.53; 435/320.1; 435/455; 435/69.6; 424/146.1; 424/130.1; 424/141.1

(58) Field of Classification Search .................. None
See application file for complete search history.

(56) References Cited

U.S. PATENT DOCUMENTS

| | | | |
|---|---|---|---|
| 2002/0045571 | A1 | 4/2002 | Liu et al. |
| 2003/0119038 | A1 | 6/2003 | Bingham et al. |
| 2004/0009553 | A1 | 1/2004 | Glucksmann et al. |
| 2004/0248177 | A1 | 12/2004 | Abi Fadel et al. |
| 2005/0147612 | A1 | 7/2005 | Yayon et al. |
| 2009/0232795 | A1 | 9/2009 | Condra et al. |
| 2010/0040610 | A1 | 2/2010 | Sitlani et al. |
| 2010/0040611 | A1 | 2/2010 | Sparrow et al. |
| 2010/0041102 | A1 | 2/2010 | Sitlani et al. |

FOREIGN PATENT DOCUMENTS

| | | |
|---|---|---|
| EP | 1067182 | 1/2001 |
| EP | 1440981 | 7/2004 |
| EP | 1471152 | 10/2004 |
| WF | WO 2008/057459 | 5/2008 |
| WO | WO 01/31007 | 5/2001 |
| WO | WO 01/34768 | 5/2001 |
| WO | WO 01/57081 | 8/2001 |
| WO | WO 01/77137 | 10/2001 |
| WO | WO 01/98468 | 12/2001 |
| WO | WO 02/14358 | 2/2002 |
| WO | WO 02/46383 | 6/2002 |
| WO | WO 02/046383 | 7/2002 |
| WO | WO 02/090526 | 11/2002 |
| WO | WO 02/102993 | 12/2002 |
| WO | WO 02/102994 | 12/2002 |
| WO | WO 2004/018649 | 3/2004 |
| WO | WO 2004/097047 | 11/2004 |
| WO | WO 2007/134161 | 11/2007 |
| WO | WO 2008/057457 | 5/2008 |
| WO | WO 2008/057458 | 5/2008 |
| WO | WO 2008/063382 | 5/2008 |
| WO | WO 2008/086395 | 7/2008 |
| WO | WO 2008/118386 | 10/2008 |
| WO | WO 2008/125623 | 10/2008 |
| WO | WO 2008/133647 | 11/2008 |
| WO | WO 2009/026558 | 2/2009 |
| WO | WO 2009/055783 | 4/2009 |
| WO | WO 2009/100318 | 8/2009 |
| WO | WO 2010/029513 | 3/2010 |

OTHER PUBLICATIONS

GenomeNet—Database: PIR, Entry: T18240, Barrell et al., LinkDB: T18240(Sep. 7, 2004).
GenomeNet—Database: UniProt, Entry: A0E922_PARTE, Aury et al., LinkDB: A0E922_PARTE (Mar. 2006).
Benjannet et al., 2006 J. Biol. Chem, 281(41):30561-72 . Epub Aug. 15, 2006.
Rabbit Anti-PCSK9 Polyclonal Antibody, Unconjugated from Cayman Chemical Catalog No. 10007185-1, 2006.
Goat Anti-PCSK0 Polyclonal Antibody, Unconjugated from Novus Biologicals, Catalog No. NB-300-959, 2006.
Knappik et al., 2000 J. Mol. Biol. 296:57-86.
Grozdanov et al., 2006 Biochem Cell Biol 84:80-92.
Alborn et al., 2007 Clinical Chemistry, 53:1814-1819.
Horton et al., 2007 Trends Biochem Sciences 32:71-77.
Ni et al., 2010 J Biol Chem. 285(17):12882-91. Feb. 19, 2010. [Epub ahead of print].
Ni et al., vol. 120, No. 18, Suppl. 2, 2009, p. S477, XP008121212, ISSN: 0009-7322.
Lopez et al., 2008 Biochim Biophy Acta 1781:184-191.
Lopez, 2008 Drug News & Perspectives 21:323-330.
Chan et al., Proc Natl Acad Sci U S A. Jun. 16, 2009;106(24):9820-5 Epub May 14, 2009.

(Continued)

*Primary Examiner* — Sharon Wen
(74) *Attorney, Agent, or Firm* — Anna L. Cocuzzo; Sheela Mohan-Peterson

(57) ABSTRACT

Antagonists of human proprotein convertase subtilisin-kexin type 9 ("PCSK9") are disclosed. The disclosed antagonists are effective in the inhibition of PCSK9 function and, accordingly, present desirable antagonists for the use in the treatment of conditions associated with PCSK9 activity. The present invention also discloses nucleic acid encoding said antagonists, vectors, host cells, and compositions comprising the antagonists. Methods of making PCSK9-specific antagonists as well as methods of using the antagonists for inhibiting or antagonizing PCSK9 function are also disclosed and form important additional aspects of the present disclosure.

20 Claims, 6 Drawing Sheets

OTHER PUBLICATIONS

Peterson et al., 2008 J Lipid Res. 49(7):1595-9.
Pandit et al., 2008 J Lipid Res. 49(6):1333-43. Epub Mar. 19, 2008.
Fisher et al., 2007 J Biol Chem. 282(28):20502-12. Epub May 10, 2007.
Maxwell & Breslow, 2004 PNAS 101: 7100-7105.
Naureckiene et al., 2003 Archives Biochemistry Biophysics 420:55-67.
Park et al., 2004 J. Biol. Chem. 279:50630-50638.
Bottomley et al., 2009 J Biol Chem 284(2):1313-23. Epub Nov. 10, 2008.
Benjannet et al., 2004 J. Biol. Chem, 279:48865-48875.
Molloy et al., 1994 EMBO J. 13:18-33.
Seidah et al., 2003 PNAS 100:928-933.
Zhao et al., 2006 Am J Hum Genet. Sep. 2006; 79(3): 514-523.
Lagace et al., 2006 J Clin Invest 116:2995-3005.
Cameron et al, 2006 Hum Mol Genet 15:1551-1558.
Lalanne et al., 2005 J. Lipid Research 46:1312-1319.
Cohen et al., 2006 N Engl J Med 354:1264-1272.
Cohen et al., 2005 Nat. Genet. 37:161-165, Epub Jan. 16, 2005. Erratum in: Nat Genet. Mar. 2005;37(3):328.
Maxwell et al. *2003 J Lipid Research* 44:2109-2119.
Rashid et al., 2005 PNAS 102:5374-5379 Epub Apr. 1, 2005.
Chen et al., 2003 Pharm Res 20:1952-1960.
Akers et al., 2002 Pharm Biotech 14:47-127.
Zhang et al., 2007 J. Biol. Chem. 282:18602-18612.
Kwon et al., 2008 PNAS 105:1820-1825.
Brown M, Rittenburg MB, Chen C, Roberts VA. Tolerance of single, but not multiple, amino acid replacements in antibody VH CDR 2: a means of minimizing B cell wastage from somatic hypermutation? J Immunol. May 1, 1996;156 (9):3285-91.
Wark Kl, Hudson PJ.Latest technologies for the enhancement of antibody affinity. Adv Drug Deily Rev. Aug. 7, 2006;58 (5-6):657-70. Epub May 22, 2006.
Maynard J, Georgiou G. Antibody engineering. Annu Rev Biomed Eng. 2000;2:339-76.
Antibodies online: "PCSK9 antibody", Antibodies online, 2005, Retrieved from internet: URL: http://www.antibodies-online.com/productsheets/en/ABIN185371.pdf.

```
                          |----CH1 →
IGG1                      ASTK GPSVFPLAPS SKSTSGGTAA LGCLVKDYFP
IGG2                      ASTK GPSVFPLAPC SRSTSESTAA LGCLVKDYFP
IGG4                      ASTK GPSVFPLAPC SRSTSESTAA LGCLVKDYFP
IGG2M4                    ASTK GPSVFPLAPC SRSTSESTAA LGCLVKDYFP

C200
IGG1    EPVTVSWNSG ALTSGVHTFP AVLQSSGLYS LSSVVTVPSS SLGTQTYICN VNHKPSNTKV
IGG2    EPVTVSWNSG ALTSGVHTFP AVLQSSGLYS LSSVVTVTSS NFGTQTYTCN VDHKPSNTKV
IGG4    EPVTVSWNSG ALTSGVHTFP AVLQSSGLYS LSSVVTVPSS SLGTKTYTCN VDHKPSNTKV
IGG2M4  EPVTVSWNSG ALTSGVHTFP AVLQSSGLYS LSSVVTVTSS NFGTQTYTCN VDHKPSNTKV

----Hinge region---|----CH2 →   P238              M252         C261 D265 D270
IGG1    DKKAEPKSCD KTHTCPPCPA PELLGGPSVF LFPPKPKDTL MISRTPEVTC VVVDVSHEDP
IGG2    DKTVERKCC- ---VECPPCPA PP-VAGPSVF LFPPKPKDTL MISRTPEVTC VVVDVSHEDP
IGG4    DKRVESKYGP ----PCPSCPA PEFLGGPSVF LFPPKPKDTL MISRTPEVTC VVVDVSQEDP
IGG2M4  DKTVERKCC- ---VECPPCPA PP-VAGPSVF LFPPKPKDTL MISRTPEVTC VVVDVSQEDP
                       (Lower hinge)               FcRn-bind        B/C loop N297*            T307              C321        P329
IGG1    EVKFNWYVDG VEVHNAKTKP REEQYNSTYR VVSVLTVLHQ DWLNGKEYKC KVSNKALPAPI
IGG2    EVQFNWYVDG VEVHNAKTKP REEQFNSTFR VVSVLTVVHQ DWLNGKEYKC KVSNKGLPAPI
IGG4    EVQFNWYVDG VEVHNAKTKP REEQFNSTYR VVSVLTVLHQ DWLNGKEYKC KVSNKGLPSSI
IGG2M4  EVQFNWYVDG VEVHNAKTKP REEQFNSTYR VVSVLTVLHQ DWLNGKEYKC KVSNKGLPSSI
                                 C'E loop    FcRn-bind        F/G loop

|---CH3 →
IGG1    EKTISKAKG QPREPQVYTL PPSRDELTKN QVSLTCLVKG FYPSDIAVEW ESNGQPENNY
IGG2    EKTISKTKG QPREPQVYTL PPSREEMTKN QVSLTCLVKG FYPSDIAVEW ESNGQPENNY
IGG4    EKTISKAKG QPREPQVYTL PPSQEEMTKN QVSLTCLVKG FYPSDIAVEW ESNGQPENNY
IGG2M4  EKTISKTKG QPREPQVYTL PPSREEMTKN QVSLTCLVKG FYPSDIAVEW ESNGQPENNY

H433
IGG1    KTTPPVLDSD GSFFLYSKLT VDKSRWQQGN VFSCSVMHEA LHNHYTQKSL SLSPGK*
        (SEQ ID NO: 89)
IGG2    KTTPPMLDSD GSFFLYSKLT VDKSRWQQGN VFSCSVMHEA LHNHYTQKSL SLSPGK*
        (SEQ ID NO: 90)
IGG4    KTTPPVLDSD GSFFLYSRLT VDKSRWQEGN VFSCSVMHEA LHNHYTQKSL SLSLGK*
        (SEQ ID NO: 91)
IGG2M4  KTTPPMLDSD GSFFLYSKLT VDKSRWQQGN VFSCSVMHEA LHNHYTQKSL SLSPGK*
        (SEQ ID NO: 92)
                                                      FcRn-bind
```

FIG. 6

ANTAGONISTS OF PCSK9

CROSS-REFERENCE TO RELATED APPLICATIONS

This application is a continuation of U.S. Ser. No. 12/312,397 filed on May 7, 2009 which is a 371 of PCT/US07/023,214 filed on Nov. 2, 2007 which claims the benefit of U.S. Provisional Application Nos. 60/857,293 and 60/857,248, both filed on Nov. 7, 2006, each of which are herein incorporated by reference in its entireties.

STATEMENT REGARDING FEDERALLY-SPONSORED R&D

Not Applicable.

REFERENCE TO MICROFICHE APPENDIX

Not Applicable.

BACKGROUND OF THE INVENTION

Proprotein convertase subtilisin-kexin type 9 (hereinafter called "PCSK9"), also known as neural apoptosis-regulated convertase 1 ("NARC-1"), is a proteinase K-like subtilase identified as the $9^{th}$ member of the secretory subtilase family; see Seidah et al., 2003 *PNAS* 100:928-933. The gene for PCSK9 localizes to human chromosome 1p33-p34.3; Seidah et al., supra. PCSK9 is expressed in cells capable of proliferation and differentiation including, for example, hepatocytes, kidney mesenchymal cells, intestinal ileum, and colon epithelia as well as embryonic brain telencephalon neurons; Seidah et al., supra.

Original synthesis of PCSK9 is in the form of an inactive enzyme precursor, or zymogen, of ~72-kDa which undergoes autocatalytic, intramolecular processing in the endoplasmic reticulum ("ER") to activate its functionality. This internal processing event has been reported to occur at the SSVFAQ↓SIPWNL$^{158}$ motif rendering the first three N-terminal residues Ser-Ile-Pro (Benjannet et al., 2004 *J. Biol. Chem.* 279:48865-48875), and has been reported as a requirement of exit from the ER; Benjannet et al., supra; Seidah et al., supra. The cleaved protein is then secreted. The cleaved peptide remains associated with the activated and secreted enzyme; supra.

The gene sequence for human PCSK9, which is ~22-kb long with 12 exons encoding a 692 amino acid protein, can be found, for example, at Deposit No. NP_777596.2. Human, mouse and rat PCSK9 nucleic acid sequences have been deposited; see, e.g., GenBank Accession Nos.: AX127530 (also AX207686), AX207688, and AX207690, respectively.

PCSK9 is disclosed and/or claimed in several patent publications including, but not limited to the following: PCT Publication Nos. WO 01/31007, WO 01/57081, WO 02/14358, WO 01/98468, WO 02/102993, WO 02/102994, WO 02/46383, WO 02/90526, WO 01/77137, and WO 01/34768; US Publication Nos. US 2004/0009553 and US 2003/0119038, and European Publication Nos. EP 1 440 981, EP 1 067 182, and EP 1 471 152.

PCSK9 has been ascribed a role in the differentiation of hepatic and neuronal cells (Seidah et al., supra.), is highly expressed in embryonic liver, and has been strongly implicated in cholesterol homeostasis. Recent studies seem to suggest a specific role in cholesterol biosynthesis or uptake. In a study of cholesterol-fed rats, Maxwell et al. found that PCSK9 was downregulated in a similar manner as three other genes involved in cholesterol biosynthesis, Maxwell et al., 2003 *J. Lipid Res.* 44:2109-2119. Interestingly, as well, the expression of PCSK9 was regulated by sterol regulatory element-binding proteins ("SREBP"), as seen with other genes involved in cholesterol metabolism; supra. These findings were later supported by a study of PCSK9 transcriptional regulation which demonstrated that such regulation was quite typical of other genes implicated in lipoprotein metabolism; Dubuc et al., 2004 *Arterioscler. Thromb. Vasc. Biol.* 24:1454-1459. PCSK9 expression was upregulated by statins in a manner attributed to the cholesterol-lowering effects of the drugs; supra. More, the PCSK9 promoters possessed two conserved sites involved in cholesterol regulation, a sterol regulatory element and an Sp1 site; supra. Adenoviral expression of PCSK9 has been shown to lead to a notable time-dependent increase in circulating LDL (Benjannet et al., 2004 *J. Biol. Chem.* 279:48865-48875). More, mice deleted of the PCSK9 gene have increased levels of hepatic LDL receptors and more rapidly clear LDL from the plasma; Rashid et al., 2005 *Proc. Natl. Acad. Sci. USA* 102:5374-5379. Recently it was reported that medium from HepG2 cells transiently transfected with PCSK9 reduced the amount of cell surface LDLR and internalization of LDL when transferred to untransfected HepG2 cells; see Cameron et al., 2006 *Human Mol. Genet.* 15:1551-1558. It was concluded that either PCSK9 or a factor acted upon by PCSK9 is secreted and is capable of degrading LDLR both in transfected and untransfected cells. More recently, it was demonstrated that purified PCSK9 added to the medium of HepG2 cells had the effect of reducing the number of cell-surface LDLRs in a dose- and time-dependent manner; Lagace et al., 2006 *J. Clin. Invest.* 116:2995-3005.

A number of mutations in the gene PCSK9 have also been conclusively associated with autosomal dominant hypercholesterolemia ("ADH"), an inherited metabolism disorder characterized by marked elevations of low density lipoprotein ("LDL") particles in the plasma which can lead to premature cardiovascular failure; see Abifadel et al., 2003 *Nature Genetics* 34:154-156; Timms et al., 2004 *Hum. Genet.* 114:349-353; Leren, 2004 *Clin. Genet.* 65:419-422. A later-published study on the S127R mutation of Abifadel et al., supra, reported that patients carrying such a mutation exhibited higher total cholesterol and apoB100 in the plasma attributed to (1) an overproduction of apoB100-containing lipoproteins, such as low density lipoprotein ("LDL"), very low density lipoprotein ("VLDL") and intermediate density lipoprotein ("IDL"), and (2) an associated reduction in clearance or conversion of said lipoproteins; Ouguerram et al., 2004 *Arterioscler. Thromb. Vasc. Biol.* 24:1448-1453.

Together, the studies referenced above evidence the fact that PCSK9 plays a role in the regulation of LDL production. Expression or upregulation of PCSK9 is associated with increased plasma levels of LDL cholesterol, and inhibition or the lack of expression of PCSK9 is associated with low LDL cholesterol plasma levels. Significantly, lower levels of LDL cholesterol associated with sequence variations in PCSK9 have conferred protection against coronary heart disease; Cohen, 2006 *N. Engl. J. Med.* 354:1264-1272

The identification of compounds and/or agents effective in the treatment of cardiovascular affliction is highly desirable. Reductions in LDL cholesterol levels have already demonstrated in clinical trials to be directly related to the rate of coronary events; Law et al., 2003 *BMJ* 326:1423-1427. More, recently moderate lifelong reduction in plasma LDL cholesterol levels has been shown to be substantially correlated with a substantial reduction in the incidence of coronary events; Cohen et al., supra. This was found to be the case even in populations with a high prevalence of non-lipid-related cardiovascular risk factors; supra. Accordingly, there is great benefit to be reaped from the managed control of LDL cholesterol levels.

Accordingly, it would be of great import to produce a therapeutic-based antagonist of PCSK9 that inhibits or antagonizes the activity of PCSK9 and the corresponding role PCSK9 plays in various therapeutic conditions.

SUMMARY OF THE INVENTION

The present invention relates to antagonists of PCSK9 and particularly human PCSK9. Protein-specific antagonists of PCSK9 (or "PCSK9-specific antagonists" as referred to herein) are PCSK9 protein-specific binding molecules or proteins effective in the inhibition of PCSK9 function which are of import in the treatment of conditions associated with or impacted by PCSK9 function, including, but not limited to hypercholesterolemia, coronary heart disease, metabolic syndrome, acute coronary syndrome and related conditions. PCSK9-specific antagonists are characterized by selective recognition and binding to PCSK9. PCSK9-specific antagonists do not show significant binding to other than PCSK9, other than in those specific instances where the antagonist is supplemented to confer an additional, distinct specificity to the PCSK9-specific binding portion. In specific embodiments, PCSK-9 specific antagonists bind to human PCSK9 with a KD of $1.2 \times 10\text{-}6$ or less. In specific embodiments, PCSK9-specific antagonists bind to human PCSK9 with a KD of $1 \times 10\text{-}7$ or less. In additional embodiments, PCSK9-specific antagonists bind to human PCSK9 with a KD of $1 \times 10\text{-}8$ or less. In other embodiments, PCSK9-specific antagonists bind to human PCSK9 with a KD of $5 \times 10\text{-}9$ or less, or of $1 \times 10\text{-}9$ or less. In further embodiments, PCSK9-specific antagonists bind to human PCSK9 with a KD of $1 \times 10\text{-}10$ or less, a KD of $1 \times 10\text{-}11$ or less, or a KD of $1 \times 10\text{-}12$ or less. In specific embodiments, PCSK9-specific antagonists do not bind other proteins at the above levels.

PCSK9-specific antagonists are effective in counteracting PCSK9-dependent inhibition of cellular LDL-uptake. Repeatedly, PCSK9-specific antagonists demonstrate dose-dependent inhibition of the effects of PCSK9 on LDL uptake. Accordingly, PCSK9-specific antagonists are of import for lowering plasma LDL cholesterol levels. Said antagonists also have utility for various diagnostic purposes in the detection and quantification of PCSK9.

In specific embodiments, the present invention encompasses PCSK9-specific antagonists, and, in specific embodiments, antibody molecules, comprising disclosed heavy and/or light chain variable regions, equivalents having one or more conservative amino acid substitutions, and homologs thereof. Particular embodiments comprise isolated PCSK9-specific antagonists that comprise disclosed CDR domains or sets of the heavy and/or light chain CDR domains, and equivalents thereof characterized as having one or more conservative amino acid substitutions. As will be appreciated by those skilled in the art, fragments of PCSK9-specific antagonists that retain the ability to antagonize PCSK9 may be inserted into various frameworks, see, e.g., U.S. Pat. No. 6,818,418 and references contained therein which discuss various scaffolds which may be used to display antibody loops previously selected on the basis of antigen binding. In the alternative, genes encoding for VL and VH may be joined, using recombinant methods, for example using a synthetic linker that enables them to be made as a single protein chain in which the VL and VH regions pair to form monovalent molecules, otherwise known as single chain Fvs ("ScFVs"); see, e.g., Bird et al., 1988 *Science* 242: 423-426, and Huston et al., 1988 *Proc. Natl. Acad. Sci. USA* 85:5879-5883.

PCSK-9 specific antagonists and fragments may be in the form of various non-antibody-based scaffolds, including but not limited to avimers (Avidia); DARPins (Molecular Partners); Adnectins (Adnexus), Anticalins (Pieris) and Affibodies (Affibody). The use of alternative scaffolds for protein binding is well appreciated in the scientific literature, see, e.g., Binz & Plückthun, 2005 *Curr. Opin. Biotech.* 16:1-11. Accordingly, non-antibody-based scaffolds or antagonist molecules with selectivity for PCSK9 that counteract PCSK9-dependent inhibition of cellular LDL-uptake form important embodiments of the present invention.

In another aspect, the present invention provides nucleic acid encoding disclosed PCSK9-specific antagonists. The present invention provides, in particular aspects, nucleic acid encoding PCSK9-specific antagonists, and in specific embodiments, disclosed antibody molecules, which comprise disclosed variable heavy and light regions and select components thereof, particularly the disclosed respective CDR3 regions. In another aspect, the present invention provides vectors comprising said nucleic acid. In another aspect, the present invention provides isolated cell(s) comprising nucleic acid encoding disclosed PCSK9-specific antagonists, in specific embodiments, disclosed antibody molecules and components thereof as described. In another aspect, the present invention provides isolated cell(s) comprising a polypeptide, or vector of the present invention.

In another aspect, the present invention provides a method of making PCSK9-specific antagonists which selectively bind PCSK9 including but not limited to antibodies, antigen binding fragments, derivatives, chimeric molecules, fusions of any of the foregoing with another polypeptide, or alternative structures/compositions capable of specifically binding PCSK9. The method comprises incubating a cell comprising nucleic acid encoding the PCSK9-specific antagonist(s), or comprising individual nucleic acids encoding one or more components thereof, said nucleic acids, which when expressed, collectively produce the antagonist(s), under conditions that allow for the expression and/or assembly of the PCSK9-specific antagonist(s), and isolating said antagonist(s) from the cell. One of skill in the art can obtain PCSK9-specific antagonists disclosed herein as well using standard recombinant DNA techniques.

In another aspect, the present invention provides a method for antagonizing the activity or function of PCSK9, or a noted effect of PCSK9, which comprises contacting a cell, population of cells, or tissue sample of interest expressing PCSK9 (or treated with PCSK9) with a PCSK9-specific antagonist disclosed herein under conditions that allow said antagonist to bind to PCSK9. Specific embodiments of the present invention include such methods wherein the cell is a human cell. Antagonists in accordance herewith are effective in the inhibition of PCSK9 function. Disclosed PCSK9-specific antagonists were found to dose dependently inhibit the effects of PCSK9 on LDL uptake.

In another aspect, the present invention provides a method for antagonizing the activity of PCSK9 in a subject exhibiting a condition associated with PCSK9 activity, or a condition where the functioning of PCSK9 is contraindicated for a particular subject, which comprises administering to the subject a therapeutically effective amount of a PCSK9-specific antagonist of the present invention. In select embodiments, the condition may be hypercholesterolemia, coronary heart disease, metabolic syndrome, acute coronary syndrome or related conditions. In another aspect, the present invention provides a pharmaceutical composition or other composition comprising a PCSK9-specific antagonist of the invention and a pharmaceutically acceptable carrier, excipient, diluent, stabilizer, buffer, or alternative designed to facilitate administration of the antagonist in the desired amount to the treated individual.

The present invention also relates to a method for identifying PCSK9 antagonists in a cell sample which comprises providing purified PCSK9 and labeled LDL particles to a cell sample; providing a molecule(s) suspected of being a PCSK9 antagonist to the cell sample; incubating the cell sample for a period of time sufficient to allow LDL particle uptake by the cells; isolating cells of the cell sample by removing the supernate; reducing non-specific association of labeled LDL particles; lysing the cells; quantifying the amount of label retained within the cell lysate; and identifying those candidate antagonists that result in an increase in the amount of quantified label as compared with that observed when PCSK9 is administered alone. Candidate antagonists that result in an increase in the amount of quantified label are PCSK9 antagonists. This method has proven to be an effective means for identifying PCSK9-specific antagonists and, thus, forms an important aspect of the present invention.

The following table offers a generalized outline of the sequences discussed in the present application:

TABLE 1

| SEQ ID NO: | DESCRIPTION |
| --- | --- |
| SEQ ID NO: 1 | LIGHT CHAIN ("LC"); 1CX1G08 |
| SEQ ID NO: 2 | LC NUCLEIC ACID; 1CX1G08 |
| SEQ ID NO: 3 | VL CDR1; 1CX1G08 |
| SEQ ID NO: 4 | VL CDR1 NUCLEIC ACID; 1CX1G08 |
| SEQ ID NO: 5 | VL CDR2; 1CX1G08; 3BX5C01 |
| SEQ ID NO: 6 | VL CDR2 NUCLEIC ACID; 1CX1G08; 3BX5C01 |
| SEQ ID NO: 7 | VL CDR3; 1CX1G08 |
| SEQ ID NO: 8 | VL CDR3 NUCLEIC ACID; 1CX1G08 |
| SEQ ID NO: 9 | Fd CHAIN; 1CX1G08 |
| SEQ ID NO: 10 | Fd CHAIN NUCLEIC ACID; 1CX1G08 |
| SEQ ID NO: 11 | VH; 1CX1G08 |
| SEQ ID NO: 12 | VH NUCLEIC ACID; 1CX1G08 |
| SEQ ID NO: 13 | VH CDR1; 1CX1G08 |
| SEQ ID NO: 14 | VH CDR1 NUCLEIC ACID; 1CX1G08 |
| SEQ ID NO: 15 | VH CDR2; 1CX1G08 |
| SEQ ID NO: 16 | VH CDR2 NUCLEIC ACID; 1CX1G08 |
| SEQ ID NO: 17 | VH CDR3; 1CX1G08 |
| SEQ ID NO: 18 | VH CDR3 NUCLEIC ACID; 1CX1G08 |
| SEQ ID NO: 19 | LIGHT CHAIN ("LC"); 3BX5C01 |
| SEQ ID NO: 20 | LC NUCLEIC ACID; 3BX5C01 |
| SEQ ID NO: 21 | VL CDR1; 3BX5C01 |
| SEQ ID NO: 22 | VL CDR1 NUCLEIC ACID; 3BX5C01 |
| SEQ ID NO: 23 | VL CDR3; 3BX5C01 |
| SEQ ID NO: 24 | VL CDR3 NUCLEIC ACID; 3BX5C01 |
| SEQ ID NO: 25 | Fd CHAIN; 3BX5C01 |
| SEQ ID NO: 26 | Fd CHAIN NUCLEIC ACID; 3BX5C01 |
| SEQ ID NO: 27 | VH; 3BX5C01 |
| SEQ ID NO: 28 | VH NUCLEIC ACID; 3BX5C01 |
| SEQ ID NO: 29 | VH CDR1; 3BX5C01 |
| SEQ ID NO: 30 | VH CDR1 NUCLEIC ACID; 3BX5C01 |
| SEQ ID NO: 31 | VH CDR2; 3BX5C01 |
| SEQ ID NO: 32 | VH CDR2 NUCLEIC ACID; 3BX5C01 |
| SEQ ID NO: 33 | VH CDR3; 3BX5C01 |
| SEQ ID NO: 34 | VH CDR3 NUCLEIC ACID; 3BX5C01 |
| SEQ ID NO: 35 | LIGHT CHAIN ("LC"); 3CX2A06 |
| SEQ ID NO: 36 | LC NUCLEIC ACID; 3CX2A06 |
| SEQ ID NO: 37 | VL CDR1; 3CX2A06 |
| SEQ ID NO: 38 | VL CDR1 NUCLEIC ACID; 3CX2A06 |
| SEQ ID NO: 39 | VL CDR2; 3CX2A06; 3CX3D02 |
| SEQ ID NO: 40 | VL CDR2 NUCLEIC ACID; 3CX2A06; 3CX3D02 |
| SEQ ID NO: 41 | VL CDR3; 3CX2A06 |
| SEQ ID NO: 42 | VL CDR3 NUCLEIC ACID; 3CX2A06 |
| SEQ ID NO: 43 | Fd CHAIN; 3CX2A06 |
| SEQ ID NO: 44 | Fd CHAIN NUCLEIC ACID; 3CX2A06 |
| SEQ ID NO: 45 | VH; 3CX2A06 |
| SEQ ID NO: 46 | VH NUCLEIC ACID; 3CX2A06 |
| SEQ ID NO: 47 | VH CDR1; 3CX2A06 |

TABLE 1-continued

| SEQ ID NO: | DESCRIPTION |
| --- | --- |
| SEQ ID NO: 48 | VH CDR1 NUCLEIC ACID; 3CX2A06 |
| SEQ ID NO: 49 | VH CDR2; 3CX2A06 |
| SEQ ID NO: 50 | VH CDR2 NUCLEIC ACID; 3CX2A06 |
| SEQ ID NO: 51 | VH CDR3; 3CX2A06 |
| SEQ ID NO: 52 | VH CDR3 NUCLEIC ACID; 3CX2A06 |
| SEQ ID NO: 53 | LIGHT CHAIN ("LC"); 3CX3D02 |
| SEQ ID NO: 54 | LC NUCLEIC ACID; 3CX3D02 |
| SEQ ID NO: 55 | VL CDR1; 3CX3D02 |
| SEQ ID NO: 56 | VL CDR1 NUCLEIC ACID; 3CX3D02 |
| SEQ ID NO: 57 | VL CDR3; 3CX3D02 |
| SEQ ID NO: 58 | VL CDR3 NUCLEIC ACID; 3CX3D02 |
| SEQ ID NO: 59 | Fd CHAIN; 3CX3D02 |
| SEQ ID NO: 60 | Fd CHAIN NUCLEIC ACID; 3CX3D02 |
| SEQ ID NO: 61 | VH; 3CX3D02 |
| SEQ ID NO: 62 | VH NUCLEIC ACID; 3CX3D02 |
| SEQ ID NO: 63 | VH CDR1; 3CX3D02 |
| SEQ ID NO: 64 | VH CDR1 NUCLEIC ACID; 3CX3D02 |
| SEQ ID NO: 65 | VH CDR2; 3CX3D02 |
| SEQ ID NO: 66 | VH CDR2 NUCLEIC ACID; 3CX3D02 |
| SEQ ID NO: 67 | VH CDR3; 3CX3D02 |
| SEQ ID NO: 68 | VH CDR3 NUCLEIC ACID; 3CX3D02 |
| SEQ ID NO: 69 | LIGHT CHAIN ("LC"); 3CX4B08 |
| SEQ ID NO: 70 | LC NUCLEIC ACID; 3CX4B08 |
| SEQ ID NO: 71 | VL CDR1; 3CX4B08 |
| SEQ ID NO: 72 | VL CDR1 NUCLEIC ACID; 3CX4B08 |
| SEQ ID NO: 73 | VL CDR2; 3CX4B08 |
| SEQ ID NO: 74 | VL CDR2 NUCLEIC ACID; 3CX4B08 |
| SEQ ID NO: 75 | VL CDR3; 3CX4B08 |
| SEQ ID NO: 76 | VL CDR3 NUCLEIC ACID; 3CX4B08 |
| SEQ ID NO: 77 | Fd CHAIN; 3CX4B08 |
| SEQ ID NO: 78 | Fd CHAIN NUCLEIC ACID; 3CX4B08 |
| SEQ ID NO: 79 | VH; 3CX4B08 |
| SEQ ID NO: 80 | VH NUCLEIC ACID; 3CX4B08 |
| SEQ ID NO: 81 | VH CDR1; 3CX4B08 |
| SEQ ID NO: 82 | VH CDR1 NUCLEIC ACID; 3CX4B08 |
| SEQ ID NO: 83 | VH CDR2; 3CX4B08 |
| SEQ ID NO: 84 | VH CDR2 NUCLEIC ACID; 3CX4B08 |
| SEQ ID NO: 85 | VH CDR3; 3CX4B08 |
| SEQ ID NO: 86 | VH CDR3 NUCLEIC ACID; 3CX4B08 |
| SEQ ID NO: 87 | IgG2m4 |
| SEQ ID NO: 88 | IgG2m4 NUCLEIC ACID |
| SEQ ID NO: 89 | Contains IgG1 Fc |
| SEQ ID NO: 90 | Contains IgG2 Fc |
| SEQ ID NO: 91 | Contains IgG4 Fc |
| SEQ ID NO: 92 | Contains IgG2m4 Fc |
| SEQ ID NO: 93 | VL; 1CX1G08 |
| SEQ ID NO: 94 | VL NUCLEIC ACID; 1CX1G08 |
| SEQ ID NO: 95 | VL; 3BX5C01 |
| SEQ ID NO: 96 | VL NUCLEIC ACID; 3BX5C01 |
| SEQ ID NO: 97 | VL; 3CX2A06 |
| SEQ ID NO: 98 | VL NUCLEIC ACID; 3CX2A06 |
| SEQ ID NO: 99 | VL; 3CX3D02 |
| SEQ ID NO: 100 | VL NUCLEIC ACID; 3CX3D02 |
| SEQ ID NO: 101 | VL; 3CX4B08 |
| SEQ ID NO: 102 | VL NUCLEIC ACID; 3CX4B08 |

BRIEF DESCRIPTION OF THE DRAWINGS

FIGS. 3B and 3D have two controls: (i) a cell only control, showing the basal level of cellular LDL uptake, and (ii) a cell+PCSK9 (25 μg/ml) control which shows the level of PCSK9-dependent loss of LDL-uptake. The titration experiments which contain Fab and PCSK9 were done at a fixed concentration of PCSK9 (25 μg/ml) and increasing concentrations of Fab shown in the graphs. FIGS. 3A and 3C show calculations of IC-50s.

FIGS. 4B and 4D have two controls: (i) a cell only control, showing the basal level of cellular LDL uptake, and (ii) a cell+PCSK9 (25 µg/ml) control which shows the level of PCSK9-dependent loss of LDL-uptake. The titration experiments which contain Fab and PCSK9 were done at a fixed concentration of PCSK9 (25 µg/ml) and increasing concentrations of Fab shown in the graphs. FIGS. 4A and 4C show calculations of IC-50s.

FIG. 5B has two controls: (i) a cell only control, showing the basal level of cellular LDL uptake, and (ii) a cell+PCSK9 (25 µg/ml) control which shows the level of PCSK9-dependent loss of LDL-uptake. The titration experiment which contains Fab and PCSK9 was done at a fixed concentration of PCSK9 (25 µg/ml) and increasing concentrations of Fab shown in the graph. FIG. 5A shows calculations of IC-50.

FIG. 6 illustrates a sequence comparison of the Fc domains of IgG1 (residues 24-353 of SEQ ID NO: 89), IgG2 (residues 7-332 of SEQ ID NO: 90), IgG4 (residues 7-333 of SEQ ID NO: 91) and the IgG2 m4 (residues 7-332 of SEQ ID NO: 92) isotypes.

DETAILED DESCRIPTION OF THE INVENTION

Figure 1:
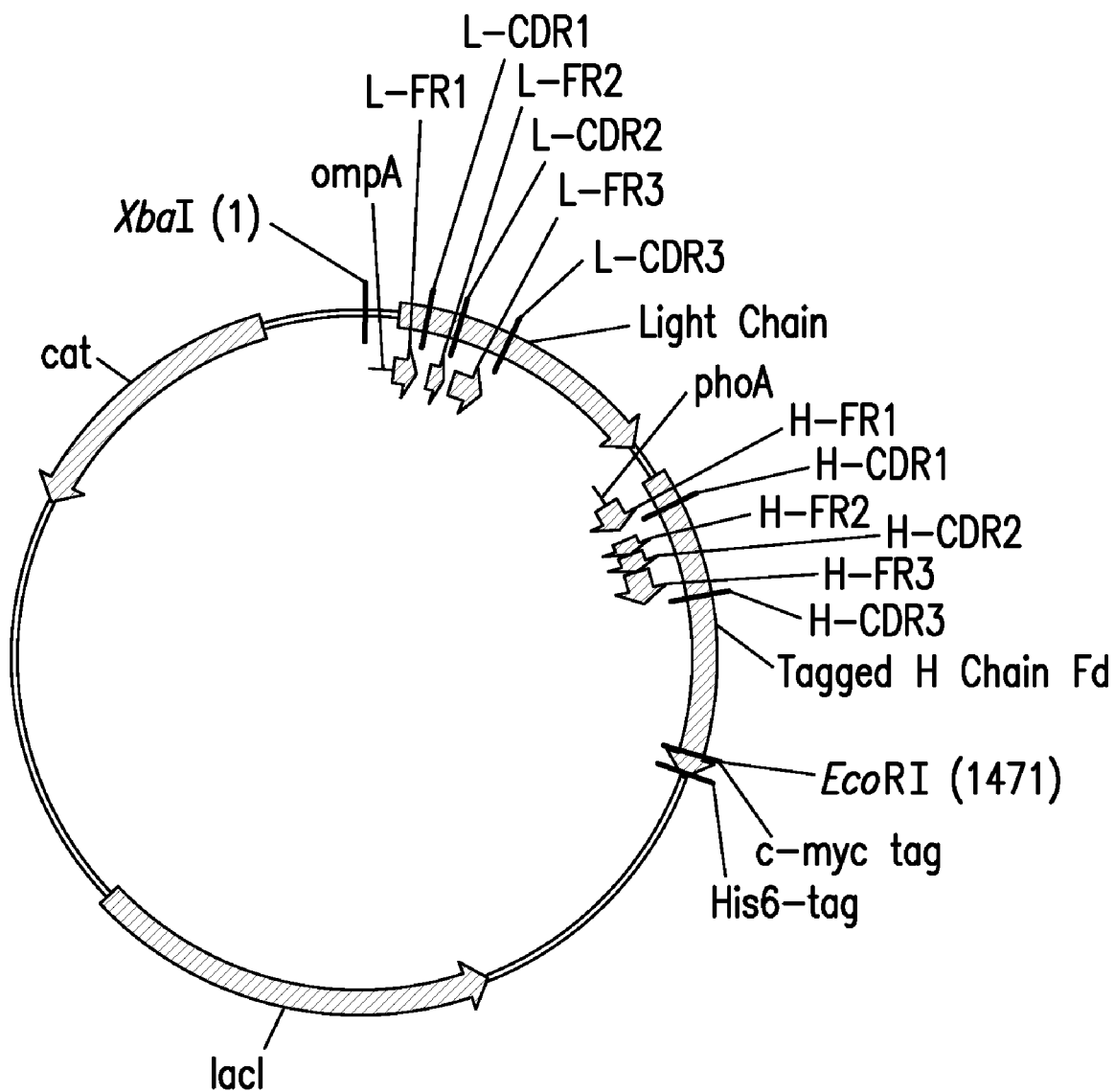
FIG. 1 illustrates Fab expression vector pMORPH_x9_MH.

The present invention relates to antagonists of PCSK9 and particularly human PCSK9. Protein-specific antagonists of PCSK9 (or "PCSK9-specific antagonists") in accordance herewith are effective in the inhibition of PCSK9 function and, thus, are of import in the treatment of conditions associated with/impacted by PCSK9 function, including, but not limited to, hypercholesterolemia, coronary heart disease, metabolic syndrome, acute coronary syndrome and related conditions. Reference herein to PCSK9 function or PCSK9 activity refers to any activity/function that requires, or is exacerbated or enhanced by PCSK9. PCSK9-specific antagonists have been demonstrated herein to be particularly effective for counteracting PCSK9-dependent inhibition of cellular LDL-uptake. Repeatedly, disclosed antagonists demonstrated dose-dependent inhibition of the effects of PCSK9 on LDL uptake.

PCSK9-specific antagonists as disclosed herein are, therefore, desirable molecules for lowering plasma LDL cholesterol levels. PCSK9-specific antagonists are of utility for any primate, mammal or vertebrate of commercial or domestic veterinary importance. PCSK9-specific antagonists are of utility as well for any population of cells or tissues possessing the LDL receptor. Means for measuring LDL uptake and, thus, various effects thereon are described in the literature; see, e.g., Barak & Webb, 1981 *J. Cell Biol.* 90:595-604, and Stephan & Yurachek, 1993 *J. Lipid Res.* 34:325330. In addition, means for measuring LDL cholesterol in plasma is well described in the literature; see, e.g., McNamara et al., 2006 *Clinica Chimica Acta* 369:158-167.

PSCK9-specific antagonists also have utility for various diagnostic purposes in the detection and quantification of PCSK9.

PCSK9-specific antagonists as defined herein selectively recognize and specifically bind to PCSK9. Use of the terms "selective" or "specific" herein refers to the fact that the disclosed antagonists do not show significant binding to other than PSCK9, except in those specific instances where the antagonist is supplemented to confer an additional, distinct specificity to the PCSK9-specific binding portion (as, for example, in bispecific or bifunctional molecules where the molecule is designed to bind or effect two functions, at least one of which is to specifically bind PCSK9). In specific embodiments, PCSK9-specific antagonists bind to human PCSK9 with a KD of $1.2 \times 10^{-6}$ or less. In specific embodiments, PCSK9-specific antagonists bind to human PCSK9 with a KD of $5 \times 10^{-7}$ or less, of $2 \times 10^{-7}$ or less, or of $1 \times 10^{-7}$ or less. In additional embodiments, PCSK9-specific antagonists bind to human PCSK9 with a KD of $1 \times 10^{-8}$ or less. In other embodiments, PCSK9-specific antagonists bind to human PCSK9 with a KD of $5 \times 10^{-9}$ or less, or of $1 \times 10^{-9}$ or less. In further embodiments, PCSK9-specific antagonists bind to human PCSK9 with a KD of $1 \times 10^{-10}$ or less, a KD of $1 \times 10^{-11}$ or less, or a KD of $1 \times 10^{-12}$ or less. In specific embodiments, PCSK9-specific antagonists do not bind other proteins at the above KDs. KD refers to the dissociation constant obtained from the ratio of Kd (the dissociation rate of a particular binding molecule-target protein interaction) to Ka (the association rate of the particular binding molecule-target protein interaction), or Kd/Ka which is expressed as a molar concentration (M). KD values can be determined using methods well established in the art. A preferred method for determining the KD of a binding molecule is by using surface plasmon resonance, for example a biosensor system such as a Biacore™ (GE Healthcare Life Sciences) system.

PCSK9-specific antagonists have been shown to dose-dependently inhibit PCSK9 dependent effects on LDL uptake. Accordingly, PCSK9-specific antagonists are characterized by their ability to counteract PCSK9-dependent inhibition of LDL uptake into cells. This uptake of LDL into cells by the LDL receptor is referred to herein as "cellular LDL uptake". In specific embodiments, PCSK9-specific antagonists antagonize PCSK9-dependent inhibition of LDL uptake into cells, exhibiting an IC50 of $1.2 \times 10^{-6}$ or less. In specific embodiments, PCSK9-specific antagonists antagonize PCSK9-dependent inhibition of LDL uptake into cells, exhibiting a KD of $5 \times 10^{-7}$ or less, of $2 \times 10^{-7}$ or less, or of $1 \times 10^{-7}$ or less. In additional embodiments, PCSK9-specific antagonists antagonize PCSK9-dependent inhibition of LDL uptake into cells, exhibiting an IC50 of $1 \times 10^{-8}$ or less. In other embodiments, PCSK9-specific antagonists antagonize PCSK9-dependent inhibition of LDL uptake into cells, exhibiting an IC50 of $5 \times 10^{-9}$ or less, of $2 \times 10^{-9}$ or less, or of $1 \times 10^{-9}$ or less. In further embodiments, PCSK9-specific antagonists antagonize PCSK9-dependent inhibition of LDL uptake into cells, exhibiting an IC50 of $1 \times 10^{-10}$ or less, a KD of $1 \times 10^{-11}$ or less, or a KD of $1 \times 10^{-12}$ or less. The extent of inhibition by any PCSK9-specific antagonist may be measured quantitatively in statistical comparison to a control, or via any alternative method available in the art for assessing a negative effect on, or inhibition of, PCSK9 function (i.e., any method capable of assessing antagonism of PCSK9 function). In specific embodiments, the inhibition is at least about 10% inhibition. In other embodiments, the inhibition is at least 20%, 30%, 40%, 50%, 60%, 70,%, 80%, 90%, or 95%.

A PCSK9-specific antagonist in accordance herewith can be any binding molecule with specificity for PCSK9 protein including, but not limited to, antibody molecules as defined below, any PCSK9-specific binding structure, any polypeptide or nucleic acid structure that specifically binds PCSK9, and any of the foregoing incorporated into various protein scaffolds; including but not limited to, various non-antibody-based scaffolds, and various structures capable of affording selective binding to PCSK9 including but not limited to small modular immunopharmaceuticals (or "SMIPs"; see, Haan & Maggos, 2004 *Biocentury January* 26); Immunity proteins (see, e.g., Chak et al., 1996 *Proc. Natl. Acad. Sci. USA* 93:6437-6442); cytochrome b562 (see Ku and Schultz, 1995 *Proc. Natl. Acad. Sci. USA* 92:6552-6556); the peptide α2p8 (see Barthe et al., 2000 *Protein Sci.* 9:942-955); avimers (Avidia; see Silverman et al., 2005 *Nat. Biotechnol.* 23:1556-1561); DARPins (Molecular Partners; see Binz et al., 2003 *J. Mol. Biol.* 332:489-503; and Forrer et al., 2003 *FEBS Lett.* 539:2-6); Tetranectins (see, Kastrup et al., 1998 *Acta. Crystallogr. D. Biol. Crystallogr.* 54:757-766); Adnectins (Adnexus; see, Xu et al., 2002 *Chem. Biol.* 9:933-942), Anticalins (Pieris; see Vogt & Skerra, 2004 *Chemobiochem.* 5:191-199; Beste et al., 1999 *Proc. Natl. Acad. Sci. USA* 96:1898-1903; Lamla & Erdmann, 2003 *J. Mol. Biol.* 329:381-388; and Lamla & Erdmann, 2004 *Protein Expr. Purif.* 33:39-47); A-domain proteins (see North & Blacklow, 1999 *Biochemistry* 38:3926-3935), Lipocalins (see Schlehuber & Skerra, 2005 *Drug Discov. Today* 10:23-33); Repeat-motif proteins such as Ankyrin repeat proteins (see Sedgwick & Smerdon, 1999 *Trends Biochem. Sci.* 24:311-316; Mosavi et al., 2002 *Proc. Natl. Acad. Sci. USA* 99:16029-16034; and Binz et al., 2004 *Nat. Biotechnol.* 22:575-582); Insect Defensin A (see Zhao et al., 2004 *Peptides* 25:629-635); Kunitz domains (see Roberts et al., 1992 *Proc. Natl. Acad. Sci. USA* 89:2429-2433; Roberts et al., 1992 *Gene* 121:9-15; Dennis & Lazarus, 1994 *J. Biol. Chem.* 269:22129-22136; and Dennis & Lazarus, 1994 *J. Biol. Chem.* 269:22137-22144); PDZ-Domains (see Schneider et al., 1999 *Nat. Biotechnol.* 17:170-175); Scorpion toxins such as Charybdotoxin (see Vita et al., 1998 *Biopolymers* 47:93-100); $10^{th}$ fibronectin type III domain (or 10Fn3; see Koide et al., 1998 *J. Mol. Biol.* 284:1141-1151, and Xu et al., 2002 *Chem. Biol.* 9:933-942); CTLA-4 (extracellular domain; see Nuttall et al., 1999 *Proteins* 36:217-227; and Irving et al., 2001 *J. Immunol. Methods* 248:31-45); Knottins (see Souriau et al., 2005 *Biochemistry* 44:7143-7155 and Lehtio et al., 2000 *Proteins* 41:316-322); Neocarzinostatin (see Heyd et al. 2003 *Biochemistry* 42:5674-5683); carbohydrate binding module 4-2 (CBM4-2; see Cicortas et al., 2004 *Protein Eng. Des. Sel.* 17:213-221); Tendamistat (see McConnell & Hoess, 1995 *J. Mol. Biol.* 250:460-470, and Li et al., 2003 *Protein Eng.* 16:65-72); T cell receptor (see Holler et al., 2000 *Proc. Natl. Acad. Sci. USA* 97:5387-5392; Shusta et al., 2000 *Nat. Biotechnol.* 18:754-759; and Li et al., 2005 *Nat. Biotechnol.* 23:349-354); Affibodies (Affibody; see Nord et al., 1995 *Protein Eng.* 8:601-608; Nord et al., 1997 *Nat. Biotechnol.* 15:772-777; Gunneriusson et al., 1999 *Protein Eng.* 12:873-878); and other selective binding proteins or scaffolds recognized in the literature; see, e.g., Binz & Plückthun, 2005 *Curr. Opin. Biotech.* 16:1-11; Gill & Damle, 2006 *Curr. Opin. Biotechnol.* 17:1-6; Hosse et al., 2006 *Protein Science* 15:14-27; Binz et al., 2005 *Nat. Biotechnol.* 23:1257-1268; Hey et al., 2005 *Trends in Biotechnol.* 23:514-522; Binz & Plückthun, 2005 *Curr. Opin. Biotech.* 16:459-469; Nygren & Skerra, 2004 *J. Immunolog. Methods* 290:3-28; Nygren & Uhlen, 1997 *Curr. Opin. Struct. Biol.* 7:463-469. Accordingly, non-antibody-based scaffolds or antagonist molecules with selectivity for PCSK9 that counteract PCSK9-dependent inhibition of cellular LDL-uptake form important embodiments of the present invention. Aptamers (nucleic acid or peptide molecules capable of selectively binding a target molecule) are one specific example. They can be selected from random sequence pools or identified from natural sources such as riboswitches. Peptide aptamers, nucleic acid aptamers (e.g., structured nucleic acid, including both DNA and RNA-based structures) and nucleic acid decoys can be effective for selectively binding and inhibiting proteins of interest; see, e.g., Hoppe-Seyler & Butz, 2000 *j. Mol. Med.* 78:426-430; Bock et al., 1992 *Nature* 355:564-566; Bunka & Stockley, 2006 *Nat. Rev. Microbiol.* 4:588-596; Martell et al., 2002 *Molec. Ther.* 6:30-34; Jayasena, 1999 *Clin. Chem.* 45:1628-1650.

Expression and selection of various PCSK9-specific antagonists may be achieved using suitable technologies including, but not limited to phage display (see, e.g., International Application Number WO 92/01047, Kay et al., 1996 *Phage Display of Peptides and Proteins: A Laboratory Manual*, San Diego: Academic Press), yeast display, bacterial display, T7 display, and ribosome display (see, e.g., Lowe & Jermutus, 2004 *Curr. Pharm. Biotech.* 517-527).

"Antibody molecule" or "Antibody" as described herein refers to an immunoglobulin-derived structure with selective binding to PCSK9 including, but not limited to, a full length or whole antibody, an antigen binding fragment (a fragment derived, physically or conceptually, from an antibody structure), a derivative of any of the foregoing, a chimeric molecule, a fusion of any of the foregoing with another polypeptide, or any alternative structure/composition which incorporates any of the foregoing for purposes of selectively binding/inhibiting the function of PCSK9. "Whole" antibodies or "full length" antibodies refer to proteins that comprise two heavy (H) and two light (L) chains inter-connected by disulfide bonds which comprise: (1) in terms of the heavy chains, a variable region (abbreviated herein as "$V_H$") and a heavy chain constant region which comprises three domains, $C_{H1}$, $C_{H2}$, and $C_{H3}$; and (2) in terms of the light chains, a light chain variable region (abbreviated herein as "$V_L$") and a light chain constant region which comprises one domain, $C_L$.

"Isolated" as used herein describes a property as it pertains to the disclosed PCSK9-specific antagonists, nucleic acid or other that makes them different from that found in nature. The difference can be, for example, that they are of a different purity than that found in nature, or that they are of a different structure or form part of a different structure than that found in nature. A structure not found in nature, for example, includes recombinant human immunoglobulin structures including, but not limited to, recombinant human immunoglobulin structures with optimized CDRs. Other examples of structures not found in nature are PCSK9-specific antagonists or nucleic acid substantially free of other cellular material. Isolated PCSK9-specific antagonists are generally free of other protein-specific antagonists having different protein specificities (i.e., possess an affinity for other than PCSK9).

Antibody fragments and, more specifically, antigen binding fragments are molecules possessing an antibody variable region or segment thereof (which comprises one or more of the disclosed CDR 3 domains, heavy and/or light), which confers selective binding to PCSK9, and particularly human PCSK9. Antibody fragments containing such an antibody variable region include, but are not limited to the following antibody molecules: a Fab, a F(ab')$_2$, a Fd, a Fv, a scFv, bispecific antibody molecules (antibody molecules comprising a PCSK9-specific antibody or antigen binding fragment as disclosed herein linked to a second functional moiety having a different binding specificity than the antibody, including, without limitation, another peptide or protein such as an antibody, or receptor ligand), a bispecific single chain Fv dimer, an isolated CDR3, a minibody, a 'scAb', a dAb fragment, a diabody, a triabody, a tetrabody, a minibody, and artificial antibodies based upon protein scaffolds, including but not limited to fibronectin type III polypeptide antibodies (see, e.g., U.S. Pat. No. 6,703,199 and International Application Numbers WO 02/32925 and WO 00/34784) or cytochrome B; see, e.g., Nygren et al., 1997 *Curr. Opinion Struct. Biol.* 7:463-469. The antibody portions or binding fragments may be natural, or partly or wholly synthetically produced. Such antibody portions can be prepared by various means known by one of skill in the art, including, but not limited to, conventional techniques, such as papain or pepsin digestion.

The present invention provides, in one particular aspect, isolated PCSK9-specific antagonists which antagonize PCSK9 function. In particular embodiments, said PCSK9-specific antagonists inhibit PCSK9's antagonism of cellular LDL uptake. Disclosed PCSK9-specific antagonists effectively antagonize PCSK's inhibition of LDL uptake and thus, form desirable molecules for lowering plasma LDL-cholesterol levels; see, e.g., Cohen et al., 2005 *Nat. Genet.* 37:161-165 (wherein significantly lower plasma LDL cholesterol levels were noted in individuals heterozygous for a nonsense mutation in allele PCSK9); Rashid et al., 2005 *Proc. Natl. Acad. Sci. USA* 102:5374-5379 (wherein PCSK9-knockout mice evidenced increased numbers of LDLRs in hepatocytes, accelerated plasma LDL clearance, and significantly lower plasma cholesterol levels); and Cohen et al., 2006 *N. Engl. J. Med.* 354:1264-1272 (wherein humans heterozygous for mutated, loss of function, PCSK9 exhibited a significant reduction in the long-term risk of developing atherosclerotic heart disease).

Through repeat experiments, five PCSK9-specific antagonists, namely antibody molecules 1CX1G08, 3BX5C01, 3CX2A06, 3CX3D02, and 3CX4B08 dose-dependently inhibited the effects of PCSK9 on LDL uptake. In specific embodiments, the present invention, thus, encompasses PCSK9-specific antagonists and, in more specific embodiments, antibody molecules comprising the heavy and/or light chain variable regions contained within these antibody molecules, as well as equivalents (characterized as having one or more conservative amino acid substitutions) or homologs thereof. Particular embodiments comprise isolated PCSK9-specific antagonists that comprise the CDR domains disclosed herein or sets of heavy and/or light chain CDR domains disclosed herein, or equivalents thereof, characterized as having one or more conservative amino acid substitutions. Use of the terms "domain" or "region" herein simply refers to the respective portion of the antibody molecule wherein the sequence or segment at issue will reside or, in the alternative, currently resides.

In specific embodiments, the present invention provides isolated PCSK9-specific antagonists and, in more specific embodiments, antibody molecules comprising a heavy chain variable region selected from the group consisting of: SEQ ID NO: 11, SEQ ID NO: 27, SEQ ID NO: 45, SEQ ID NO: 61 and SEQ ID NO: 79, equivalents thereof characterized as having one or more conservative amino acid substitutions, and homologs thereof. The disclosed antagonists should inhibit PCSK9-dependent inhibition of cellular LDL uptake. In specific embodiments, the present invention provides homologs of the disclosed antagonists characterized as being at least 90% homologous to antagonists disclosed herein; said antagonists which inhibit PCSK9-dependent inhibition of cellular LDL uptake.

In specific embodiments, the present invention provides isolated PCSK9-specific antagonists and, in more specific embodiments, antibody molecules comprising a light chain variable region selected from the group consisting of: SEQ ID NO: 93, SEQ ID NO: 95, SEQ ID NO: 97, SEQ ID NO: 99 and SEQ ID NO: 101; equivalents thereof characterized as having one or more conservative amino acid substitutions, and homologs thereof. The disclosed antagonists should inhibit PCSK9-dependent inhibition of cellular LDL uptake. In specific embodiments, the present invention provides homologs of the disclosed antagonists characterized as being at least 90% homologous to antagonists disclosed herein; said antagonists which inhibit PCSK9-dependent inhibition of cellular LDL uptake.

In specific embodiments, the present invention provides isolated PCSK9-specific antagonists and, in more specific embodiments, antibody molecules which comprise: (i) a heavy chain variable region comprising SEQ ID NO: 11 and a light chain variable region comprising SEQ ID NO: 93, (ii) a heavy chain variable region comprising SEQ ID NO: 27 and a light chain variable region comprising SEQ ID NO: 95, (iii) a heavy chain variable region comprising SEQ ID NO: 45 and a light chain variable region comprising SEQ ID NO: 97, (iv) a heavy chain variable region comprising SEQ ID NO: 61 and a light chain variable region comprising SEQ ID NO: 99, (v) a heavy chain variable region comprising SEQ ID NO: 79 and a light chain variable region comprising SEQ ID NO: 101; or equivalent of any of the foregoing antibody molecules characterized as having one or more conservative amino acid substitutions in the prescribed sequences. Specific embodiments are said antagonists which inhibit PCSK9-dependent inhibition of cellular LDL uptake.

In particular embodiments, the present invention provides isolated PCSK9-specific antagonists and, in more specific embodiments, PCSK9 antibody molecules that comprise variable heavy CDR3 sequence selected from the group consisting of: SEQ ID NO: 17, SEQ ID NO: 33, SEQ ID NO: 51, SEQ ID NO: 67 and SEQ ID NO: 85; and conservative modifications thereof; specific embodiments of which inhibit PCSK9-dependent inhibition of cellular LDL uptake. Specific embodiments provide isolated antagonists which comprise a heavy chain variable region wherein CDR1, CDR2, and/or CDR3 sequences comprise (i) SEQ ID NO: 13, SEQ ID NO: 15 and/or SEQ ID NO: 17, respectively, (ii) SEQ ID NO: 29, SEQ ID NO: 31 and/or SEQ ID NO: 33, respectively, (iii) SEQ ID NO: 47, SEQ ID NO: 49 and/or SEQ ID NO: 51, respectively, (iv) SEQ ID NO: 63, SEQ ID NO: 65 and/or SEQ ID NO: 67, respectively, (v) SEQ ID NO: 81, SEQ ID NO: 83 and/or SEQ ID NO: 85, respectively; or equivalents thereof characterized as having one or more conservative amino acid substitutions in any one or more of the CDR sequences.

In particular embodiments, the present invention provides isolated PCSK9-specific antagonists and, in more specific embodiments, antibody molecules which comprise variable light CDR3 sequence selected from the group consisting of: SEQ ID NO: 7, SEQ ID NO: 23, SEQ ID NO: 41, SEQ ID NO: 57 and SEQ ID NO: 75; and conservative modifications thereof; specific embodiments of which inhibit PCSK9-dependent inhibition of cellular LDL uptake. Specific embodiments provide isolated antagonists which comprise a light chain variable region wherein CDR1, CDR2, and/or CDR3 sequences comprise (i) SEQ ID NO: 3, SEQ ID NO: 5, and/or SEQ ID NO: 7, respectively, (ii) SEQ ID NO: 21, SEQ ID NO: 5 and/or SEQ ID NO: 23, respectively, (iii) SEQ ID NO: 37, SEQ ID NO: 39 and/or SEQ ID NO: 41, respectively, (iv) SEQ ID NO: 55, SEQ ID NO: 39 and/or SEQ ID NO: 57, respectively, (v) SEQ ID NO: 71, SEQ ID NO: 73 and/or SEQ ID NO: 75, respectively; or an equivalent thereof characterized as having one or more conservative amino acid substitutions in any one or more of the CDR sequences.

In particular embodiments, the present invention provides isolated PCSK9-specific antagonists and, in more specific embodiments, antibody molecules which comprise heavy chain variable region CDR3 sequence and light chain variable region CDR3 sequence comprising (i) SEQ ID NOs: 17 and 7, respectively, (ii) SEQ ID NOs: 33 and 23, respectively, (iii) SEQ ID NOs: 51 and 41, respectively, (iv) SEQ ID NOs: 67 and 57, respectively, and (v) SEQ ID NOs: 85 and 75, respectively; or conservative modifications thereof in any one or more of the CDR3 sequences; specific embodiments of which inhibit PCSK9-dependent inhibition of cellular LDL uptake.

Specific embodiments provide isolated PCSK9-specific antagonists and, in more specific embodiments, antibody molecules which comprise heavy chain variable region CDR1, CDR2, and CDR3 sequences and light chain variable region CDR1, CDR2, and CDR3 sequences comprising (i) SEQ ID NOs: 13, 15, 17, 3, 5 and 7, respectively, (ii) SEQ ID NOs: 29, 31, 33, 21, 5 and 23, respectively, (iii) SEQ ID NOs: 47, 49, 51, 37, 39 and 41, respectively, (iv) SEQ ID NOs: 63, 65, 67, 55, 39 and 57, respectively, and (v) SEQ ID NOs: 81, 83, 85, 71, 73 and 75, respectively; and equivalents thereof characterized as having one or more conservative amino acid substitutions in any one or more of the CDR sequences; specific embodiments of which inhibit PCSK9-dependent inhibition of cellular LDL uptake.

Conservative amino acid substitutions, as one of ordinary skill in the art will appreciate, are substitutions that replace an amino acid residue with one imparting similar or better (for the intended purpose) functional and/or chemical characteristics. For example, conservative amino acid substitutions are often ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Such modifications are not designed to significantly reduce or alter the binding or functional inhibition characteristics of the PCSK9-specific antagonist, albeit they may improve such properties. The purpose for making a substitution is not significant and can include, but is by no means limited to, replacing a residue with one better able to maintain or enhance the structure of the molecule, the charge or hydrophobicity of the molecule, or the size of the molecule. For instance, one may desire simply to substitute a less desired residue with one of the same polarity or charge. Such modifications can be introduced by standard techniques known in the art, such as site-directed mutagenesis and PCR-mediated mutagenesis. One specific means by which those of skill in the art accomplish conservative amino acid substitutions is alanine scanning mutagenesis as discussed in, for example, MacLennan et al., 1998 *Acta Physiol. Scand. Suppl.* 643:55-67, and Sasaki et al., 1998 *Adv. Biophys.* 35:1-24. The altered antagonists are then tested for retained or better function using functional assays available in the art or described herein. PCSK9-specific antagonists possessing one or more such conservative amino acid substitutions which retain the ability to selectively bind to human PCSK9 and antagonize PCSK9 functioning at a level the same or better than the molecule not possessing such amino acid alterations are referred to herein as "functional equivalents" of the disclosed antagonists and form specific embodiments of the present invention.

In another aspect, the present invention provides isolated PCSK9-specific antagonists and, in more specific embodiments, antibody molecules which comprise heavy and/or light chain variable regions comprising amino acid sequences that are homologous to the corresponding amino acid sequences of the disclosed antibodies, wherein the antibody molecules inhibit PCSK9-dependent inhibition of cellular LDL uptake. Specific embodiments are antagonists which comprise heavy and/or light chain variable regions which are at least 90% homologous to disclosed heavy and/or light chain variable regions, respectively. Reference to "at least 90% homologous" includes at least 90, 91, 92, 93, 94, 95, 96, 97, 98, 99 and 100% homologous sequences.

PCSK9-specific antagonists with amino acid sequences homologous to the amino acid sequences of antagonists described herein are typically produced to improve one or more of the properties of the antagonist without changing its specificity for PCSK9. One method of obtaining such sequences, which is not the only method available to the skilled artisan, is to mutate sequence encoding the PCSK9-specific antagonist or specificity-determining region(s) thereof, express an antagonist comprising the mutated sequence(s), and test the encoded antagonist for retained function using available functional assays including those described herein. Mutation may be by site-directed or random mutagenesis. As one of skill in the art will appreciate, however, other methods of mutagenesis can readily bring about the same effect. For example, in certain methods, the spectrum of mutants are constrained by non-randomly targeting conservative substitutions based on either amino acid chemical or structural characteristics, or else by protein structural considerations. In affinity maturation experiments, several such mutations may be found in a single selected molecule, whether they are randomly or non-randomly selected. There are also various structure-based approaches toward affinity maturation as demonstrated in, e.g., U.S. Pat. No. 7,117,096, PCT Pub. Nos.: WO 02/084277 and WO 03/099999.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and length of each gap, which need to be introduced for optimal alignment of the two sequences. The comparison of sequences and determination of percent identity between sequences can be determined using methods generally known to those in the art and can be accomplished using a mathematical algorithm. For example, the percent identity between amino acid sequences and/or nucleotide sequences can be determined using the algorithm of Meyers and Miller, 1988 *Comput. Appl. Biosci.* 4:11-17, which has been incorporated into the ALIGN program (version 2.0). In addition, the percent identity between amino acid sequences or nucleotide sequences can be determined using the GAP program in the GCG software package available online from Accelrys, using its default parameters.

In one aspect, the present invention provides isolated PCSK9-specific antibody molecules for human PCSK9 which have therein at least one light chain variable domain and at least one heavy chain variable domain (VL and VH, respectively).

Manipulation of protein-specific molecules to produce other binding molecules with similar or better specificity is well within the realm of one skilled in the art. This can be accomplished, for example, using techniques of recombinant DNA technology. One specific example of this involves the introduction of DNA encoding the immunoglobulin variable region, or one or more of the CDRs, of an antibody to the variable region, constant region, or constant region plus framework regions, as appropriate, of a different immunoglobulin. Such molecules form important aspects of the present invention. Specific immunoglobulins, into which particular disclosed sequences may be inserted or, in the alternative, form the essential part of, include but are not limited to the following antibody molecules which form particular embodiments of the present invention: a Fab (monovalent fragment with variable light (VL), variable heavy (VH), constant light (CL) and constant heavy 1 (CH1) domains), a F(ab')$_2$ (bivalent fragment comprising two Fab fragments linked by a disulfide bridge or alternative at the hinge region), a Fd (VH and CH1 domains), a Fv (VL and VH domains), a scFv (a single chain Fv where VL and VH are joined by a linker, e.g., a peptide linker, see, e.g., Bird et al., 1988 *Science* 242:423-426, Huston et al., 1988 *PNAS USA* 85:5879-5883), a bispecific antibody molecule (an antibody molecule comprising a PCSK9-specific antibody or antigen binding fragment as disclosed herein linked to a second functional moiety having a different binding specificity than the antibody, including, without limitation, another peptide or protein such as an antibody, or receptor ligand), a bispecific single chain Fv dimer (see, e.g., PCT/US92/09965), an isolated CDR3, a minibody (single chain-CH3 fusion that self assembles into a bivalent dimer of about 80 kDa), a 'scAb' (an antibody fragment containing VH and VL as well as either CL or CH1), a dAb fragment (VH domain, see, e.g., Ward et al., 1989 *Nature* 341:544-546, and McCafferty et al., 1990 *Nature* 348:552-554; or VL domain; Holt et al., 2003 *Trends in Biotechnology* 21:484-489), a diabody (see, e.g., Holliger et al., 1993 *PNAS USA* 90:6444-6448 and International Application Number WO 94/13804), a triabody, a tetrabody, a minibody (a scFv joined to a CH3; see, e.g., Hu et al., 1996 *Cancer Res.* 56:3055-3061), IgG, IgG1, IgG2, IgG3, IgG4, IgM, IgD, IgA, IgE or any derivatives thereof, and artificial antibodies based upon protein scaffolds, including but not limited to fibronectin type III polypeptide antibodies (see, e.g., U.S. Pat. No. 6,703,199 and International Application Number WO 02/32925) or cytochrome B; see, e.g., Koide et al., 1998 *J. Molec. Biol.* 284:1141-1151, and Nygren et al., 1997 *Current Opinion in Structural Biology* 7:463-469. Certain antibody molecules including, but not limited to, Fv, scFv, diabody molecules or domain antibodies (Domantis) may be stabilized by incorporating disulfide bridges to line the VH and VL domains, see, e.g., Reiter et al., 1996 *Nature Biotech.* 14:1239-1245. Bispecific antibodies may be produced using conventional technologies (see, e.g., Holliger & Winter, 1993 *Current Opinion Biotechnol.* 4:446-449, specific methods of which include production chemically, or from hybrid hybridomas) and other technologies including, but not limited to, the BiTE™ technology (molecules possessing antigen binding regions of different specificity with a peptide linker) and knobs-into-holes engineering (see, e.g., Ridgeway et al., 1996 *Protein Eng.* 9:616-621). Bispecific diabodies may be produced in *E. coli*, and these molecules as other PCSK9-specific antagonists, as one of skill in the art will appreciate, may be selected using phage display in the appropriate libraries (see, e.g., International Application Number WO 94/13804).

Variable domains, into which CDRs of interest are inserted, may be obtained from any germ-line or rearranged human variable domain. Variable domains may also be synthetically produced. The CDR regions can be introduced into the respective variable domains using recombinant DNA technology. One means by which this can be achieved is described in Marks et al., 1992 *Bio/Technology* 10:779-783. A variable heavy domain may be paired with a variable light domain to provide an antigen binding site. In addition, independent regions (e.g., a variable heavy domain alone) may be used to bind antigen. The artisan is well aware, as well, that two domains of an Fv fragment, VL and VH, while perhaps coded by separate genes, may be joined, using recombinant methods, by a synthetic linker that enables them to be made as a single protein chain in which the VL and VH regions pair to form monovalent molecules (scFvs).

Specific embodiments provide the CDR(s) in germline framework regions. Specific embodiments herein provide heavy chain CDR(s) selected from the group consisting of: SEQ ID NO: 17 and SEQ ID NO: 85 into VH3 in place of the relevant CDR(s). Specific embodiments herein provide heavy chain CDR(s) selected from the group consisting of: SEQ ID NO: 33, SEQ ID NO: 51 and SEQ ID NO: 67 into VH5 in place of the relevant CDR(s). Specific embodiments herein provide light chain CDR(s) selected from the group consisting of: SEQ ID NO: 7, SEQ ID NO: 23 and SEQ ID NO: 75 into VL3 in place of the relevant CDR(s). Specific embodiments herein provide light chain CDR(s) selected from the group consisting of: SEQ ID NO: 41 and SEQ ID NO: 57 into VK1 in place of the relevant CDR(s).

Specific embodiments provide antibody molecules as defined herein which comprise a light chain region comprising sequence selected from the group consisting of: SEQ ID NO: 1, SEQ ID NO: 19, SEQ ID NO: 35, SEQ ID NO: 53 and SEQ ID NO: 69. Additional embodiments provide antibody molecules which comprise both a light chain region as described and a heavy chain region comprising sequence selected from the group consisting of SEQ ID NO: 9, SEQ ID NO: 25, SEQ ID NO: 43, SEQ ID NO: 59 and SEQ ID NO: 77.

The present invention encompasses antibody molecules that are human, humanized, deimmunized, chimeric and primatized. The invention also encompasses antibody molecules produced by the process of veneering; see, e.g., Mark et al., 1994 Handbook of Experimental Pharmacology, vol. 113: The pharmacology of monoclonal Antibodies, Springer-Verlag, pp. 105-134. "Human" in reference to the disclosed antibody molecules specifically refers to antibody molecules having variable and/or constant regions derived from human germline immunoglobulin sequences, wherein said sequences may, but need not, be modified/altered to have certain amino acid substitutions or residues that are not encoded by human germline immunoglobulin sequence. Such mutations can be introduced by methods including, but not limited to, random or site-specific mutagenesis in vitro, or by somatic mutation in vivo. Specific examples of mutation techniques discussed in the literature are that disclosed in Gram et al., 1992 *PNAS USA* 89:3576-3580; Barbas et al., 1994 *PNAS USA* 91:3809-3813, and Schier et al., 1996 *J. Mol. Biol.* 263:551-567. These are only specific examples and do not represent the only available techniques. There are a plethora of mutation techniques in the scientific literature which are available to, and widely appreciated by, the skilled artisan. "Humanized" in reference to the disclosed antibody molecules refers specifically to antibody molecules wherein CDR sequences derived from another mammalian species, such as a mouse, are grafted onto human framework sequences. "Primatized" in reference to the disclosed antibody molecules refers to antibody molecules wherein CDR sequences of a non-primate are inserted into primate framework sequences, see, e.g., WO 93/02108 and WO 99/55369.

Specific antibodies of the present invention are monoclonal antibodies and, in particular embodiments, are in one of the following antibody formats: IgD, IgA, IgE, IgM, IgG1, IgG2, IgG3, IgG4 or any derivative of any of the foregoing. The language "derivatives thereof" or "derivatives" in this respect includes, inter alia, (i) antibodies and antibody molecules with modifications in one or both variable regions (i.e., VH and/or VL), (ii) antibodies and antibody molecules with manipulations in the constant regions of VH and/or VL, and (iii) antibodies and antibody molecules that contain additional chemical moieties which are not normally a part of the immunoglobulin molecule (e.g., pegylation).

Manipulations of the variable regions can be within one or more of the VH and/or VL CDR regions. Site-directed mutagenesis, random mutagenesis or other method for generating sequence or molecule diversity can be utilized to create mutants which can subsequently be tested for a particular functional property of interest in available in vitro or in vivo assays including those described herein.

Antibodies of the present invention also include those in which modifications have been made to the framework residues within VH and/or VL to improve one or more properties of the antibody of interest. Typically, such framework modifications are made to decrease the immunogenicity of the antibody. For example, one approach is to "backmutate" one or more framework residues to the corresponding germ line sequence. More specifically, an antibody that has undergone somatic mutation may contain framework residues that differ from the germline sequence from which the antibody is derived. Such residues can be identified by comparing the antibody framework sequences to the germline sequences from which the antibody is derived. Such "backmutated" antibodies are also intended to be encompassed by the invention. Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, where present, typically to alter one or more functional properties of the antibody, such as serum half-life, complement fixation, Fc receptor binding, and/or antigen-dependent cellular cytotoxicity.

The concept of generating "hybrids" or "combinatorial" IgG forms comprising various antibody isotypes to hone in on desired effector functionality has generally been described; see, e.g., Tao et al., 1991 *J. Exp. Med.* 173:1025-1028. A specific embodiment of the present invention encompasses antibody molecules that possess specific manipulations in the Fc region which have been found to result in reduced binding to FcγR receptors or C1q on the part of the antibody. The present invention, therefore, encompasses antibodies in accordance with the present description that do not provoke (or provoke to a lesser extent) antibody-dependent cellular cytotoxicity ("ADCC"), complement-mediated cytotoxicity ("CMC"), or form immune complexes, while retaining normal pharmacokinetic ("PK") properties. Specific embodiments of the present invention provide an antibody molecule as defined in accordance with the present invention which comprises, as part of its immunoglobulin structure, SEQ ID NO: 87. FIG. 6 illustrates a comparison of sequence comprising SEQ ID NO: 87, particularly IgG2 m4, with IgG1, IgG2, and IgG4.

Specific PCSK9-specific antagonists may carry a detectable label, or may be conjugated to a toxin (e.g., a cytotoxin), a radioactive isotope, a radionuclide, a liposome, a targeting moiety, a biosensor, a cationic tail, or an enzyme (e.g., via a peptidyl bond or linker). Such PCSK9-specific antagonist compositions form an additional aspect of the present invention.

In another aspect, the present invention provides isolated nucleic acid encoding disclosed PCSK9-specific antagonists. The nucleic acid may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, for example, using standard techniques, including without limitation, alkaline/SDS treatment, CsCl banding, column chromatography, agarose gel electrophoresis and other suitable methods known in the art. The nucleic acid may include DNA (inclusive of cDNA) and/or RNA. Nucleic acids of the present invention can be obtained using standard molecular biology techniques. For antibodies expressed by hybridomas (e.g., hybridomas prepared from transgenic mice carrying human immunoglobulin genes), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

The present invention encompasses isolated nucleic acid encoding disclosed variable heavy and/or light chains and select components thereof, particularly the disclosed respective CDR3 regions. In specific embodiments hereof, the CDR (s) are provided within antibody framework regions. Specific embodiments provide isolated nucleic acid encoding the CDR(s) into germline framework regions. Specific embodiments herein provide isolated nucleic acid encoding heavy chain CDR(s) SEQ ID NOs: 18 or 86 into VH3 in place of the nucleic acid encoding the relevant CDR(s). Specific embodiments herein provide isolated nucleic acid encoding heavy chain CDR(s) SEQ ID NOs: 34, 52 or 68 into VH5 in place of the nucleic acid encoding the relevant CDR(s). Specific embodiments herein provide isolated nucleic encoding light chain CDR(s) SEQ ID NOs: 8, 24, or 76 into VL3 in place of the nucleic acid encoding the relevant CDR(s). Specific embodiments herein provide isolated nucleic encoding light chain CDR(s) SEQ ID NOs: 42 or 58 into VK1 in place of the nucleic acid encoding the relevant CDR(s). The isolated nucleic acid encoding the variable regions can be provided within any desired antibody molecule format including, but not limited to, the following: F(ab')$_2$, a Fab, a Fv, a scFv, bispecific antibody molecules (antibody molecules comprising a PCSK9-specific antibody or antigen binding fragment as disclosed herein linked to a second functional moiety having a different binding specificity than the antibody, including, without limitation, another peptide or protein such as an antibody, or receptor ligand), a bispecific single chain Fv dimer, a minibody, a dAb fragment, diabody, triabody or tetrabody, a minibody, IgG, IgG1, IgG2, IgG3, IgG4, IgM, IgD, IgA, IgE or any derivatives thereof.

Specific embodiments provide isolated nucleic acid which encodes antibody molecules as defined herein which comprise a light chain region comprising sequence selected from the group consisting of: SEQ ID NO: 1, SEQ ID NO: 19, SEQ ID NO: 35, SEQ ID NO: 53 and SEQ ID NO: 69. Particular embodiments comprise nucleic acid selected from the group consisting of: SEQ ID NO: 2, SEQ ID NO: 20, SEQ ID NO: 36, SEQ ID NO: 54 and SEQ ID NO: 70. Additional embodiments provide antibody molecules which comprise both a light chain region as described and a heavy chain region comprising sequence selected from the group consisting of: SEQ ID NO: 9, SEQ ID NO: 25, SEQ ID NO: 43, SEQ ID NO: 59 and SEQ ID NO: 77. The nucleic acid sequence encoding the heavy chain region may in specific embodiments comprise sequence selected from the group consisting of: SEQ ID NO: 10, SEQ ID NO: 26, SEQ ID NO: 44, SEQ ID NO: 60 and SEQ ID NO: 78.

Specific embodiments provide isolated nucleic acid which encodes antibody molecules comprising a heavy chain variable domain selected from the group consisting of: SEQ ID NO: 11, SEQ ID NO: 27, SEQ ID NO: 45, SEQ ID NO: 61 and SEQ ID NO: 79; specific embodiments of which comprise nucleic acid sequence SEQ ID NO: 12, SEQ ID NO: 28, SEQ ID NO: 46, SEQ ID NO: 62 or SEQ ID NO: 80, respectively. Specific embodiments of the present invention provide isolated nucleic acid encoding antibody molecules, which comprises: (i) heavy chain CDR1 nucleotide sequence SEQ ID NO: 14, (ii) heavy chain CDR2 nucleotide sequence SEQ ID NO: 16, and/or (iii) heavy chain CDR3 nucleotide sequence SEQ ID NO: 18. Specific embodiments of the present invention provide isolated nucleic acid encoding antibody molecules, which comprises: (i) heavy chain CDR1 nucleotide sequence SEQ ID NO: 30, (ii) heavy chain CDR2 nucleotide sequence SEQ ID NO: 32, and/or (iii) heavy chain CDR3 nucleotide sequence SEQ ID NO: 34. Specific embodiments of the present invention provide isolated nucleic acid encoding antibody molecules, which comprises: (i) heavy chain CDR1 nucleotide sequence SEQ ID NO: 48, (ii) heavy chain CDR2 nucleotide sequence SEQ ID NO: 50, and/or (iii) heavy chain CDR3 nucleotide sequence SEQ ID NO: 52. Specific embodiments of the present invention provide isolated nucleic acid encoding antibody molecules, which comprises: (i) heavy chain CDR1 nucleotide sequence SEQ ID NO: 64, (ii) heavy chain CDR2 nucleotide sequence SEQ ID NO: 66, and/or (iii) heavy chain CDR3 nucleotide sequence SEQ ID NO: 68. Specific embodiments of the present invention provide isolated nucleic acid encoding antibody molecules, which comprises: (i) heavy chain CDR1 nucleotide sequence SEQ ID NO: 82, (ii) heavy chain CDR2 nucleotide sequence SEQ ID NO: 84, and/or (iii) heavy chain CDR3 nucleotide sequence SEQ ID NO: 86. Specific embodiments provide isolated nucleic acid encoding antibody molecules comprising a light chain variable domain selected from the group consisting of: SEQ ID NO: 93, SEQ ID NO: 95, SEQ ID NO: 97, SEQ ID NO: 99 and SEQ ID NO: 101; specific embodiments of which comprise nucleic acid sequence SEQ ID NO: 94, SEQ ID NO: 96, SEQ ID NO: 98, SEQ ID NO: 100, or SEQ ID NO: 102, respectively. Specific embodiments of the present invention provide isolated nucleic acid encoding antibody molecules, which comprises: (i) light chain CDR1 nucleotide sequence SEQ ID NO: 4, (ii) light chain CDR2 nucleotide sequence SEQ ID NO: 6, and/or (iii) light chain CDR3 nucleotide sequence SEQ ID NO: 8. Specific embodiments of the present invention provide isolated nucleic acid encoding antibody molecules, which comprises: (i) light chain CDR1 nucleotide sequence SEQ ID NO: 22, (ii) light chain CDR2 nucleotide sequence SEQ ID NO: 6, and/or (iii) light chain CDR3 nucleotide sequence SEQ ID NO: 24. Specific embodiments of the present invention provide isolated nucleic acid encoding antibody molecules, which comprises: (i) light chain CDR1 nucleotide sequence SEQ ID NO: 38, (ii) light chain CDR2 nucleotide sequence SEQ ID NO: 40, and/or (iii) light chain CDR3 nucleotide sequence SEQ ID NO: 42. Specific embodiments of the present invention provide isolated nucleic acid encoding antibody molecules, which comprises: (i) light chain CDR1 nucleotide sequence SEQ ID NO: 56, (ii) light chain CDR2 nucleotide sequence SEQ ID NO: 40, and/or (iii) light chain CDR3 nucleotide sequence SEQ ID NO: 58. Specific embodiments of the present invention provide isolated nucleic acid encoding antibody molecules, which comprises: (i) light chain CDR1 nucleotide sequence SEQ ID NO: 72, (ii) light chain CDR2 nucleotide sequence SEQ ID NO: 74, and/or (iii) light chain CDR3 nucleotide sequence SEQ ID NO: 76. Specific embodiments of the present invention encompass nucleic acid encoding antibody molecules that possess manipulations in the Fc region which result in reduced binding to FcγR receptors or C1q on the part of the antibody. One specific embodiment of the present invention is isolated nucleic acid which comprises SEQ ID NO: 88. In specific embodiments, synthetic PCSK9-specific antagonists can be produced by expression from nucleic acid generated from oligonucleotides synthesized and assembled within suitable expression vectors; see, e.g., Knappick et al., 2000 *J. Mol. Biol.* 296:57-86, and Krebs et al., 2001 *J. Immunol. Methods* 254:67-84.

Also included within the present invention are isolated nucleic acids comprising nucleotide sequences which are at least about 90% identical and more preferably at least about 95% identical to nucleotide sequences described herein, and which nucleotide sequences encode PCSK9-specific antagonists which inhibit PCSK9-dependent inhibition of cellular LDL uptake. Sequence comparison methods to determine identity are known to those skilled in the art and include those discussed earlier. Reference to "at least about 90% identical" includes at least about 90, 91, 92, 93, 94, 95, 96, 97, 98, 99 or 100% identical.

The invention further provides isolated nucleic acid which hybridizes to the complement of nucleic acid disclosed herein under particular hybridization conditions, which nucleic acid binds specifically to PCSK9 and antagonizes PCSK9 function. Methods for hybridizing nucleic acids are well-known in the art; see, e.g., Ausubel, *Current Protocols in Molecular Biology*, John Wiley & Sons, N.Y., 6.3.1-6.3.6, 1989. As defined herein, moderately stringent hybridization conditions may use a prewashing solution containing 5× sodium chloride/sodium citrate (SSC), 0.5% w/v SDS, 1.0 mM EDTA (pH 8.0), hybridization buffer of about 50% v/v formamide, 6×SSC, and a hybridization temperature of 55° C. (or other similar hybridization solutions, such as one containing about 50% v/v formamide, with a hybridization temperature of 42° C.), and washing conditions of 60° C., in 0.5×SSC, 0.1% w/v SDS. A stringent hybridization condition may be at 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98, or 99% identical to each other typically remain hybridized to each other. The basic parameters affecting the choice of hybridization conditions and guidance for devising suitable conditions are set forth by Sambrook et al., *Molecular Cloning: A Laboratory Manual*, Cold Spring Harbor Laboratory Press, Cold Spring Harbor, N.Y., chapters 9 and 11, 1989 and Ausubel et al. (eds), *Current Protocols in Molecular Biology*, John Wiley & Sons, Inc., sections 2.10 and 6.3-6.4, 1995, and can be readily determined by those having ordinary skill in the art based on, for example, the length and/or base composition of the DNA.

In another aspect, the present invention provides vectors comprising said nucleic acid. Vectors in accordance with the present invention include, but are not limited to, plasmids and other expression constructs (e.g., phage or phagemid, as appropriate) suitable for the expression of the desired antibody molecule at the appropriate level for the intended purpose; see, e.g., Sambrook & Russell, *Molecular Cloning: A Laboratory Manual:* $3^{rd}$ *Edition,* Cold Spring Harbor Laboratory Press. For most cloning purposes, DNA vectors may be used. Typical vectors include plasmids, modified viruses, bacteriophage, cosmids, yeast artificial chromosomes, and other forms of episomal or integrated DNA. It is well within the purview of the skilled artisan to determine an appropriate vector for a particular gene transfer, generation of a recombinant PCSK9-specific antagonist, or other use. In specific embodiments, in addition to a recombinant gene, the vector may also contain an origin of replication for autonomous replication in a host cell, appropriate regulatory sequences, such as a promoter, a termination sequence, a polyadenylation sequence, an enhancer sequence, a selectable marker, a limited number of useful restriction enzyme sites, other sequences as appropriate and the potential for high copy number. Examples of expression vectors for the production of protein-specific antagonists are well known in the art; see, e.g., Persic et al., 1997 *Gene* 187:9-18; Boel et al., 2000 *J. Immunol. Methods* 239:153-166, and Liang et al., 2001 *J. Immunol. Methods* 247:119-130. If desired, nucleic acid encoding the antagonist may be integrated into the host chromosome using techniques well known in the art; see, e.g., Ausubel, *Current Protocols in Molecular Biology,* John Wiley & Sons, 1999, and Marks et al., International Application Number WO 95/17516. Nucleic acid may also be expressed on plasmids maintained episomally or incorporated into an artificial chromosome; see, e.g., Csonka et al., 2000 *J. Cell Science* 113:3207-3216; Vanderbyl et al., 2002 *Molecular Therapy* 5:10. Specifically with regards to antibody molecules, the antibody light chain gene and the antibody heavy chain gene can be inserted into separate vectors or, more typically, both genes may be inserted into the same expression vector. Nucleic acid encoding any PCSK9-specific antagonist can be inserted into an expression vector using standard methods (e.g., ligation of complementary restriction sites on the nucleic acid fragment and vector, or blunt end ligation if no restriction sites are present). Another specific example of how this may be carried out is through use of recombinational methods, e.g. the Clontech "InFusion" system, or Invitrogen "TOPO" system (both in vitro), or intracellularly (e.g. the Cre-Lox system). Specifically with regards to antibody molecules, the light and heavy chain variable regions can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector comprising nucleic acid encoding a PCSK9-specific antagonist can encode a signal peptide that facilitates secretion of the antagonist from a host cell. The nucleic acid can be cloned into the vector such that the nucleic acid encoding a signal peptide is linked in-frame adjacent to the PCSK9-specific antagonist-encoding nucleic acid. The signal peptide may be an immunoglobulin or a non-immunoglobulin signal peptide. Any technique available to the skilled artisan may be employed to introduce the nucleic acid into the host cell; see, e.g., Morrison, 1985 *Science,* 229:1202. Methods of subcloning nucleic acid molecules of interest into expression vectors, transforming or transfecting host cells containing the vectors, and methods of making substantially pure protein comprising the steps of introducing the respective expression vector into a host cell, and cultivating the host cell under appropriate conditions are well known. The PCSK9-specific antagonist so produced may be harvested from the host cells in conventional ways. Techniques suitable for the introduction of nucleic acid into cells of interest will depend on the type of cell being used. General techniques include, but are not limited to, calcium phosphate transfection, DEAE-Dextran, electroporation, liposome-mediated transfection and transduction using viruses appropriate to the cell line of interest (e.g., retrovirus, vaccinia, baculovirus, or bacteriophage).

In another aspect, the present invention provides isolated cell(s) comprising nucleic acid encoding disclosed PCSK9-specific antagonists. A variety of different cell lines can be used for recombinant production of PCSK9-specific antagonists, including but not limited to those from prokaryotic organisms (e.g., *E. coli, Bacillus,* and *Streptomyces*) and from Eukaryotic (e.g., yeast, Baculovirus, and mammalian); see, e.g., Breitling et al., Recombinant antibodies, John Wiley & Sons, Inc. and Spektrum Akademischer Verlag, 1999. Plant cells, including transgenic plants, and animal cells, including transgenic animals (other than humans), comprising the nucleic acid or antagonists disclosed herein are also contemplated as part of the present invention. Suitable mammalian cell lines including, but not limited to, those derived from Chinese Hamster Ovary (CHO cells, including but not limited to DHFR-CHO cells (described in Urlaub and Chasin, 1980 *Proc. Natl. Acad. Sci. USA* 77:4216-4220) used, for example, with a DHFR selectable marker (e.g., as described in Kaufman and Sharp, 1982 *Mol. Biol.* 159:601-621), NS0 myeloma cells (where a GS expression system as described in WO 87/04462, WO 89/01036, and EP 338,841 may be used), COS cells, SP2 cells, HeLa cells, baby hamster kidney cells, YB2/0 rat myeloma cells, human embryonic kidney cells, human embryonic retina cells, and others comprising the nucleic acid or antagonists disclosed herein form additional embodiments of the present invention. Specific embodiments of the present invention may employ *E. coli;* see, e.g., Plückthun, 1991 *Bio/Technology* 9:545-551, or yeast, such as *Pichia,* and recombinant derivatives thereof (see, e.g., Li et al., 2006 *Nat. Biotechnol.* 24:210-215). Additional specific embodiments of the present invention may employ eukaryotic cells for the production of PCSK9-specific antagonists, see, Chadd & Chamow, 2001 *Current Opinion in Biotechnology* 12:188-194, Andersen & Krummen, 2002 *Current Opinion in Biotechnology* 13:117, Larrick & Thomas, 2001 *Current Opinion in Biotechnology* 12:411-418. Specific embodiments of the present invention may employ mammalian cells able to produce PCSK9-specific antagonists with proper post translational modifications. Post translational modifications include, but are by no means limited to, disulfide bond formation and glycosylation. Another type of post translational modification is signal peptide cleavage. Preferred embodiments herein have the appropriate glycosylation; see, e., Yoo et al., 2002 *J. Immunol. Methods* 261:1-20. Naturally occurring antibodies contain at least one N-linked carbohydrate attached to a heavy chain. Id. Different types of mammalian host cells can be used to provide for efficient post-translational modifications. Examples of such host cells include Chinese Hamster Ovary (CHO), HeLa, C6, PC12, and myeloma cells; see, Yoo et al., 2002 *J. Immunol. Methods* 261:1-20, and Persic et al., 1997 *Gene* 187:9-18.

In another aspect, the present invention provides isolated cell(s) comprising a polypeptide of the present invention.

In another aspect, the present invention provides a method of making a PCSK9-specific antagonist of the present invention, which comprises incubating a cell comprising nucleic acid encoding the PCSK9-specific antagonist, or a heavy and/or light chain of a desired PCSK9-specific antagonist (dictated by the desired antagonist) with specificity for human PCSK9 under conditions that allow the expression of the PCSK9-specific antagonist, or the expression and assembly of said heavy and/or light chains into a PCSK9-specific antagonist, and isolating said PCSK9-specific antagonist from the cell. One example by which to generate particular desired heavy and/or light chain sequence is to first amplify (and modify) the germline heavy and/or light chain variable sequences using PCR. Germline sequence for human heavy and/or light variable regions are readily available to the skilled artisan, see, e.g., the "Vbase" human germline sequence database, and Kabat, E. A. et al., 1991 *Sequences of Proteins of Immunological Interest*, Fifth Edition, U.S. Department of Health and Human Services, NIH Publication No. 91-3242; Tomlinson, I. M. et al., 1992 "The Repertoire of Human Germline VH Sequences Reveals about Fifty Groups of VH Segments with Different Hypervariable Loops" *J. Mol. Biol.* 227:776-798; and Cox, J. P. L. et al., 1994 "A Directory of Human Germ-line Vκ Segments Reveals a Strong Bias in their Usage" *Eur. J. Immunol.* 24:827-836. Mutagenesis of germline sequences may be carried out using standard methods, e.g., PCR-mediated mutagenesis where the mutations are incorporated into PCR primers, or site-directed mutagenesis. If full-length antibodies are desired, sequence is available for the human heavy chain constant region genes; see, e.g., Kabat. E. A. et al., 1991 *Sequences of Proteins of Immunological Interest*, Fifth Edition, U.S. Department of Health and Human Services, NIH Publication No. 91-3242. Fragments containing these regions may be obtained, for example, by standard PCR amplification. Alternatively, the skilled artisan can avail him/herself of vectors already encoding heavy and/or light chain constant regions.

Available techniques exist to recombinantly produce other antibody molecules which retain the specificity of an original antibody. A specific example of this is where DNA encoding the immunoglobulin variable region or the CDRs is introduced into the constant regions, or constant regions and framework regions, of another antibody molecule; see, e.g., EP-184,187, GB 2188638, and EP-239400. Cloning and expression of antibody molecules, including chimeric antibodies, are described in the literature; see, e.g., EP 0120694 and EP 0125023.

Antibody molecules in accordance with the present invention may, in one instance, be raised and then screened for characteristics identified herein using known techniques. Basic techniques for the preparation of monoclonal antibodies are described in the literature, see, e.g., Kohler and Milstein (1975, *Nature* 256:495-497). Fully human monoclonal antibodies can be produced by available methods. These methods include, but are by no means limited to, the use of genetically engineered mouse strains which possess an immune system whereby the mouse antibody genes have been inactivated and in turn replaced with a repertoire of functional human antibody genes, while leaving other components of the mouse immune system unchanged. Such genetically engineered mice allow for the natural in vivo immune response and affinity maturation process which results in high affinity, full human monoclonal antibodies. This technology is well known in the art and is fully detailed in various publications, including but not limited to U.S. Pat. Nos. 5,545,806; 5,569,825; 5,625,126; 5,633,425; 5,789,650; 5,877,397; 5,661,016; 5,814,318; 5,874,299; 5,770,249 (assigned to GenPharm International and available through Medarex, under the umbrella of the "UltraMab Human Antibody Development System"); as well as U.S. Pat. Nos. 5,939, 598; 6,075,181; 6,114,598; 6,150,584 and related family members (assigned to Abgenix, disclosing their XenoMouse® technology). See also reviews from Kellerman and Green, 2002 *Curr. Opinion in Biotechnology* 13:593-597, and Kontermann & Stefan, 2001 *Antibody Engineering*, Springer Laboratory Manuals.

Alternatively, a library of PCSK9-specific antagonists in accordance with the present invention may be brought into contact with PCSK9, and ones able to demonstrate specific binding selected. Functional studies can then be carried out to ensure proper functionality, i.e., inhibition of PCSK9-dependent inhibition of cellular LDL uptake. There are various techniques available to the skilled artisan for the selection of protein-specific molecules from libraries using enrichment technologies including, but not limited to, phage display (e.g., see technology from Cambridge Antibody Technology ("CAT") disclosed in U.S. Pat. Nos. 5,565,332; 5,733,743; 5,871,907; 5,872,215; 5,885,793; 5,962,255; 6,140,471; 6,225,447; 6,291,650; 6,492,160; 6,521,404; 6,544,731; 6,555,313; 6,582,915; 6,593,081, as well as other U.S. family members and/or applications which rely on priority filing GB 9206318, filed May 24, 1992; see also Vaughn et al., 1996, *Nature Biotechnology* 14:309-314), ribosome display (see, e.g., Hanes and Pluckthün, 1997 *Proc. Natl. Acad. Sci.* 94:4937-4942), bacterial display (see, e.g., Georgiou, et al., 1997 *Nature Biotechnology* 15:29-34) and/or yeast display (see, e.g., Kieke, et al., 1997 *Protein Engineering* 10:1303-1310). A library, for example, can be displayed on the surface of bacteriophage particles, with the nucleic acid encoding the PCSK9-specific antagonist expressed and displayed on its surface. Nucleic acid may then be isolated from bacteriophage particles exhibiting the desired level of activity and the nucleic acid used in the development of desired antagonist. Phage display has been thoroughly described in the literature; see, e.g., Kontermann & Stefan, supra, and International Application Number WO 92/01047. Specifically with regard to antibody molecules, individual heavy or light chain clones in accordance with the present invention may also be used to screen for complementary heavy or light chains, respectively, capable of interaction therewith to form a molecule of the combined heavy and light chains; see, e.g., International Application Number WO 92/01047. Any method of panning which is available to the skilled artisan may be used to identify PCSK9-specific antagonists. Another specific method for accomplishing this is to pan against the target antigen in solution, e.g. biotinylated, soluble PCSK9, and then capture the PCSK9-specific antagonist-phage complexes on streptavidin-coated magnetic beads, which are then washed to remove nonspecifically-bound phage. The captured phage can then be recovered from the beads in the same way they would be recovered from the surface of a plate, (e.g. DTT) as described herein.

PCSK9-specific antagonists may be purified by techniques available to one of skill in the art. Titers of the relevant antagonist preparation, ascites, hybridoma culture fluids, or relevant sample may be determined by various serological or immunological assays which include, but are not limited to, precipitation, passive agglutination, enzyme-linked immunosorbent antibody ("ELISA") techniques and radioimmunoassay ("RIA") techniques.

In another aspect, the present invention provides a method for antagonizing the activity of PCSK9, which comprises contacting a cell or tissue sample typically effected by PCSK9 (i.e., comprising LDL receptors) with a PCSK9-specific antagonist disclosed herein under conditions that allow said antagonist to bind to PCSK9 when present and inhibit PCSK9's inhibition of cellular LDL uptake. Specific embodiments of the present invention include such methods wherein the cell is a human cell. In another aspect, the present invention provides a method for antagonizing the activity of PCSK9 in a subject, which comprises administering to the subject a therapeutically effective amount of a PCSK9-specific antagonist of the present invention. Use of the term "antagonizing" refers to the act of opposing, counteracting, neutralizing or curtailing one or more functions of PCSK9. Inhibition or antagonism of one or more of associated PCSK9 functional properties can be readily determined according to methodologies known to the art (see, e.g., Barak & Webb, 1981 *J. Cell Biol.* 90:595-604; Stephan & Yurachek, 1993 *J. Lipid Res.* 34:325330; and McNamara et al., 2006 *Clinica Chimica Acta* 369:158-167) as well as those described herein. Inhibition or antagonism will effectuate a decrease in PCSK9 activity relative to that seen in the absence of the antagonist or, for example, that seen when a control antagonist of irrelevant specificity is present. Preferably, a PCSK9-specific antagonist in accordance with the present invention antagonizes PCSK9 functioning to the point that there is a decrease of at least 10%, of the measured parameter, and more preferably, a decrease of at least 20%, 30%, 40%, 50%, 60%, 70%, 80%, 90% and 95% of the measured parameter. Such inhibition/antagonism of PCSK9 functioning is particularly effective in those instances where its functioning is contributing at least in part to a particular phenotype, disease, disorder or condition which is negatively impacting the subject. Also contemplated are methods of using the disclosed antagonists in the manufacture of a medicament for treatment of a PCSK9-associated disease, disorder or condition or, alternatively, a disease, disorder or condition that could benefit from the effects of a PCSK9 antagonist. PCSK9-specific antagonists disclosed herein may be used in a method of treatment or diagnosis of a particular individual (human or primate). The method of treatment can be prophylactic or therapeutic in nature. In another aspect, the present invention provides a pharmaceutically acceptable composition comprising a PCSK9-specific antagonist of the invention and a pharmaceutically acceptable carrier, excipient, diluent, stabilizer, buffer, or alternative designed to facilitate administration of the antagonist in the desired format and amount to the treated individual. Methods of treatment in accordance with the present invention comprise administering to an individual a therapeutically (or prophylactically) effective amount of a PCSK9-specific antagonist of the present invention. Use of the terms "therapeutically effective" or "prophylactically effective" in reference to an amount refers to the amount necessary at the intended dosage to achieve the desired therapeutic/prophylactic effect for the period of time desired. The desired effect may be, for example, amelioration of at least one symptom associated with the treated condition. These amounts will vary, as the skilled artisan will appreciate, according to various factors, including but not limited to the disease state, age, sex and weight of the individual, and the ability of the PCSK9-specific antagonist to elicit the desired effect in the individual. The response may be documented by in vitro assay, in vivo non-human animal studies, and/or further supported from clinical trials. The antagonist-based pharmaceutical composition of the present invention may be formulated by any number of strategies known in the art, see, e.g., McGoff and Scher, 2000 *Solution Formulation of Proteins/Peptides*: In—McNally, E. J., ed. Protein Formulation and Delivery. New York, N.Y.: Marcel Dekker; pp. 139-158; Akers & Defilippis, 2000, *Peptides and Proteins as Parenteral Solutions*. In—Pharmaceutical Formulation Development of Peptides and Proteins. Philadelphia, Pa.: Taylor and Francis; pp. 145-177; Akers et al., 2002, *Pharm. Biotechnol.* 14:47-127. A pharmaceutically acceptable composition suitable for patient administration will contain an effective amount of the PCSK9-specific antagonist in a formulation which both retains biological activity while also promoting maximal stability during storage within an acceptable temperature range.

The antagonist-based pharmaceutically acceptable composition may be in liquid or solid form. Any technique for production of liquid or solid formulations may be utilized. Such techniques are well within the realm of the abilities of the skilled artisan. Solid formulations may be produced by any available method including, but not limited to, lyophilization, spray drying, or drying by supercritical fluid technology. Solid formulations for oral administration may be in any form rendering the antagonist accessible to the patient in the prescribed amount and within the prescribed period of time. The oral formulation can take the form of a number of solid formulations including, but not limited to, a tablet, capsule, or powder. Solid formulations may alternatively be lyophilized and brought into solution prior to administration for either single or multiple dosing. Antagonist compositions should generally be formulated within a biologically relevant pH range and may be buffered to maintain a proper pH range during storage. Both liquid and solid formulations generally require storage at lower temperatures (e.g., 2-8° C.) in order to retain stability for longer periods. Formulated antagonist compositions, especially liquid formulations, may contain a bacteriostat to prevent or minimize proteolysis during storage, including but not limited to effective concentrations (e.g., $\leq$1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antagonist formulation, including but not limited to sugars as a cryoprotectant (including but not limited to polyhydroxy hydrocarbons such as sorbitol, mannitol, glycerol, and dulcitol and/or disaccharides such as sucrose, lactose, maltose, or trehalose) and, in some instances, a relevant salt (including but not limited to NaCl, KCl, or LiCl). Such antagonist formulations, especially liquid formulations slated for long term storage, will rely on a useful range of total osmolarity to both promote long term stability at temperatures of, for example, 2-8° C. or higher, while also making the formulation useful for parenteral injection. As appropriate, preservatives, stabilizers, buffers, antioxidants and/or other additives may be included. The formulations may contain a divalent cation (including but not limited to MgCl2, CaCl2, and MnCl2); and/or a non-ionic surfactant (including but not limited to Polysorbate-80 (Tween 80™), Polysorbate-60 (Tween 60™), Polysorbate-40 (Tween 40™), and Polysorbate-20 (Tween 20™), polyoxyethylene alkyl ethers, including but not limited to Brij 58™, Brij35™, as well as others such as Triton X-100™, Triton X-114™, NP40™, Span 85 and the Pluronic series of non-ionic surfactants (e.g., Pluronic 121)). Any combination of such components form specific embodiments of the present invention.

Pharmaceutical compositions in liquid format may include a liquid carrier, e.g., water, petroleum, animal oil, vegetable oil, mineral oil, or synthetic oil. The liquid format may also include physiological saline solution, dextrose or other saccharide solution or glycols, such as ethylene glycol, propylene glycol or polyethylene glycol.

Preferably, the pharmaceutical composition may be in the form of a parenterally acceptable aqueous solution that is pyrogen-free with suitable pH, tonicity, and stability. Pharmaceutical compositions may be formulated for administration after dilution in isotonic vehicles, for example, Sodium Chloride Injection, Ringer's Injection, or Lactated Ringer's Injection.

Dosing of antagonist therapeutics is well within the realm of the skilled artisan, see, e.g., Lederman et al., 1991 *Int. J. Cancer* 47:659-664; Bagshawe et al., 1991 *Antibody, Immunoconjugates and Radiopharmaceuticals* 4:915-922, and will vary based on a number of factors including but not limited to the particular PCSK9-specific antagonist utilized, the patient being treated, the condition of the patient, the area being treated, the route of administration, and the treatment desired. A physician or veterinarian of ordinary skill can readily determine and prescribe the effective therapeutic amount of the antagonist. Dosage ranges may be from about 0.01 to 100 mg/kg, and more usually 0.05 to 25 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. For purposes of illustration, and not limitation, in specific embodiments, a dose of 5 mg to 2.0 g may be utilized to deliver the antagonist systemically. Optimal precision in achieving concentrations of antagonist within a range that yields efficacy without toxicity requires a regimen based on the kinetics of the drug's availability to the target site(s). This involves a consideration of the distribution, equilibrium, and elimination of the PCSK9-specific antagonist. Antagonists described herein may be used alone at appropriate dosages. Alternatively, co-administration or sequential administration of other agents may be desirable. It will be possible to present a therapeutic dosing regime for the PCSK9-specific antagonists of the present invention in conjunction with alternative treatment regimes. For example, PCSK9-specific antagonists may be used in combination or in conjunction with other cholesterol-lowering drugs, including, but not limited to, cholesterol absorption inhibitors (e.g., Zetia™) and cholesterol synthesis inhibitors (e.g., Zocor™ and Vytorin™). Individuals (subjects) capable of treatment include primates, human and non-human, and include any non-human mammal or vertebrate of commercial or domestic veterinary importance.

The PCSK9-specific antagonist may be administered to an individual by any route of administration appreciated in the art, including but not limited to oral administration, administration by injection (specific embodiments of which include intravenous, subcutaneous, intraperitoneal or intramuscular injection), administration by inhalation, intranasal, or topical administration, either alone or in combination with other agents designed to assist in the treatment of the individual. The route of administration should be determined based on a number of considerations appreciated by the skilled artisan including, but not limited to, the desired physiochemical characteristics of the treatment. Treatment may be provided on a daily, weekly, biweekly, or monthly basis, or any other regimen that delivers the appropriate amount of PCSK9-specific antagonist to the individual at the prescribed times such that the desired treatment is effected and maintained. The formulations may be administered in a single dose or in more than one dose at separate times.

In particular embodiments, the condition treated is selected from the group consisting of: hypercholesterolemia, coronary heart disease, metabolic syndrome, acute coronary syndrome and related conditions. Use of a PCSK9-specific antagonist in the manufacture of a medicament for treatment of a PSCK9-associated condition or, alternatively a condition that could stand to benefit from a PCSK9 antagonist, including those specified above, therefore, forms an important embodiment of the present invention.

The present invention further provides for the administration of disclosed anti-PCSK9 antagonists for purposes of gene therapy. Through such methods, cells of a subject are transformed with nucleic acid encoding a PCSK9-specific antagonist of the invention. Subjects comprising the nucleic acids then produce the PCSK9-specific antagonists endogenously. Previously, Alvarez, et al, *Clinical Cancer Research* 6:3081-3087, 2000, introduced single-chain anti-ErbB2 antibodies to subjects using a gene therapy approach. The methods disclosed by Alvarez, et al, supra, may be easily adapted for the introduction of nucleic acids encoding an anti-PCSK9 antibody of the invention to a subject.

Nucleic acids encoding any PCSK9-specific antagonist may be introduced to a subject.

The nucleic acids may be introduced to the cells of a subject by any means known in the art. In preferred embodiments, the nucleic acids are introduced as part of a viral vector. Examples of preferred viruses from which the vectors may be derived include lentiviruses, herpes viruses, adenoviruses, adeno-associated viruses, vaccinia virus, baculovirus, alphavirus, influenza virus, and other recombinant viruses with desirable cellular tropism.

Various companies produce viral vectors commercially, including, but by no means limited to, Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Methods for constructing and using viral vectors are known in the art (see, e.g., Miller, et al, *BioTechniques* 7:980-990, 1992). Preferably, the viral vectors are replication defective, that is, they are unable to replicate autonomously, and thus are not infectious, in the target cell. Preferably, the replication defective virus is a minimal virus, i.e., it retains only the sequences of its genome which are necessary for encapsidating the genome to produce viral particles. Defective viruses, which entirely or almost entirely lack viral genes, are preferred. Use of defective viral vectors allows for administration to cells in a specific, localized area, without concern that the vector can infect other cells. Thus, a specific tissue can be specifically targeted.

Examples of vectors comprising attenuated or defective DNA virus sequences include, but are not limited to, a defective herpes virus vector (Kanno et al, *Cancer Gen. Ther.* 6:147-154, 1999; Kaplitt et al, *J. Neurosci. Meth.* 71:125-132, 1997 and Kaplitt et al, *J. Neuro Onc.* 19:137-147, 1994).

Adenoviruses are eukaryotic DNA viruses that can be modified to efficiently deliver a nucleic acid of the invention to a variety of cell types. Attenuated adenovirus vectors, such as the vector described by Strafford-Perricaudet et al, *J. Clin. Invest.* 90:626-630, 1992 are desirable in some instances. Various replication defective adenovirus and minimum adenovirus vectors have been described (PCT Publication Nos. WO94/26914, WO94/28938, WO94/28152, WO94/12649, WO95/02697 and WO96/22378). The replication defective recombinant adenoviruses according to the invention can be prepared by any technique known to a person skilled in the art (Levrero et al, *Gene* 101:195, 1991; EP 185573; Graham, *EMBO J.* 3:2917, 1984; Graham et al, *J. Gen. Virol.* 36:59, 1977).

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The use of vectors derived from the AAVs for transferring genes in vitro and in vivo has been described (see Daly, et al, *Gene Ther.* 8:1343-1346, 2001, Larson et al, *Adv. Exp. Med. Bio.* 489:45-57, 2001; PCT Publication Nos. WO 91/18088 and WO 93/09239; U.S. Pat. Nos. 4,797,368 and 5,139,941 and EP 488528B1).

In another embodiment, the gene can be introduced in a retroviral vector, e.g., as described in U.S. Pat. Nos. 5,399,346, 4,650,764, 4,980,289, and 5,124,263; Mann et al, *Cell* 33:153, 1983; Markowitz et al, *J. Virol.*, 62:1120, 1988; EP 453242 and EP178220. The retroviruses are integrating viruses which infect dividing cells.

Lentiviral vectors can be used as agents for the direct delivery and sustained expression of nucleic acids encoding a PCSK9-specific antagonist of the invention in several tissue types, including brain, retina, muscle, liver and blood. The vectors can efficiently transduce dividing and nondividing cells in these tissues, and maintain long-term expression of the PCSK9-specific antagonist. For a review, see Zufferey et al, *J. Virol.* 72:9873-80, 1998 and Kafri et al, *Curr. Opin. Mol. Ther.* 3:316-326, 2001. Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virus particles at titers greater than $10^6$ IU/ml for at least 3 to 4 days; see Kafri et al, *J. Virol.* 73:576-584, 1999. The vector produced by the inducible cell line can be concentrated as needed for efficiently transducing nondividing cells in vitro and in vivo.

Sindbis virus is a member of the alphavirus genus and has been studied extensively since its discovery in various parts of the world beginning in 1953. Gene transduction based on alphavirus, particularly Sindbis virus, has been well-studied in vitro (see Straus et al, *Microbiol. Rev.,* 58:491-562, 1994; Bredenbeek et al, *J. Virol.,* 67:6439-6446, 1993; Ijima et al, *Int. J. Cancer* 80:110-118, 1999 and Sawai et al, *Biochim. Biophyr. Res. Comm.* 248:315-323, 1998. Many properties of alphavirus vectors make them a desirable alternative to other virus-derived vector systems being developed, including rapid engineering of expression constructs, production of high-titered stocks of infectious particles, infection of nondividing cells, and high levels of expression (Strauss et al, 1994 supra). Use of Sindbis virus for gene therapy has been described. (Wahlfors et al, *Gene. Ther.* 7:472-480, 2000 and Lundstrom, *J. Recep. Sig. Transduct. Res.* 19(1-4):673-686, 1999.

In another embodiment, a vector can be introduced to cells by lipofection or with other transfection facilitating agents (peptides, polymers, etc.). Synthetic cationic lipids can be used to prepare liposomes for in vivo and in vitro transfection of a gene encoding a marker (Feigner et al, *Proc. Natl. Acad. Sci. USA* 84:7413-7417, 1987 and Wang et al, *Proc. Natl. Acad. Sci. USA* 84:7851-7855, 1987). Useful lipid compounds and compositions for transfer of nucleic acids are described in PCT Publication Nos. WO 95/18863 and WO 96/17823, and in U.S. Pat. No. 5,459,127.

It is also possible to introduce the vector in vivo as a naked DNA plasmid. Naked DNA vectors for gene therapy can be introduced into desired host cells by methods known in the art, e.g., electroporation, microinjection, cell fusion, DEAE dextran, calcium phosphate precipitation, use of a gene gun, or use of a DNA vector transporter (see, e.g., Wilson, et al, *J. Biol. Chem.* 267:963-967, 1992; Williams et al, *Proc. Natl. Acad. Sci. USA* 88:2726-2730, 1991). Other reagents commonly used for transfection of plasmids include, but are by no means limited to, FuGene, Lipofectin, and Lipofectamine. Receptor-mediated DNA delivery approaches can also be used (Wu et al, *J. Biol. Chem.* 263:14621-14624, 1988). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Vilquin et al, *Gene Ther.* 8:1097, 2001; Payen et al, *Exp. Hematol.* 29:295-300, 2001; Mir, *Bioelectrochemistry* 53:1-10, 2001; PCT Publication Nos. WO 99/01157, WO 99/01158 and WO 99/01175).

Pharmaceutical compositions suitable for such gene therapy approaches and comprising nucleic acids encoding an anti-PCSK9 antagonist of the present invention are included within the scope of the present invention.

In another aspect, the present invention provides a method for identifying, isolating, quantifying or antagonizing PCSK9 in a sample of interest using a PCSK9-specific antagonist of the present invention. The PCSK9-specific antagonists may be utilized as research tools in immunochemical assays, such as Western blots, ELISAs, radioimmunoassay, immunohistochemical assays, immunoprecipitations, or other immunochemical assays known in the art (see, e.g., Immunological Techniques Laboratory Manual, ed. Goers, J. 1993, Academic Press) or various purification protocols. The antagonists may have a label incorporated therein or affixed thereto to facilitate ready identification or measurement of the activities associated therewith. One skilled in the art is readily familiar with the various types of detectable labels (e.g., enzymes, dyes, or other suitable molecules which are either readily detectable or cause some activity/result that is readily detectable) which are or may be useful in the above protocols.

An additional aspect of the present invention are kits comprising PCSK9-specific antagonists or pharmaceutical compositions disclosed herein and instructions for use. Kits typically but need not include a label indicating the intended use of the contents of the kit. The term label includes any writing, or recorded material supplied on or with the kit, or which otherwise accompanies the kit.

The present invention also relates to a method for identifying PCSK9-specific antagonists in a cell sample which comprises providing purified PCSK9 (or functional equivalent) and labeled LDL particles to a cell sample; providing a molecule(s) suspected of being a PCSK9 antagonist to the cell sample; incubating said cell sample for a period of time sufficient to allow LDL particle uptake by the cells; quantifying the amount of label incorporated into the cell; and identifying those candidate antagonists that result in an increase in the amount of quantified label as compared with that observed when PCSK9 (or functional equivalent) is administered alone. The present invention also relates to a method for identifying PCSK9-specific antagonists in a cell sample which comprises providing purified PCSK9 (or functional equivalent) and labeled LDL particles to a cell sample; providing a molecule(s) suspected of being a PCSK9 antagonist to the cell sample; incubating said cell sample for a period of time sufficient to allow LDL particle uptake by the cells; isolating cells of the cell sample by removing the supernate; reducing non-specific association of labeled LDL particles (whether to the plate, the cells, or anything other than the LDL receptor); lysing the cells; quantifying the amount of label retained within the cell lysate; and identifying those candidate antagonists that result in an increase in the amount of quantified label as compared with that observed when PCSK9 is administered alone. Candidate antagonists that result in an increase in the amount of quantified label are PCSK9 antagonists. This method has proven to be an effective means for identifying PCSK9-specific antagonists and, thus, forms an important aspect of the present invention. Any type of cell bearing the LDL receptor can be employed in the disclosed method including, but not limited to HEK cells, HepG2 cells, and CHO cells. A "functional equivalent" of PCSK9 is defined herein as a protein with at least 80% homology to PCSK9 at the amino acid level having either conservative amino acid substitutions or modifications thereto; said protein which exhibits measurable inhibition of LDL uptake by the LDL receptor. Nucleic acid encoding said protein would hybridize to the complement of nucleic acid encoding PCSK9 under stringent hybridization conditions. Any number of cells can be plated. For purposes of exemplification, the current methods plated 30,000 cells/well in a 96 well plate. In preferred embodiments, the cells are in serum-free media when the PCSK9 (or functional equivalent) is added. In specific embodiments, the cells are plated for a period of time (e.g., ~24 hours) in media with serum; subsequently plated in serum-free media (having removed the serum-containing media) for a period of time (e.g., ~24 hours); prior to addition of the purified PCSK9 (or functional equivalent) and labeled LDL particles. The step of reducing non-specific association of labeled LDL particles is typically carried out by a washing/rinsing step(s) albeit, as the skilled artisan is aware, any technique(s) of accomplishing reduction of non-specific association may be utilized. LDL particles derived from any source are of use in the above-described assays. In preferred embodiments, the LDL particles are fresh particles derived from blood. This can be accomplished by any method available to the skilled artisan including, but not limited to, the method of Havel et al., 1955 *J. Clin. Invest.* 34: 1345-1353. In specific embodiments, the LDL particles are labeled with fluorescence. In particular embodiments, the labeled LDL particles have incorporated therein visible wavelength excited fluorophore 3,3'-dioctadecylindocarbocyanine iodide (dil(3)) to form the highly fluorescent LDL derivative dil(3)-LDL. As recognized by one skilled in the art, the present invention can be practiced with any label which enables the skilled artisan to detect LDL in the cellular lysate. In specific embodiments, an LDL analog may be used that would only become detectable (e.g., become fluorescent or fluoresce at a different wavelength, etc.) when metabolized intracellularly or, for instance, if it were to become associated with (or dissociated from) other molecules in the process of becoming internalized (e.g. a FRET assay, in which an LDL analog would become associated with a secondary fluor, or else be dissociated from a quencher). Any means available in the art for detecting internalization of labeled LDL particles can be employed in the present invention. The incubation time for the LDL particles and PCSK9 with the cells is an amount of time sufficient to allow LDL particle uptake by the cells. In specific embodiments, this time is within the range of 5 minutes to 360 minutes. In specific embodiments, the concentration of PCSK9 or functional equivalent added to the cells is in the range of 1 nM to 5 µM. In more specific embodiments, the concentration of PCSK9 or functional equivalent added to the cells is in the range of 0.1 nM to 3 µM. One specific means by which the skilled artisan can determine a range of concentrations for a particular PCSK9 protein is to develop a dose response curve in the LDL-uptake assay. A concentration of PCSK9 can be selected that promotes close to maximal loss of LDL-uptake and is still in the linear range of the dose response curve. Typically, this concentration is ~5 times the EC-50 of the protein extracted from the dose response curve. The concentrations can vary by protein. For purposes of exemplification, the amount of wild-type PCSK9 used in Example 5 was ~320 nM, whereas, in equivalent assays employing "gain of function" PCSK9s (e.g., S127R and D374Y), said mutants were added at a lower concentration (e.g., 6-50 nM). In the described assay, cells are typically maintained at a temperature suitable for their maintenance and/or growth. In specific embodiments, the temperature is maintained around 37° C.

The following examples are provided to illustrate the present invention without limiting the same hereto:

EXAMPLE 1

Isolation of Recombinant Fab Display Phage

Recombinant Fab phage display libraries (see, e.g., Knappik et al., 2000 *J. Mol. Biol.* 296:57-86) were panned against immobilized recombinant human PCSK9 through a process which is briefly described as follows: Phage Fab display libraries were first divided into 3 pools: one pool of VH2+VH4+VH5, another of VH1+VH6, and a third pool of VH3. The phage pools and immobilized PCSK9 protein were blocked with nonfat dry milk.

For the first round of panning, each phage pool was bound independently to V5-, His-tagged PCSK9 protein immobilized in wells of Nunc Maxisorp plate. Immobilized phage-PCSK9 complexes were washed sequentially with (1) PBS/0.5% Tween™ 20 (Three quick washes); (2) PBS/0.5% Tween™ 20 (One 5 min. incubation with mild shaking); (3) PBS (Three quick washes); and (4) PBS (Two 5-min. incubations with mild shaking). Bound phages were eluted with 20 mM DTT and all three eluted phage suspensions were combined into one tube. *E. coli* TG1 were infected with eluted phages. Pooled culture of phagemid-bearing cells (chloramphenicol-resistant) were grown up and frozen stock of phagemid-bearing culture were made. Phage were rescued from culture by co-infection with helper phage, and phage stock for next round of panning were made.

For the second round of panning, phages from Round 1 were bound to immobilized, blocked V5-, His-tagged PCSK9 protein. Immobilized phage-PCSK9 complexes were washed sequentially with (1) PBS/0.05% Tween™ 20 (One quick wash); (2) PBS/0.05% Tween™ 20 (Four 5 min. incubations with mild shaking); (3) PBS (One quick wash); and (4) PBS (Four 5-min. incubations with mild shaking). Bound phages were eluted, *E. coli* TG1 cells were infected, and phage were rescued as in Round 1.

For the third round of panning, phages from Round 2 were bound to immobilized, blocked V5-His-tagged PCSK9 protein. Immobilized phage-PCSK9 complexes were washed sequentially with (1) PBS/0.05% Tween™ 20 (Ten quick washes); (2) PBS/0.05% Tween™ 20 (Five 5 min. incubations with mild shaking); (3) PBS (Ten quick washes); and (4) PBS (Five 5-min. incubations with mild shaking). Bound phages were eluted and *E. coli* TG1 cells were infected as in Round 1. Phagemid-infected cells were grown overnight and phagemid DNA was prepared.

XbaI-EcoRI inserts from Round 3 phagemid DNA were subcloned into Morphosys Fab expression vector pMORPH_x9_MH (see, e.g., FIG. 1), and a library of Fab expression clones was generated in *E. coli* TG1 F⁻. Transformants were spread on LB+chloramphenicol+glucose plates and grown overnight to generate bacterial colonies. Individual transformant colonies were picked and placed into wells of two 96-well plates for growth and screening for Fab expression.

EXAMPLE 2

ELISA Screening of Bacterially Expressed FABS

Cultures of individual transformants were IPTG-induced and grown overnight for Fab expression. Culture supernatants (candidate Fabs) were incubated with purified V5-, His-tagged PCSK9 protein immobilized in wells of 96-well Nunc Maxisorp plates, washed with 0.1% Tween™ 20 in PBS using a plate washer, incubated with HRP-coupled anti-Fab antibody, and washed again with PBS/Tween™ 20. Bound HRP was detected by addition of TMP substrated, and $A_{450}$ values of wells were read with a plate reader.
Negative controls were included as follows:
Controls for nonspecific Fab binding on each plate were incubated with parallel expressed preparations of anti-EsB, an irrelevant Fab.
Growth medium only.
Positive controls for ELISA and Fab expression were included as follows:
EsB antigen was bound to three wells of the plate and subsequently incubated with anti-EsB Fab. To control for Fabs reacting with the V5 or His tags of the recombinant PCSK9 antigen, parallel ELISAs were performed using V5-, His-tagged secreted alkaline phosphatase protein (SEAP) expressed in the same cells as the original PCSK9 antigen and similarly purified. Putative PCSK9-reactive Fabs were identified as yielding >3× background values when incubated with PCSK9 antigen but negative when incubated with SEAP. Clones scoring as PCSK9-reactive in the first round of screening were consolidated onto a single plate, re-grown in triplicate, re-induced with IPTG, and re-assayed in parallel ELISAs vs. PCSK9 and SEAP. Positive and negative controls were included as described above. Clones scoring positive in at least 2 of 3 replicates were carried forward into subsequent characterizations. In cases of known or suspected mixed preliminary clones, cultures were re-purified by streaking for single colonies on 2×YT plates with chloramphenicol, and liquid cultures from three or more separate colonies were assayed again by ELISAs in triplicate as described above.

EXAMPLE 3

DNA Sequence Determination of PCSK9 ELISA-Positive FAB Clones

Bacterial culture for DNA preps were made by inoculating 1.2 ml 2×YT liquid media with chloramphenicol from master glycerol stocks of positive Fabs, and growing overnight. DNA was prepared from cell pellets centrifuged out of the overnight cultures using the Qiagen Turbo Mini preps performed on a BioRobot 9600. ABI Dye Terminator cycle sequencing was performed on the DNA with Morphosys defined sequencing primers and run on an ABI 3100 Genetic Analyzer, to obtain the DNA sequence of the Fab clones. DNA sequences were compared to each other to determine unique clone sequences and to determine light and heavy chain subtypes of the Fab clones.

EXAMPLE 4

Expression and Purification of FAB's from Unique PCSK9 ELISA-Positive Clones Fabs from ELISA-positive clones (1CX1G08, 3BX5C01, 3CX2A06, 3CX3D02 and 3CX4B08) and the EsB (negative control) Fab were expressed by IPTG-induction in *E. coli* TG1F⁻ cells. Cultures were lysed and the His-tagged Fabs were purified by immobilized metal ion affinity chromatography (IMAC), and proteins were exchanged into 25 mM HEPES pH 7.3/150 mM NaCl by centrifugal diafiltration. Proteins were analyzed by electrophoresis on Caliper Lab-Chip 90 and by conventional SDS-PAGE, and quantified by Bradford protein assay. Purified Fab protein was re-assayed by ELISA in serial dilutions to confirm activity of purified Fab. Positive and Negative controls were run as before. Purified Fab preparations were analyzed in the EXOPOLAR (cholesterol uptake) assay described below.

EXAMPLE 5

Exopolar Assay: Effects of Exogenous PCSK9 on Cellular LDL Uptake

On day 1, 30,000 cells/well were plated in a 96 well polyD-lysine coated plate. On day 2, the media was switched to no-serum containing DMEM media. On day 3, the media was removed and the cells were washed with OptiMEM. Purified PCSK9 was added in 100 µl of DMEM media containing LPDS and dI-LDL. The plates were incubated at 37° C. for 6.5 hrs. The cells were washed quickly in TBS containing 2 mg/ml BSA; then washed in TBS-BSA for 2 minutes; and then washed twice (but quickly) with TBS. The cells were lysed in 100 µl RIPA buffer. Fluorescence was then measured in the plate using an Ex 520, Em 580 nm. The total cellular protein in each well was measured using a BCA Protein Assay and the fluorescence units were then normalized to total protein.

Figure 2:
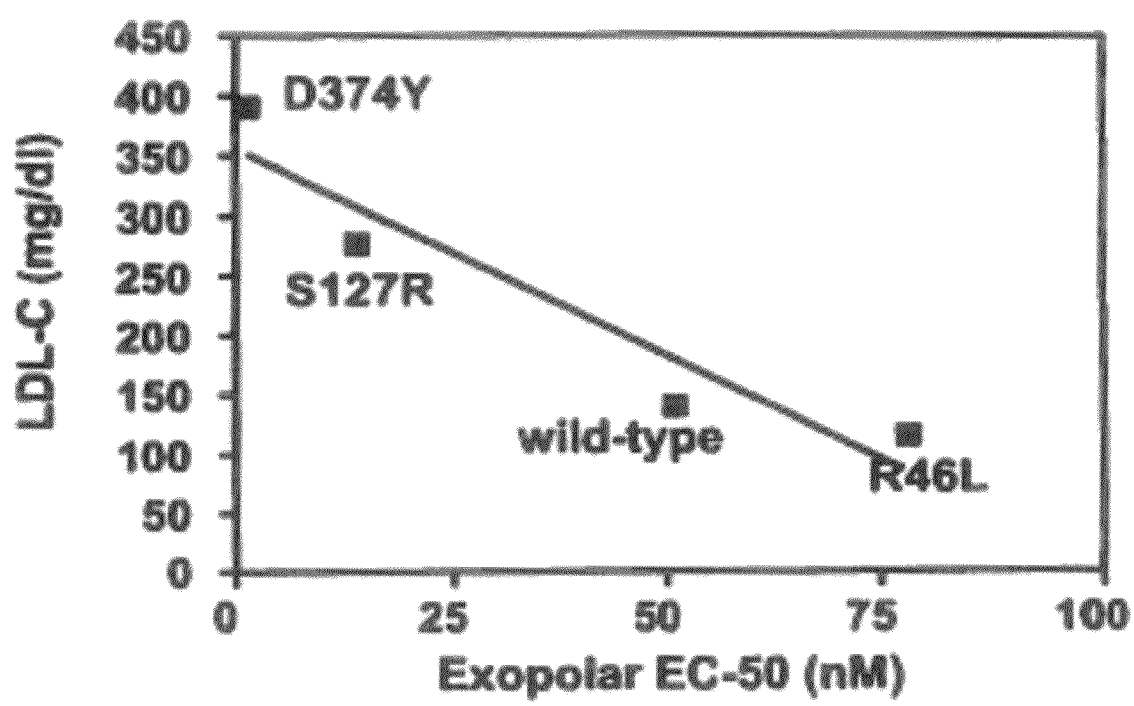
FIG. 2 illustrates how the potencies of PCSK9 mutants in Exopolar correlate with plasma LDL-cholesterol.

The Exopolar Assay is effective for characterizing variant effects on LDL uptake; see FIG. 2 illustrating how the potencies of PCSK9 mutants correlate with plasma LDL-cholesterol in the Exopolar Assay. The data is tabulated as follows:

TABLE 2

| Mutation | Gain/Loss | LDL-C (mg/dl) | EC-50 (nM) Exopolar |
|---|---|---|---|
| S127R | Gain | 277 | 14 |
| D374Y | Gain | 388 | 1.3 |
| Wild-type | | 140 | 51 |
| R46L | Loss | 116 | 78 |

Figure 3:
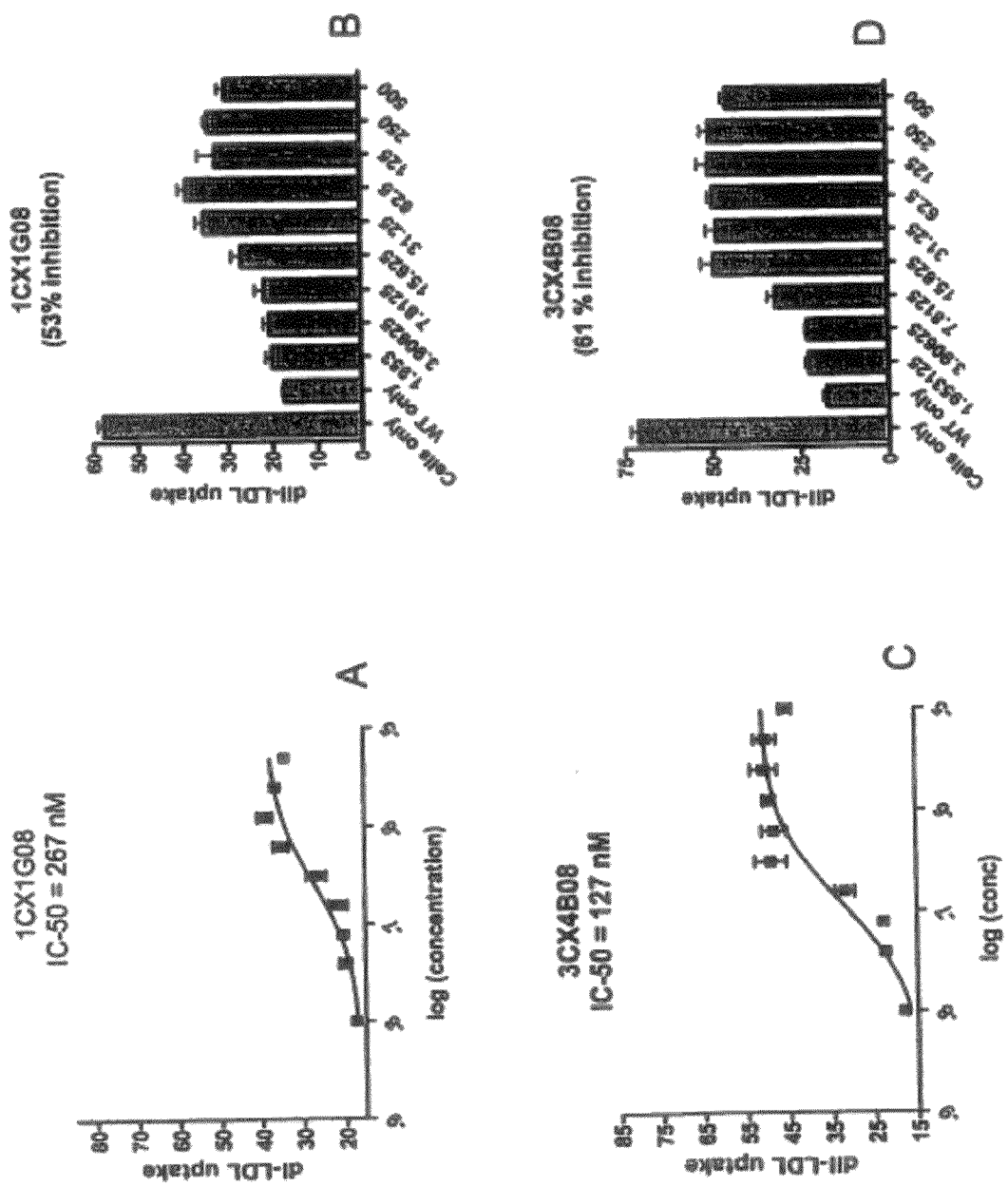
FIGS. 3A-3D illustrate 1CX1G08's and 3CX4B08's dose-dependent inhibition of PSCK9-dependent effects on LDL uptake.
Figure 4:
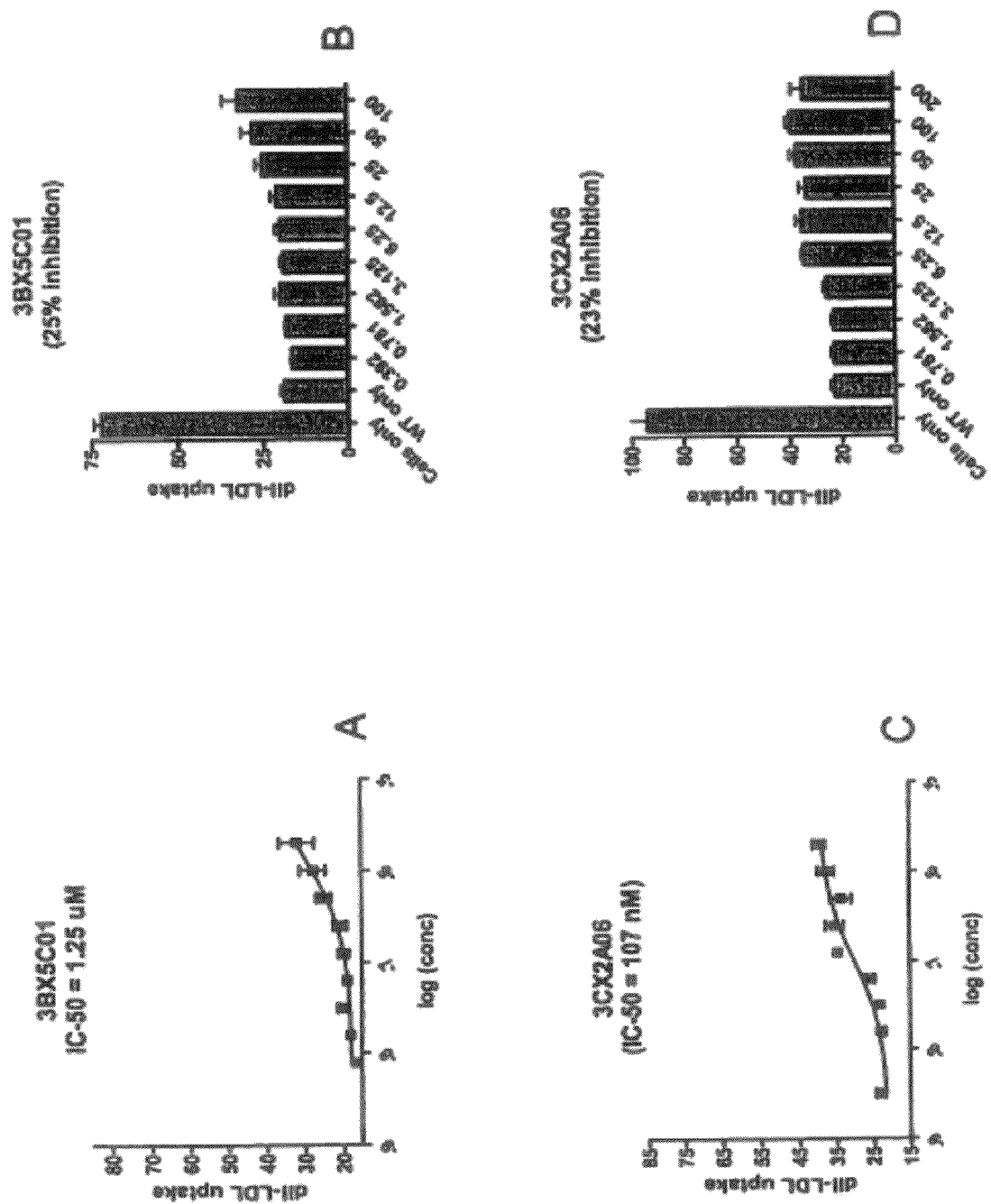
FIGS. 4A-4D illustrate 3BX5C01's and 3CX2A06's dose-dependent inhibition of PSCK9-dependent effects on LDL uptake.
Figure 5:
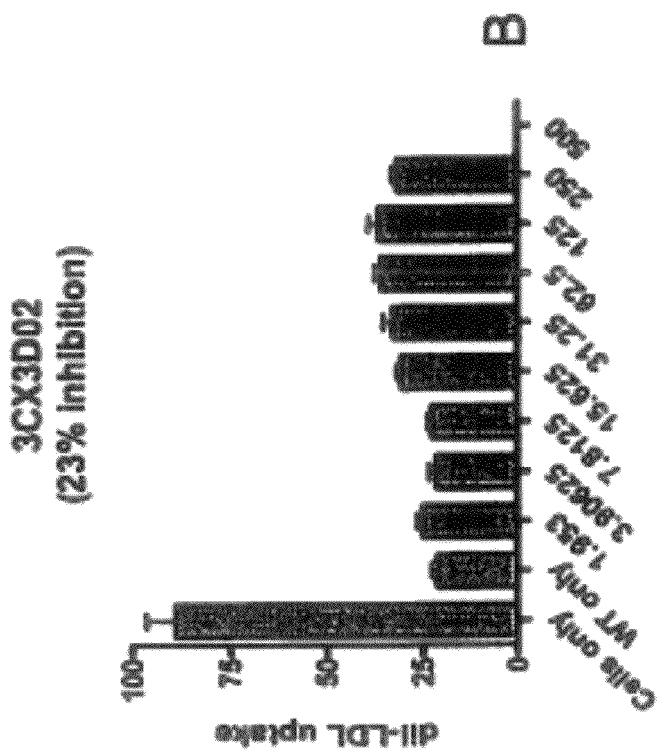
FIGS. 5A-5B illustrate 3CX3D02's dose-dependent inhibition of PSCK9-dependent effects on LDL uptake.
Figure 5:
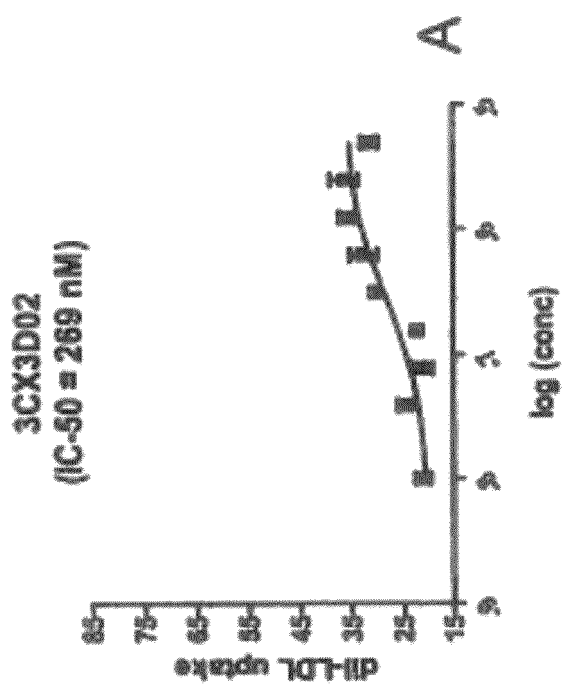

Results: Five antibody molecules (1CX1G08; 3BX5C01; 3CX2A06; 3CX3D02; and 3CX4B08) dose-dependently inhibited the effects of PCSK9 on LDL uptake; an effect which was reproducibly observed. The amount of PCSK9 added to the cells was =320 nM. The antibody molecules comprise as follows: (a) 1CX1G08, a LC chain of SEQ ID NO: 1 (comprising a VL of SEQ ID NO: 93), and a Fd chain of SEQ ID NO: 9 (comprising a VH of SEQ ID NO: 11); (b) 3BX5C01, a LC chain of SEQ ID NO: 19 (comprising a VL of SEQ ID NO: 95), and a Fd chain of SEQ ID NO: 25 (comprising a VH of SEQ ID NO: 27); (c) 3CX2A06, a LC chain of SEQ ID NO: 35 (comprising a VL of SEQ ID NO: 97), and a Fd chain of SEQ ID NO: 43 (comprising a VH of SEQ ID NO: 45); (d) 3CX3D02, a LC chain of SEQ ID NO: 53 (comprising a VL of SEQ ID NO: 99), and a Fd chain of SEQ ID NO: 59 (comprising a VH of SEQ ID NO: 61); and (e) 3CX4B08, a LC chain of SEQ ID NO: 69 (comprising a VL of SEQ ID NO: 101), and a Fd chain of SEQ ID NO: 77 (comprising a VH of SEQ ID NO: 79). FIGS. 3A-3D illustrate 1CX1G08's and 3CX4B08's dose-dependent inhibition of PSCK9-dependent effects on LDL uptake. FIGS. 3B and 3D have two controls: (i) a cell only control, showing the basal level of cellular LDL uptake, and (ii) a cell+PCSK9 (25 μg/ml) control which shows the level of PCSK9-dependent loss of LDL-uptake. The titration experiments which contain Fab and PCSK9 were done at a fixed concentration of PCSK9 (25 μg/ml) and increasing concentrations of Fab shown in the graphs. FIGS. 3A and 3C show calculations of IC-50s. 1CX1G08 exhibited a 53% inhibition of PCSK9-dependent inhibition of cellular LDL uptake, while 3CX4B08 exhibited a 61% inhibition. FIGS. 4A-4D illustrate 3BX5C01's and 3CX2A06's dose-dependent inhibition of PSCK9-dependent effects on LDL uptake. FIGS. 4B and 4D have two controls: (i) a cell only control, showing the basal level of cellular LDL uptake, and (ii) a cell+PCSK9 (25 μg/ml) control which shows the level of PCSK9-dependent loss of LDL-uptake. The titration experiments which contain Fab and PCSK9 were done at a fixed concentration of PCSK9 (25 μg/ml) and increasing concentrations of Fab shown in the graphs. FIGS. 4A and 4C show calculations of IC-50s. 3BX5C01 exhibited a 25% inhibition of PCSK9-dependent inhibition of cellular LDL uptake, while 3CX2A06 exhibited 23% inhibition. FIGS. 5A-5B illustrate 3CX3D02's dose-dependent inhibition of PSCK9-dependent effects on LDL uptake. FIG. 5B has two controls: (i) a cell only control, showing the basal level of cellular LDL uptake, and (ii) a cell+PCSK9 (25 μg/ml) control which shows the level of PCSK9-dependent loss of LDL-uptake. The titration experiment which contains Fab and PCSK9 was done at a fixed concentration of PCSK9 (25 μg/ml) and increasing concentrations of Fab shown in the graphs. FIG. 5A shows calculations of IC-50. 3CX3D02 exhibited a 23% inhibition of PCSK9-dependent inhibition of cellular LDL uptake.

EXAMPLE 6

Kinetic Evaluation of FAB:PCSK9 Interactions with Surface Plasmon Resonance ("SPR")

SPR measurements were performed using a Biacore™ (Pharmacia Biosensor AB, Uppsala, Sweden) 2000 system. Sensor chip CM5 and Amine coupling kit for immobilization were from Biacore™.

Anti-Fab IgG (Human specific) was covalently coupled to surfaces 1 and 2 of a Sensor Chip CM5 via primary amine groups, using the immobilization wizard with the "Aim for immobilization" option. A target immobilization of 5000 RU was specified. The wizard uses a 7 minute activation with a 1:1 mixture of 100 mM NHS and 400 mM EDC; injects the ligand in several pulses to achieve the desired level, then deactivates the remaining surface with a 7 minute pulse of ethanolamine.

Anti-PCSK9 Fabs were captured on capture surface 2 and surface 1 was used as a reference for kinetic studies of Fab: PCSK9 interactions. Fab was captured by flowing a 500 ng/ml solution at 5 μl/min for 1-1.5 minutes to reach a target $R_L$ for an $R_{max}$ of 100-150 RU for the reaction. 5-10 concentrations of hPCSK9v5H is or mPCSK9v5H is antigens were flowed across the surface at 30 μl/minute for 3-4 minutes. 15-60 minutes dissociation time was allowed before regeneration of the Anti-Fab surface with a 30 second pulse of 10 mM glycine pH 2.0.

BiaEvaluation Software was used to evaluate the sensograms from the multiple concentration of PCSK9 antigen analyzed with each Fab, to estimate the kinetics constants of the Fab:PCSK9 interactions.

Table 3 illustrates kinetic parameters measured for disclosed anti-PCSK9 Fabs:

TABLE 3

| Fab | Ag | Method | $k_{on}$ (1/Ms × 10$^{-5}$) | $K_{off}$ (1/s × 10$^{4}$) | $K_D$ (nM) |
|---|---|---|---|---|---|
| 1CX1G08 | hPCSK9 | Direct & Ab Capture* | 3.35 ± 0.86 | 1.76 ± 0.13 | 0.55 ± 0.18 mean (N = 3) |
| 3BX5C01 | hPCSK9 | Direct* | 0.28 ± 0.00 | 6.42 ± 1.61 | 23.07 ± 5.6 mean (N = 2) |
| 3CX3D02 | hPCSK9 | Direct* | 1.66 ± 1.24 | 8.76 ± 1.02 | 7.01 ± 4.63 mean (N = 2) |
| 3CX4B08 | hPCSK9 | Direct & Ab Capture* | 2.33 ± 0.55 | 6.85 ± 3.13 | 2.97 ± 1.46 mean (N = 3) |

*"Direct" = covalent immobilization of PCSK9; bind Fab from mobile phase.
"Ab Capture" = covalent immobilization of anti-Fab Ab; capture of test Ab, then bind PCSK9 from mobile phase.

What is claimed is:

1. An isolated antibody or antigen-binding fragment thereof that specifically binds to PCSK9 and antagonizes PCSK9-mediated inhibition of cellular LDL uptake and comprises:
   (a) a heavy chain immunoglobulin variable region polypeptide comprising:
   a heavy chain CDR1 comprising the amino acid sequence set forth in SEQ ID NO: 81;
   a heavy chain CDR2 comprising the amino acid sequence set forth in SEQ ID NO: 83; and
   a heavy chain CDR3 comprising the amino acid sequence set forth in SEQ ID NO: 85; and
   (b) a light chain immunoglobulin variable region polypeptide comprising
   a light chain CDR1 comprising the amino acid sequence set forth in SEQ ID NO:71;
   a light chain CDR2 comprising the amino acid sequence set forth in SEQ ID NO: 73; and
   a light chain CDR3 comprising the amino acid sequence set forth in SEQ ID NO: 75.

2. The antibody or antigen-binding fragment thereof of claim 1 that binds to human PCSK9 with an equilibrium dissociation constant (KD) of less than 1200 nM.

3. The antibody or antigen-binding fragment thereof of claim 1 that binds to human PCSK9 with a KD of less than 500 nM.

4. The antibody or antigen-binding fragment thereof of claim 1 that binds to human PCSK9 with a KD of less than 100 nM.

5. The antibody or antigen-binding fragment thereof of claim 1 that binds to human PCSK9 with a KD of less than 5 nM.

6. The antibody or antigen-binding fragment thereof of claim 1 that antagonizes PCSK9's 25 inhibition of cellular LDL uptake at an IC50 of less than 500 nM.

7. The antibody or antigen-binding fragment thereof of claim 1 that antagonizes PCSK9's inhibition of cellular LDL uptake at an IC50 of less than 200 nM.

8. The antibody or antigen-binding fragment thereof of claim 1 that antagonizes PCSK9's inhibition of cellular LDL uptake at an IC50 of less than 100 nM.

9. The antibody or antigen-binding fragment thereof of claim 1 that antagonizes PCSK9's inhibition of cellular uptake by at least 20%.

10. An isolated antibody of claim 9 that is a monoclonal antibody.

11. The antibody or antigen-binding fragment thereof of claim 1 which comprises a heavy chain variable region comprising the amino acid sequence set forth in SEQ ID NO: 79 and a light chain variable region comprising the amino acid sequence set forth in SEQ ID NO: 69.

12. The antibody or antigen-binding fragment thereof of claim 9 which comprises a heavy chain comprising a constant sequence comprising the amino acid sequence set forth in SEQ ID NO: 87.

13. A composition comprising the antibody or antigen-binding fragment thereof of claim 1 and a pharmaceutically acceptable carrier.

14. A method for inhibiting cellular low density lipoprotein uptake in a human patient comprising administering, to the patient, a therapeutically effective amount of the antibody or antigen-binding fragment thereof of claim 1.

15. An isolated nucleic acid encoding
   (a) a heavy chain immunoglobulin variable region polypeptide comprising:
   a heavy chain CDR1 comprising the amino acid sequence set forth in SEQ ID NO: 81;
   a heavy chain CDR2 comprising the amino acid sequence set forth in SEQ ID NO: 83; and
   a heavy chain CDR3 comprising the amino acid sequence set forth in SEQ ID NO: 85; and
   (b) a light chain immunoglobulin variable region polypeptide comprising
   a light chain CDR1 comprising the amino acid sequence set forth in SEQ ID NO:71;
   a light chain CDR2 comprising the amino acid sequence set forth in SEQ ID NO: 73; and
   a light chain CDR3 comprising the amino acid sequence set forth in SEQ ID NO: 75.

16. The isolated nucleic acid of claim 15 comprising the nucleotide sequence set forth in SEQ ID NO: 80; and SEQ ID NO: 70.

17. A vector comprising the nucleic acid of claim 15.

18. An isolated host cell or population of host cells in vitro or in situ comprising the nucleic acid of claim 15.

19. A method for producing an antibody or antigen-binding fragment thereof which comprises:
   (a) culturing the cell(s) of claim 18 under conditions appropriate for production of the antibody; and
   (b) isolating the antibody produced.

20. An isolated host cell or population of host cells in vitro or in situ comprising the antibody of claim 1.

* * * * *

SEQUENCE LISTING

```
<160> NUMBER OF SEQ ID NOS: 102

<210> SEQ ID NO 1
<211> LENGTH: 213
<212> TYPE: PRT
<213> ORGANISM: Artificial Sequence
<220> FEATURE:
<223> OTHER INFORMATION: LC; 1CX1G08

<400> SEQUENCE: 1

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Ile Gly Thr Tyr Tyr Val
            20                  25                  30

His Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60
```

```
Asn Ser Gly Asn Thr Ala Thr Leu Thr Ile Ser Gly Thr Gln Ala Glu
 65                  70                  75                  80

Asp Glu Ala Asp Tyr Tyr Cys Gly Thr Trp Asp Asn Thr Ser Phe Asn
             85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
    210

<210> SEQ ID NO 2
<211> LENGTH: 639
<212> TYPE: DNA
<213> ORGANISM: Artificial Sequence
<220> FEATURE:
<223> OTHER INFORMATION: LC; 1CX1G08

<400> SEQUENCE: 2
gatatcgaac tgacccagcc gccttcagtg agcgttgcac aggtcagac cgcgcgtatc      60 tcgtgtagcg gcgataatat tggtacttat tatgttcatt ggtaccagca gaaacccggg    120
caggcgccag ttcttgtgat ttatgatgat tctaatcgtc cctcaggcat cccggaacgc    180
tttagcggat ccaacagcgg caacaccgcg accctgacca ttagcggcac tcaggcggaa    240
gacgaagcgg attattattg cggtacttgg gataatactt cttttaatct tgtgtttggc    300
ggcggcacga agttaaccgt tcttggccag ccgaaagccg caccgagtgt gacgctgttt    360
ccgccgagca gcgaagaatt gcaggcgaac aaagcgaccc tggtgtgcct gattagcgac    420
ttttatccgg gagccgtgac agtggcctgg aaggcagata gcagcccgt caaggcggga    480 gtggagacca ccacaccctc caaacaaagc aacaacaagt acgcggccag cagctatctg    540
agcctgacgc ctgagcagtg gaagtccac agaagctaca gctgccaggt cacgcatgag    600
gggagcaccg tggaaaaaac cgttgcgccg actgaggcc                          639

<210> SEQ ID NO 3
<211> LENGTH: 11
<212> TYPE: PRT
<213> ORGANISM: Artificial Sequence
<220> FEATURE:
<223> OTHER INFORMATION: VL CDR1; 1CX1G08

<400> SEQUENCE: 3

Ser Gly Asp Asn Ile Gly Thr Tyr Tyr Val His
  1               5                  10

<210> SEQ ID NO 4
<211> LENGTH: 33
<212> TYPE: DNA
```

<210> SEQ ID NO 4
<211> LENGTH: 33
<212> TYPE: DNA
<213> ORGANISM: Artificial Sequence
<220> FEATURE:
<223> OTHER INFORMATION: VL CDR1; 1CX1G08

<400> SEQUENCE: 4
agcggcgata atattggtac ttattatgtt cat                          33

<210> SEQ ID NO 5
<211> LENGTH: 7
<212> TYPE: PRT
<213> ORGANISM: Artificial Sequence
<220> FEATURE:
<223> OTHER INFORMATION: VL CDR2; 1CX1G08; 3BX5C01

<400> SEQUENCE: 5

Asp Asp Ser Asn Arg Pro Ser
 1               5

<210> SEQ ID NO 6
<211> LENGTH: 21
<212> TYPE: DNA
<213> ORGANISM: Artificial Sequence
<220> FEATURE:
<223> OTHER INFORMATION: VL CDR2; 1CX1G08; 3BX5C01

<400> SEQUENCE: 6
gatgattcta atcgtccctc a                                       21

<210> SEQ ID NO 7
<211> LENGTH: 11
<212> TYPE: PRT
<213> ORGANISM: Artificial Sequence
<220> FEATURE:
<223> OTHER INFORMATION: VL CDR3; 1CX1G08

<400> SEQUENCE: 7

Gly Thr Trp Asp Asn Thr Ser Phe Asn Leu Val
 1               5                  10

<210> SEQ ID NO 8
<211> LENGTH: 33
<212> TYPE: DNA
<213> ORGANISM: Artificial Sequence
<220> FEATURE:
<223> OTHER INFORMATION: VL CDR3; 1CX1G08

<400> SEQUENCE: 8
ggtacttggg ataatacttc ttttaatctt gtg                          33

<210> SEQ ID NO 9
<211> LENGTH: 241
<212> TYPE: PRT
<213> ORGANISM: Artificial Sequence
<220> FEATURE:
<223> OTHER INFORMATION: Fd Chain; 1CX1G08

<400> SEQUENCE: 9

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Trp Val Ser Trp Val Arg Gln Ala Pro Gly Lys Gly Leu Glu Trp Val
        35                  40                  45

Ser Phe Ile Ser Tyr Asp Gly Ser Ser Thr Tyr Tyr Ala Asp Ser Val
    50                  55                  60

```
                                    -continued
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Thr Tyr Phe Glu Gly Val Asp Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Glu Phe Glu Gln Lys
    210                 215                 220

Leu Ile Ser Glu Glu Asp Leu Asn Gly Ala Pro His His His His
225                 230                 235                 240

His

<210> SEQ ID NO 10
<211> LENGTH: 723
<212> TYPE: DNA
<213> ORGANISM: Artificial Sequence
<220> FEATURE:
<223> OTHER INFORMATION: Fd Chain; 1CX1G08

<400> SEQUENCE: 10
caggtgcaat tggtggaaag cggcggcggc ctggtgcaac cgggcggcag cctgcgtctg      60
agctgcgcgg cctccggatt taccttttct gattattggg tttcttgggt cgcgcaagcc     120
cctgggaagg gtctcgagtg ggtgagcttt atctcttatg atggtagctc taccattat     180 gcggatagcg tgaaaggccg ttttaccatt tcacgtgata ttcgaaaaaa cacccctgtat     240 ctgcaaatga acagcctgcg tgcggaagat acggccgtgt attattgcgc gcgtacttat     300
tttgagggtg ttgatgtttg gggccaaggc accctggtga cggttagctc agcgtcgacc     360
aaaggtccaa gcgtgtttcc gctggctccg agcagcaaaa gcaccagcgg cggcacggct     420
gccctgggct gcctggttaa agattatttc ccggaaccag tcaccgtgag ctggaacagc     480
ggggcgctga ccagcggcgt gcatactttt ccggcggtgc tgcaaagcag cggcctgtat     540
agcctgagca gcgttgtgac cgtgccgagc agcagcttag gcactcagac ctatatttgc     600
aacgtgaacc ataaaccgag caacaccaaa gtggataaaa agtggaaacc gaaaagcgaa     660
ttcgagcaga agctgatctc tgaggaggat ctgaacggcg cgccgcacca tcatcaccat     720
cac                                                                    723

<210> SEQ ID NO 11
<211> LENGTH: 117
<212> TYPE: PRT
<213> ORGANISM: Artificial Sequence
<220> FEATURE:
<223> OTHER INFORMATION: VH; 1CX1G08

<400> SEQUENCE: 11
```

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
             20                  25                  30

Trp Val Ser Trp Val Arg Gln Ala Pro Gly Lys Gly Leu Glu Trp Val
             35                  40                  45

Ser Phe Ile Ser Tyr Asp Gly Ser Ser Thr Tyr Tyr Ala Asp Ser Val
         50                  55                  60

Lys Gly Arg Phe Thr Ile Ser Arg Asp Asn Ser Lys Asn Thr Leu Tyr
 65              70                  75                  80

Leu Gln Met Asn Ser Leu Arg Ala Glu Asp Thr Ala Val Tyr Tyr Cys
                 85                  90                  95

Ala Arg Thr Tyr Phe Glu Gly Val Asp Val Trp Gly Gln Gly Thr Leu
            100                 105                 110

Val Thr Val Ser Ser
        115
```

<210> SEQ ID NO 12
<211> LENGTH: 351
<212> TYPE: DNA
<213> ORGANISM: Artificial Sequence
<220> FEATURE:
<223> OTHER INFORMATION: VH; 1CX1G08

<400> SEQUENCE: 12

```
caggtgcaat tggtggaaag cggcggcggc ctggtgcaac cgggcggcag cctgcgtctg      60
agctgcgcgg cctccggatt taccttttct gattattggg tttcttgggt cgcgccaagcc   120
cctgggaagg gtctcgagtg ggtgagcttt atctcttatg atggtagctc tacctattat   180
gcggatagcg tgaaaggccg ttttaccatt tcacgtgata attcgaaaaa caccctgtat   240
ctgcaaatga acagcctgcg tgcggaagat acggccgtgt attattgcgc gcgtacttat   300
tttgagggtg ttgatgtttg gggccaaggc accctggtga cggttagctc a            351
```

<210> SEQ ID NO 13
<211> LENGTH: 10
<212> TYPE: PRT
<213> ORGANISM: Artificial Sequence
<220> FEATURE:
<223> OTHER INFORMATION: VH CDR1; 1CX1G08

<400> SEQUENCE: 13

```
Gly Phe Thr Phe Ser Asp Tyr Trp Val Ser
  1               5                  10
```

<210> SEQ ID NO 14
<211> LENGTH: 30
<212> TYPE: DNA
<213> ORGANISM: Artificial Sequence
<220> FEATURE:
<223> OTHER INFORMATION: VH CDR1; 1CX1G08

<400> SEQUENCE: 14

```
ggatttacct tttctgatta ttgggtttct                                       30
```

<210> SEQ ID NO 15
<211> LENGTH: 17
<212> TYPE: PRT
<213> ORGANISM: Artificial Sequence
<220> FEATURE:
<223> OTHER INFORMATION: VH CDR2; 1CX1G08

```
<400> SEQUENCE: 15

Phe Ile Ser Tyr Asp Gly Ser Ser Thr Tyr Tyr Ala Asp Ser Val Lys
 1               5                  10                  15
Gly

<210> SEQ ID NO 16
<211> LENGTH: 51
<212> TYPE: DNA
<213> ORGANISM: Artificial Sequence
<220> FEATURE:
<223> OTHER INFORMATION: VH CDR2; 1CX1G08

<400> SEQUENCE: 16
tttatctctt atgatggtag ctctacctat tatgcggata gcgtgaaagg c            51

<210> SEQ ID NO 17
<211> LENGTH: 8
<212> TYPE: PRT
<213> ORGANISM: Artificial Sequence
<220> FEATURE:
<223> OTHER INFORMATION: VH CDR3; 1CX1G08

<400> SEQUENCE: 17

Thr Tyr Phe Glu Gly Val Asp Val
 1               5

<210> SEQ ID NO 18
<211> LENGTH: 24
<212> TYPE: DNA
<213> ORGANISM: Artificial Sequence
<220> FEATURE:
<223> OTHER INFORMATION: VH CDR3; 1CX1G08

<400> SEQUENCE: 18
acttattttg agggtgttga tgtt                                          24

<210> SEQ ID NO 19
<211> LENGTH: 212
<212> TYPE: PRT
<213> ORGANISM: Artificial Sequence
<220> FEATURE:
<223> OTHER INFORMATION: LC; 3BX5C01

<400> SEQUENCE: 19

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Arg Asp Tyr Ile Val
                20                  25                  30

His Trp Tyr Gln Gln Lys Pro Gly Gln Ala Pro Val Leu Val Ile Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
 65                 70                  75                  80

Asp Glu Ala Asp Tyr Tyr Cys Gly Phe Asp Asn Gly Gly Asp Ile Asp
                85                  90                  95

Val Phe Gly Gly Gly Thr Lys Leu Thr Val Leu Gly Gln Pro Lys Ala
                100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
        130                 135                 140
```

```
Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Ala
    210

<210> SEQ ID NO 20
<211> LENGTH: 636
<212> TYPE: DNA
<213> ORGANISM: Artificial Sequence
<220> FEATURE:
<223> OTHER INFORMATION: LC; 3BX5C01

<400> SEQUENCE: 20
gatatcgaac tgacccagcc gccttcagtg agcgttgcac caggtcagac cgcgcgtatc      60
tcgtgtagcg gcgataatct tcgtgattat attgttcatt ggtaccagca gaaacccggg     120
caggcgccag ttcttgtgat ttatgatgat tctaatcgtc cctcaggcat cccggaacgc     180
tttagcggat ccaacagcgg caacaccgcg accctgacca ttagcggcac tcaggcggaa     240
gacgaagcgg attattattg cggttttgat aatggtggtg atattgatgt gtttggcggc     300
ggcacgaagt taaccgttct tggccagccg aaagccgcac cgagtgtgac gctgtttccg     360
ccgagcagcg aagaattgca ggcgaacaaa gcgaccctgg tgtgcctgat tagcgacttt     420
tatccgggag ccgtgacagt ggcctggaag gcagatagca gccccgtcaa ggcgggagtg     480
gagaccacca cccctccaa acaaagcaac aacaagtacg cggccagcag ctatctgagc      540
ctgacgcctg agcagtggaa gtcccacaga agctacagct gccaggtcac gcatgagggg     600
agcaccgtgg aaaaaaccgt tgcgccgact gaggcc                               636

<210> SEQ ID NO 21
<211> LENGTH: 11
<212> TYPE: PRT
<213> ORGANISM: Artificial Sequence
<220> FEATURE:
<223> OTHER INFORMATION: VL CDR1; 3BX5C01

<400> SEQUENCE: 21

Ser Gly Asp Asn Leu Arg Asp Tyr Ile Val His
1               5                   10

<210> SEQ ID NO 22
<211> LENGTH: 33
<212> TYPE: DNA
<213> ORGANISM: Artificial Sequence
<220> FEATURE:
<223> OTHER INFORMATION: VL CDR1; 3BX5C01

<400> SEQUENCE: 22
agcggcgata atcttcgtga ttatattgtt cat                                    33

<210> SEQ ID NO 23
<211> LENGTH: 10
<212> TYPE: PRT
<213> ORGANISM: Artificial Sequence
<220> FEATURE:
<223> OTHER INFORMATION: VL CDR3; 3BX5C01
```

<400> SEQUENCE: 23

Gly Phe Asp Asn Gly Gly Asp Ile Asp Val
1               5                   10

<210> SEQ ID NO 24
<211> LENGTH: 30
<212> TYPE: DNA
<213> ORGANISM: Artificial Sequence
<220> FEATURE:
<223> OTHER INFORMATION: VL CDR3; 3BX5C01

<400> SEQUENCE: 24
ggttttgata atggtggtga tattgatgtg                                        30

<210> SEQ ID NO 25
<211> LENGTH: 246
<212> TYPE: PRT
<213> ORGANISM: Artificial Sequence
<220> FEATURE:
<223> OTHER INFORMATION: Fd Chain; 3BX5C01

<400> SEQUENCE: 25

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Gly Ile Ser Trp Val Arg Gln Met Pro Gly Lys Gly Leu Glu Trp Met
        35                  40                  45

Gly Met Ile Asp Pro Ser Asp Ser Phe Thr Thr Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Tyr Phe Thr Tyr Ala Leu Gln Pro Met Asp His Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Glu Phe Glu Gln Lys Leu Ile Ser Glu Glu Asp Leu Asn Gly Ala Pro
225                 230                 235                 240

His His His His His His
            245

<210> SEQ ID NO 26
<211> LENGTH: 738
<212> TYPE: DNA

<213> ORGANISM: Artificial Sequence
<220> FEATURE:
<223> OTHER INFORMATION: Fd Chain; 3BX5C01

<400> SEQUENCE: 26

```
caggtgcaat tggttcagag cggcgcggaa gtgaaaaaac cgggcgaaag cctgaaaatt      60
agctgcaaag gttccggata ttcctttact tcttatggta tttcttgggt gcgccagatg     120
cctgggaagg gtctcgagtg gatgggcatg atcgatccgt ctgatagctt taccacttat     180
tctccgagct ttcagggcca ggtgaccatt agcgcggata aaagcattag caccgcgtat     240
cttcaatgga gcagcctgaa agcgagcgat acggccatgt attattgcgc gcgtggttat     300
tattttactt atgctcttca gcctatggat cattggggcc aaggcaccct ggtgacggtt     360
agctcagcgt cgaccaaagg tccaagcgtg tttccgctgg ctccgagcag caaaagcacc     420
agcggcggca cggctgccct gggctgcctg gttaaagatt atttcccgga accagtcacc     480
gtgagctgga acagcggggc gctgaccagc ggcgtgcata cctttccggc ggtgctgcaa     540
agcagcggcc tgtatagcct gagcagcgtt gtgaccgtgc cgagcagcag cttaggcact     600
cagacctata tttgcaacgt gaaccataaa ccgagcaaca ccaaagtgga taaaaaagtg     660
gaaccgaaaa gcgaattcga gcagaagctg atctctgagg aggatctgaa cggcgcgccg     720
caccatcatc accatcac                                                   738
```

<210> SEQ ID NO 27
<211> LENGTH: 122
<212> TYPE: PRT
<213> ORGANISM: Artificial Sequence
<220> FEATURE:
<223> OTHER INFORMATION: VH; 3BX5C01

<400> SEQUENCE: 27

```
Gln Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Gly Ile Ser Trp Val Arg Gln Met Pro Gly Lys Gly Leu Glu Trp Met
         35                  40                  45

Gly Met Ile Asp Pro Ser Asp Ser Phe Thr Thr Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Tyr Tyr Phe Thr Tyr Ala Leu Gln Pro Met Asp His Trp
            100                 105                 110

Gly Gln Gly Thr Leu Val Thr Val Ser Ser
        115                 120
```

<210> SEQ ID NO 28
<211> LENGTH: 366
<212> TYPE: DNA
<213> ORGANISM: Artificial Sequence
<220> FEATURE:
<223> OTHER INFORMATION: VH; 3BX5C01

<400> SEQUENCE: 28

```
caggtgcaat tggttcagag cggcgcggaa gtgaaaaaac cgggcgaaag cctgaaaatt      60
agctgcaaag gttccggata ttcctttact tcttatggta tttcttgggt gcgccagatg     120
```

```
cctgggaagg gtctcgagtg gatgggcatg atcgatccgt ctgatagctt taccacttat      180
tctccgagct ttcagggcca ggtgaccatt agcgcggata aaagcattag caccgcgtat      240
cttcaatgga gcagcctgaa agcgagcgat acggccatgt attattgcgc gcgtggttat      300
tatttacttt atgctcttca gcctatggat cattggggcc aaggcaccct ggtgacggtt      360
agctca                                                                 366
```

<210> SEQ ID NO 29
<211> LENGTH: 10
<212> TYPE: PRT
<213> ORGANISM: Artificial Sequence
<220> FEATURE:
<223> OTHER INFORMATION: VH CDR1; 3BX5C01

<400> SEQUENCE: 29

Gly Tyr Ser Phe Thr Ser Tyr Gly Ile Ser
 1               5                  10

<210> SEQ ID NO 30
<211> LENGTH: 30
<212> TYPE: DNA
<213> ORGANISM: Artificial Sequence
<220> FEATURE:
<223> OTHER INFORMATION: VH CDR1; 3BX5C01

<400> SEQUENCE: 30

```
ggatattcct ttacttctta tggtatttct                                        30
```

<210> SEQ ID NO 31
<211> LENGTH: 17
<212> TYPE: PRT
<213> ORGANISM: Artificial Sequence
<220> FEATURE:
<223> OTHER INFORMATION: VH CDR2; 3BX5C01

<400> SEQUENCE: 31

Met Ile Asp Pro Ser Asp Ser Phe Thr Thr Tyr Ser Pro Ser Phe Gln
 1               5                  10                  15

Gly

<210> SEQ ID NO 32
<211> LENGTH: 51
<212> TYPE: DNA
<213> ORGANISM: Artificial Sequence
<220> FEATURE:
<223> OTHER INFORMATION: VH CDR2; 3BX5C01

<400> SEQUENCE: 32

```
atgatcgatc cgtctgatag ctttaccact tattctccga gctttcaggg c               51
```

<210> SEQ ID NO 33
<211> LENGTH: 13
<212> TYPE: PRT
<213> ORGANISM: Artificial Sequence
<220> FEATURE:
<223> OTHER INFORMATION: VH CDR3; 3BX5C01

<400> SEQUENCE: 33

Gly Tyr Tyr Phe Thr Tyr Ala Leu Gln Pro Met Asp His
 1               5                  10

<210> SEQ ID NO 34
<211> LENGTH: 39
<212> TYPE: DNA
<213> ORGANISM: Artificial Sequence

```
<220> FEATURE:
<223> OTHER INFORMATION: VH CDR3; 3BX5C01

<400> SEQUENCE: 34
ggttattatt ttacttatgc tcttcagcct atggatcat                              39

<210> SEQ ID NO 35
<211> LENGTH: 214
<212> TYPE: PRT
<213> ORGANISM: Artificial Sequence
<220> FEATURE:
<223> OTHER INFORMATION: VL; 3CX2A06

<400> SEQUENCE: 35
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Leu Gln Asn Tyr Asp Leu Pro Asn
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ala
    210

```
<210> SEQ ID NO 36
<211> LENGTH: 642
<212> TYPE: DNA
<213> ORGANISM: Artificial Sequence
<220> FEATURE:
<223> OTHER INFORMATION: LC; 3CX2A06

<400> SEQUENCE: 36
gatatccaga tgacccagag cccgtctagc ctgagcgcga gcgtgggtga tcgtgtgacc      60
attacctgca gcgcagccca gaatattaat tcttatctga attggtacca gcagaaacca     120
ggtaaagcac cgaaactatt aatttatgct gcttcttctt tgcaaagcgg ggtcccgtcc     180
cgttttagcg gctctggatc cggcactgat tttaccctga ccattagcag cctgcaacct     240
gaagactttg cggtttatta ttgccttcag aattatgatc ttcctaatac ctttggccag     300
ggtacgaaag ttgaaattaa acgtacggtg gctgctccga gcgtgtttat ttttccgccg     360
```

```
agcgatgaac aactgaaaag cggcacggcg agcgtggtgt gcctgctgaa caactttat      420 ccgcgtgaag cgaaagttca gtggaaagta gacaacgcgc tgcaaagcgg caacagccag      480
gaaagcgtga ccgaacagga tagcaaagat agcaccattt ctctgagcag caccctgacc      540
ctgagcaaag cggattatga aaaacataaa gtgtatgcgt gcgaagtgac ccatcaaggt      600
ctgagcagcc cggtgactaa atcttttaat cgtggcgagg cc                         642
```

```
<210> SEQ ID NO 37
<211> LENGTH: 11
<212> TYPE: PRT
<213> ORGANISM: Artificial Sequence
<220> FEATURE:
<223> OTHER INFORMATION: VL CDR1; 3CX2A06

<400> SEQUENCE: 37

Arg Ala Ser Gln Asn Ile Asn Ser Tyr Leu Asn
  1               5                  10
```

```
<210> SEQ ID NO 38
<211> LENGTH: 33
<212> TYPE: DNA
<213> ORGANISM: Artificial Sequence
<220> FEATURE:
<223> OTHER INFORMATION: VL CDR1; 3CX2A06

<400> SEQUENCE: 38
agagcgagcc agaatattaa ttcttatctg aat                                    33
```

```
<210> SEQ ID NO 39
<211> LENGTH: 7
<212> TYPE: PRT
<213> ORGANISM: Artificial Sequence
<220> FEATURE:
<223> OTHER INFORMATION: VL CDR2; 3CX2A06; 3CX3D02

<400> SEQUENCE: 39

Ala Ala Ser Ser Leu Gln Ser
  1               5
```

```
<210> SEQ ID NO 40
<211> LENGTH: 21
<212> TYPE: DNA
<213> ORGANISM: Artificial Sequence
<220> FEATURE:
<223> OTHER INFORMATION: VL CDR2; 3CX2A06; 3CX3D02

<400> SEQUENCE: 40
gctgcttctt ctttgcaaag c                                                 21
```

```
<210> SEQ ID NO 41
<211> LENGTH: 9
<212> TYPE: PRT
<213> ORGANISM: Artificial Sequence
<220> FEATURE:
<223> OTHER INFORMATION: VL CDR3; 3CX2A06

<400> SEQUENCE: 41

Leu Gln Asn Tyr Asp Leu Pro Asn Thr
  1               5
```

```
<210> SEQ ID NO 42
<211> LENGTH: 27
<212> TYPE: DNA
<213> ORGANISM: Artificial Sequence
<220> FEATURE:
```

<223> OTHER INFORMATION: VL CDR3; 3CX2A06

<400> SEQUENCE: 42
cttcagaatt atgatcttcc taatacc                                              27

<210> SEQ ID NO 43
<211> LENGTH: 241
<212> TYPE: PRT
<213> ORGANISM: Artificial Sequence
<220> FEATURE:
<223> OTHER INFORMATION: Fd Chain; 3CX2A06

<400> SEQUENCE: 43

```
Gln Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Ser Asn Phe
             20                  25                  30

Trp Ile Ala Trp Val Arg Gln Met Pro Gly Lys Gly Leu Glu Trp Met
         35                  40                  45

Gly Ile Ile Asp Pro Ser Asp Ser Trp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Asp Gly Gln Asp Phe Asp Asn Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Glu Phe Glu Gln Lys
    210                 215                 220

Leu Ile Ser Glu Glu Asp Leu Asn Gly Ala Pro His His His His
225                 230                 235                 240

His
```

<210> SEQ ID NO 44
<211> LENGTH: 723
<212> TYPE: DNA
<213> ORGANISM: Artificial Sequence
<220> FEATURE:
<223> OTHER INFORMATION: Fd Chain; 3CX2A06

<400> SEQUENCE: 44
caggtgcaat tggttcagag cggcgcggaa gtgaaaaaac cgggcgaaag cctgaaaatt      60
agctgcaaag gttccggata ttcctttct aattttggga ttgcttgggt gcgccagatg      120
cctgggaagg gtctcgagtg gatgggcatt atcgatccgt ctgatagctg gacccgttat    180
tctccgagct ttcagggcca ggtgaccatt agcgcggata aaagcattag caccgcgtat    240

```
cttcaatgga gcagcctgaa agcgagcgat acggccatgt attattgcgc gcgtggtgat    300
ggtcaggatt ttgataattg gggccaaggc accctggtga cggttagctc agcgtcgacc    360
aaaggtccaa gcgtgtttcc gctggctccg agcagcaaaa gcaccagcgg cggcacgggct   420 gccctgggct gcctggttaa agattatttc ccggaaccag tcaccgtgag ctggaacagc    480
ggggcgctga ccagcggcgt gcataccttt ccggcggtgc tgcaaagcag cggcctgtat    540
agcctgagca gcgttgtgac cgtgccgagc agcagcttag cactcagac ctatatttgc     600 aacgtgaacc ataaaccgag caacaccaaa gtggataaaa aagtggaacc gaaaagcgaa    660
ttcgagcaga agctgatctc tgaggaggat ctgaacggcg cgccgcacca tcatcaccat    720
cac                                                                  723
```

```
<210> SEQ ID NO 45
<211> LENGTH: 117
<212> TYPE: PRT
<213> ORGANISM: Artificial Sequence
<220> FEATURE:
<223> OTHER INFORMATION: VH; 3CX2A06

<400> SEQUENCE: 45

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Ser Asn Phe
             20                  25                  30

Trp Ile Ala Trp Val Arg Gln Met Pro Gly Lys Gly Leu Glu Trp Met
         35                  40                  45

Gly Ile Ile Asp Pro Ser Asp Ser Trp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Asp Gly Gln Asp Phe Asp Asn Trp Gly Gln Gly Thr Leu
            100                 105                 110

Val Thr Val Ser Ser
        115
```

```
<210> SEQ ID NO 46
<211> LENGTH: 351
<212> TYPE: DNA
<213> ORGANISM: Artificial Sequence
<220> FEATURE:
<223> OTHER INFORMATION: VH; 3CX2A06

<400> SEQUENCE: 46
caggtgcaat tggttcagag cggcgcggaa gtgaaaaaac cgggcgaaag cctgaaaatt     60
agctgcaaag gttccggata ttccttttct aattttttgga ttgcttgggt gcgccagatg   120
cctgggaagg gtctcgagtg gatgggcatt atcgatccgt ctgatagctg gacccgttat    180
tctccgagct tcagggcca ggtgaccatt agcgcggata aaagcattag cacggcgtat     240
cttcaatgga gcagcctgaa agcgagcgat acggccatgt attattgcgc gcgtggtgat    300
ggtcaggatt ttgataattg gggccaaggc accctggtga cggttagctc a             351
```

```
<210> SEQ ID NO 47
<211> LENGTH: 10
<212> TYPE: PRT
<213> ORGANISM: Artificial Sequence
```

```
<220> FEATURE:
<223> OTHER INFORMATION: VH CDR1; 3CX2A06

<400> SEQUENCE: 47

Gly Tyr Ser Phe Ser Asn Phe Trp Ile Ala
 1               5                  10

<210> SEQ ID NO 48
<211> LENGTH: 30
<212> TYPE: DNA
<213> ORGANISM: Artificial Sequence
<220> FEATURE:
<223> OTHER INFORMATION: VH CDR1; 3CX2A06

<400> SEQUENCE: 48
ggatattcct tttctaattt ttggattgct                                  30

<210> SEQ ID NO 49
<211> LENGTH: 17
<212> TYPE: PRT
<213> ORGANISM: Artificial Sequence
<220> FEATURE:
<223> OTHER INFORMATION: VH CDR2; 3CX2A06

<400> SEQUENCE: 49

Ile Ile Asp Pro Ser Asp Ser Trp Thr Arg Tyr Ser Pro Ser Phe Gln
 1               5                  10                  15

Gly

<210> SEQ ID NO 50
<211> LENGTH: 51
<212> TYPE: DNA
<213> ORGANISM: Artificial Sequence
<220> FEATURE:
<223> OTHER INFORMATION: VH CDR2; 3CX2A06

<400> SEQUENCE: 50
attatcgatc cgtctgatag ctggacccgt tattctccga gctttcaggg c           51

<210> SEQ ID NO 51
<211> LENGTH: 8
<212> TYPE: PRT
<213> ORGANISM: Artificial Sequence
<220> FEATURE:
<223> OTHER INFORMATION: VH CDR3; 3CX2A06

<400> SEQUENCE: 51

Gly Asp Gly Gln Asp Phe Asp Asn
 1               5

<210> SEQ ID NO 52
<211> LENGTH: 24
<212> TYPE: DNA
<213> ORGANISM: Artificial Sequence
<220> FEATURE:
<223> OTHER INFORMATION: VH CDR3; 3CX2A06

<400> SEQUENCE: 52
ggtgatggtc aggattttga taat                                        24

<210> SEQ ID NO 53
<211> LENGTH: 214
<212> TYPE: PRT
<213> ORGANISM: Artificial Sequence
<220> FEATURE:
<223> OTHER INFORMATION: LC; 3CX3D02
```

<400> SEQUENCE: 53

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Thr | Ile | Ser | Thr | Trp |
|---|---|---|---|---|---|---|---|---|---|---|---|---|---|---|---|
| | | | 20 | | | | | 25 | | | | | 30 | | |

| Leu | Asn | Trp | Tyr | Gln | Gln | Lys | Pro | Gly | Lys | Ala | Pro | Lys | Leu | Leu | Ile |
|---|---|---|---|---|---|---|---|---|---|---|---|---|---|---|---|
| | | 35 | | | | | 40 | | | | | 45 | | | |

| Tyr | Ala | Ala | Ser | Ser | Leu | Gln | Ser | Gly | Val | Pro | Ser | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Thr | Asp | Phe | Thr | Leu | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Glu | Asp | Phe | Ala | Thr | Tyr | Tyr | Cys | Leu | Gln | Asp | Ser | Ser | Leu | Pro | Leu |
|---|---|---|---|---|---|---|---|---|---|---|---|---|---|---|---|
| | | | | 85 | | | | | 90 | | | | | 95 | |

| Thr | Phe | Gly | Gln | Gly | Thr | Lys | Val | Glu | Ile | Lys | Arg | Thr | Val | Ala | Ala |
|---|---|---|---|---|---|---|---|---|---|---|---|---|---|---|---|
| | | | 100 | | | | | 105 | | | | | 110 | | |

| Pro | Ser | Val | Phe | Ile | Phe | Pro | Pro | Ser | Asp | Glu | Gln | Leu | Lys | Ser | Gly |
|---|---|---|---|---|---|---|---|---|---|---|---|---|---|---|---|
| | | 115 | | | | | 120 | | | | | 125 | | | |

| Thr | Ala | Ser | Val | Val | Cys | Leu | Leu | Asn | Asn | Phe | Tyr | Pro | Arg | Glu | Ala |
|---|---|---|---|---|---|---|---|---|---|---|---|---|---|---|---|
| | 130 | | | | | 135 | | | | | 140 | | | | |

| Lys | Val | Gln | Trp | Lys | Val | Asp | Asn | Ala | Leu | Gln | Ser | Gly | Asn | Ser | Gln |
|---|---|---|---|---|---|---|---|---|---|---|---|---|---|---|---|
| 145 | | | | | 150 | | | | | 155 | | | | | 160 |

| Glu | Ser | Val | Thr | Glu | Gln | Asp | Ser | Lys | Asp | Ser | Thr | Tyr | Ser | Leu | Ser |
|---|---|---|---|---|---|---|---|---|---|---|---|---|---|---|---|
| | | | | 165 | | | | | 170 | | | | | 175 | |

| Ser | Thr | Leu | Thr | Leu | Ser | Lys | Ala | Asp | Tyr | Glu | Lys | His | Lys | Val | Tyr |
|---|---|---|---|---|---|---|---|---|---|---|---|---|---|---|---|
| | | | 180 | | | | | 185 | | | | | 190 | | |

| Ala | Cys | Glu | Val | Thr | His | Gln | Gly | Leu | Ser | Ser | Pro | Val | Thr | Lys | Ser |
|---|---|---|---|---|---|---|---|---|---|---|---|---|---|---|---|
| | | 195 | | | | | 200 | | | | | 205 | | | |

| Phe | Asn | Arg | Gly | Glu | Ala |
|---|---|---|---|---|---|
| | | 210 | | | |

<210> SEQ ID NO 54
<211> LENGTH: 642
<212> TYPE: DNA
<213> ORGANISM: Artificial Sequence
<220> FEATURE:
<223> OTHER INFORMATION: LC; 3CX3D02

<400> SEQUENCE: 54

```
gatatccaga tgacccagag cccgtctagc ctgagcgcga gcgtgggtga tcgtgtgacc      60
attacctgca gcgagcca gactatttct acttggctga attggtacca gcagaaacca      120
ggtaaagcac cgaaactatt aatttatgct gcttcttctt tgcaaagcgg ggtcccgtcc     180
cgttttagcg gctctggatc cggcactgat tttaccctga ccattagcag cctgcaacct     240
gaagactttg cgacttatta ttgccttcag gattcttctc ttcctcttac ctttggccag     300
ggtacgaaag ttgaaattaa acgtacggtg gctgctccga gcgtgttat ttttccgccg      360
agcgatgaac aactgaaaag cggcacggcg agcgtggtgt gcctgctgaa caacttttat     420
ccgcgtgaag cgaaagttca gtggaaagta gacaacgcgc tgcaaagcgg caacagccag     480
gaaagcgtga ccgaacagga tagcaaagat agcacctatt ctctgagcag cacccctgacc    540
ctgagcaaag cggattatga aaaacataaa gtgtatgcgt gcgaagtgac ccatcaaggt     600
ctgagcagcc cggtgactaa atcttttaat cgtggcgagg cc                        642
```

<210> SEQ ID NO 55
<211> LENGTH: 11
<212> TYPE: PRT

```
<213> ORGANISM: Artificial Sequence
<220> FEATURE:
<223> OTHER INFORMATION: VL CDR1; 3CX3D02

<400> SEQUENCE: 55

Arg Ala Ser Gln Thr Ile Ser Thr Trp Leu Asn
 1               5                  10

<210> SEQ ID NO 56
<211> LENGTH: 33
<212> TYPE: DNA
<213> ORGANISM: Artificial Sequence
<220> FEATURE:
<223> OTHER INFORMATION: VL CDR1; 3CX3D02

<400> SEQUENCE: 56
agagcgagcc agactatttc tacttggctg aat                          33

<210> SEQ ID NO 57
<211> LENGTH: 9
<212> TYPE: PRT
<213> ORGANISM: Artificial Sequence
<220> FEATURE:
<223> OTHER INFORMATION: VL CDR3; 3CX3D02

<400> SEQUENCE: 57

Leu Gln Asp Ser Ser Leu Pro Leu Thr
 1               5

<210> SEQ ID NO 58
<211> LENGTH: 27
<212> TYPE: DNA
<213> ORGANISM: Artificial Sequence
<220> FEATURE:
<223> OTHER INFORMATION: VL CDR3; 3CX3D02

<400> SEQUENCE: 58
cttcaggatt cttctcttcc tcttacc                                 27

<210> SEQ ID NO 59
<211> LENGTH: 244
<212> TYPE: PRT
<213> ORGANISM: Artificial Sequence
<220> FEATURE:
<223> OTHER INFORMATION: Fd Chain; 3CX3D02

<400> SEQUENCE: 59

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Ser
                20                  25                  30

Trp Ile Gly Trp Val Arg Gln Met Pro Gly Lys Gly Leu Glu Trp Met
            35                  40                  45

Gly Ile Ile Tyr Pro Ser Asp Ser Tyr Thr Ile Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Gly Tyr Tyr Ala Leu Met Asp Val Trp Ala Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Glu Phe
    210                 215                 220

Glu Gln Lys Leu Ile Ser Glu Glu Asp Leu Asn Gly Ala Pro His His
225                 230                 235                 240

His His His His
```

<210> SEQ ID NO 60
<211> LENGTH: 732
<212> TYPE: DNA
<213> ORGANISM: Artificial Sequence
<220> FEATURE:
<223> OTHER INFORMATION: Fd Chain; 3CX3D02

<400> SEQUENCE: 60

```
caggtgcaat tggttcagag cggcgcggaa gtgaaaaaac cgggcgaaag cctgaaaatt      60
agctgcaaag gttccggata ttcctttact aattcttgga ttggttgggt cgcgccagatg    120
cctgggaagg gtctcgagtg gatgggcatt atctatccgt ctgatagcta taccatttat    180
tctccgagct ttcagggcca ggtgaccatt agcgcggata aaagcattag caccgcgtat    240
cttcaatgga gcagcctgaa agcgagcgat acggccatgt attattgcgc gcgtggtggt    300
ggttattatt atgctcttat ggatgtttgg gcccaaggca ccctggtgac ggttagctca    360
gcgtcgacca aggtccaag cgtgtttccg ctggctccga gcagcaaaag caccagcggc     420
ggcacggctg ccctgggctg cctggttaaa gattatttcc cggaaccagt caccgtgagc    480
tggaacagcg gggcgctgac cagcggcgtg catacctttc cggcggtgct gcaaagcagc    540
ggcctgtata gcctgagcag cgttgtgacc gtgccgagca gcagcttagg cactcagacc    600
tatatttgca acgtgaacca taaaccgagc aacaccaaag tggataaaaa agtggaaccg    660
aaaagcgaat cgagcagaa gctgatctct gaggaggatc tgaacggcgc gccgcaccat    720
catcaccatc ac                                                        732
```

<210> SEQ ID NO 61
<211> LENGTH: 120
<212> TYPE: PRT
<213> ORGANISM: Artificial Sequence
<220> FEATURE:
<223> OTHER INFORMATION: VH; 3CX3D02

<400> SEQUENCE: 61

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Ser
            20                  25                  30

Trp Ile Gly Trp Val Arg Gln Met Pro Gly Lys Gly Leu Glu Trp Met
        35                  40                  45

Gly Ile Ile Tyr Pro Ser Asp Ser Tyr Thr Ile Tyr Ser Pro Ser Phe
    50                  55                  60
```

```
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Gly Gly Tyr Tyr Tyr Ala Leu Met Asp Val Trp Ala Gln
            100                 105                 110

Gly Thr Leu Val Thr Val Ser Ser
        115                 120

<210> SEQ ID NO 62
<211> LENGTH: 360
<212> TYPE: DNA
<213> ORGANISM: Artificial Sequence
<220> FEATURE:
<223> OTHER INFORMATION: VH; 3CX3D02

<400> SEQUENCE: 62
caggtgcaat tggttcagag cggcgcggaa gtgaaaaaac cgggcgaaag cctgaaaatt       60
agctgcaaag gttccggata ttcctttact aattcttgga ttggttgggt gcgccagatg     120
cctgggaagg gtctcgagtg gatgggcatt atctatccgt ctgatagcta taccatttat     180
tctccgagct ttcagggcca ggtgaccatt agcgcggata aaagcattag caccgcgtat     240
cttcaatgga gcagcctgaa agcgagcgat acggccatgt attattgcgc gcgtggtggt     300
ggttattatt atgctcttat ggatgtttgg gcccaaggca ccctggtgac ggttagctca     360

<210> SEQ ID NO 63
<211> LENGTH: 10
<212> TYPE: PRT
<213> ORGANISM: Artificial Sequence
<220> FEATURE:
<223> OTHER INFORMATION: VH CDR1; 3CX3D02

<400> SEQUENCE: 63

Gly Tyr Ser Phe Thr Asn Ser Trp Ile Gly
  1               5                  10

<210> SEQ ID NO 64
<211> LENGTH: 30
<212> TYPE: DNA
<213> ORGANISM: Artificial Sequence
<220> FEATURE:
<223> OTHER INFORMATION: VH CDR1; 3CX3D02

<400> SEQUENCE: 64
ggatattcct ttactaattc ttggattggt                                       30

<210> SEQ ID NO 65
<211> LENGTH: 16
<212> TYPE: PRT
<213> ORGANISM: Artificial Sequence
<220> FEATURE:
<223> OTHER INFORMATION: VH CDR2; 3CX3D02

<400> SEQUENCE: 65

Ile Ile Tyr Pro Ser Asp Ser Tyr Thr Ile Tyr Ser Pro Ser Phe Gln
  1               5                  10                  15

<210> SEQ ID NO 66
<211> LENGTH: 48
<212> TYPE: DNA
<213> ORGANISM: Artificial Sequence
<220> FEATURE:
<223> OTHER INFORMATION: VH CDR2; 3CX3D02
```

-continued

<400> SEQUENCE: 66
attatctatc cgtctgatag ctataccatt tattctccga gctttcag                48

<210> SEQ ID NO 67
<211> LENGTH: 11
<212> TYPE: PRT
<213> ORGANISM: Artificial Sequence
<220> FEATURE:
<223> OTHER INFORMATION: VH CDR3; 3CX3D02

<400> SEQUENCE: 67

Gly Gly Gly Tyr Tyr Tyr Ala Leu Met Asp Val
1               5                   10

<210> SEQ ID NO 68
<211> LENGTH: 33
<212> TYPE: DNA
<213> ORGANISM: Artificial Sequence
<220> FEATURE:
<223> OTHER INFORMATION: VH CDR3; 3CX3D02

<400> SEQUENCE: 68
ggtggtggtt attattatgc tcttatggat gtt                               33

<210> SEQ ID NO 69
<211> LENGTH: 212
<212> TYPE: PRT
<213> ORGANISM: Artificial Sequence
<220> FEATURE:
<223> OTHER INFORMATION: LC; 3CX4B08

<400> SEQUENCE: 69

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Pro Thr Tyr Tyr Val
            20                  25                  30

Ala Trp Tyr Gln Gln Lys Pro Gly Gln Ala Pro Val Leu Val Ile Tyr
        35                  40                  45

Ser Asp Thr Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Phe Asp Asn His Gly Tyr His
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Ala

<210> SEQ ID NO 70
<211> LENGTH: 636
<212> TYPE: DNA
<213> ORGANISM: Artificial Sequence
<220> FEATURE:
<223> OTHER INFORMATION: LC; 3CX4B08

<400> SEQUENCE: 70

```
gatatcgaac tgacccagcc gccttcagtg agcgttgcac caggtcagac cgcgcgtatc    60
tcgtgtagcg gcgattctat tcctacttat tatgttgctt ggtaccagca gaaacccggg   120
caggcgccag ttcttgtgat ttattctgat actgatcgtc cctcaggcat cccggaacgc   180
tttagcggat ccaacagcgg caacaccgcg accctgacca ttagcggcac tcaggcggaa   240
gacgaagcgg attattattg ccagtctttt gataatcatg ttatcatgt gtttggcgga    300
ggcacgaagt taaccgttct tggccagccg aaagccgcac cgagtgtgac gctgtttccg   360
ccgagcagcg aagaattgca ggcgaacaaa gcgaccctgg tgtgcctgat tagcgacttt   420
tatccgggag ccgtgacagt ggcctggaag gcagatagca gcccgtcaa ggcgggagtg    480
gagaccacca caccctccaa acaaagcaac aacaagtacg cggccagcag ctatctgagc   540
ctgacgcctg agcagtggaa gtcccacaga agctacagct gccaggtcac gcatgagggg   600
agcaccgtgg aaaaaaccgt tgcgccgact gaggcc                             636
```

<210> SEQ ID NO 71
<211> LENGTH: 11
<212> TYPE: PRT
<213> ORGANISM: Artificial Sequence
<220> FEATURE:
<223> OTHER INFORMATION: VL CDR1; 3CX4B08

<400> SEQUENCE: 71

Ser Gly Asp Ser Ile Pro Thr Tyr Tyr Val Ala
 1               5                   10

<210> SEQ ID NO 72
<211> LENGTH: 33
<212> TYPE: DNA
<213> ORGANISM: Artificial Sequence
<220> FEATURE:
<223> OTHER INFORMATION: VL CDR1; 3CX4B08

<400> SEQUENCE: 72

```
agcggcgatt ctattcctac ttattatgtt gct                                 33
```

<210> SEQ ID NO 73
<211> LENGTH: 7
<212> TYPE: PRT
<213> ORGANISM: Artificial Sequence
<220> FEATURE:
<223> OTHER INFORMATION: VL CDR2; 3CX4B08

<400> SEQUENCE: 73

Ser Asp Thr Asp Arg Pro Ser
 1               5

<210> SEQ ID NO 74
<211> LENGTH: 21
<212> TYPE: DNA
<213> ORGANISM: Artificial Sequence
<220> FEATURE:
<223> OTHER INFORMATION: VL CDR2; 3CX4B08

-continued

```
<400> SEQUENCE: 74
tctgatactg atcgtccctc a                                              21

<210> SEQ ID NO 75
<211> LENGTH: 10
<212> TYPE: PRT
<213> ORGANISM: Artificial Sequence
<220> FEATURE:
<223> OTHER INFORMATION: VL CDR3; 3CX4B08

<400> SEQUENCE: 75

Gln Ser Phe Asp Asn His Gly Tyr His Val
 1               5                  10

<210> SEQ ID NO 76
<211> LENGTH: 30
<212> TYPE: DNA
<213> ORGANISM: Artificial Sequence
<220> FEATURE:
<223> OTHER INFORMATION: VL CDR3; 3CX4B08

<400> SEQUENCE: 76
cagtcttttg ataatcatgg ttatcatgtg                                     30

<210> SEQ ID NO 77
<211> LENGTH: 241
<212> TYPE: PRT
<213> ORGANISM: Artificial Sequence
<220> FEATURE:
<223> OTHER INFORMATION: Fd Chain; 3CX4B08

<400> SEQUENCE: 77

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Thr Met Asn Trp Val Arg Gln Ala Pro Gly Lys Gly Leu Glu Trp Val
         35                  40                  45

Ser Phe Ile Ser Ser Ser Ser Glu Thr Tyr Tyr Ala Asp Ser Val
     50                  55                  60

Lys Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
                 85                  90                  95

Ala Arg Gly Tyr Gly Asp Met Val Asp Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Glu Phe Glu Gln Lys
    210                 215                 220
```

Leu Ile Ser Glu Glu Asp Leu Asn Gly Ala Pro His His His His
225                 230                 235                 240

His

<210> SEQ ID NO 78
<211> LENGTH: 723
<212> TYPE: DNA
<213> ORGANISM: Artificial Sequence
<220> FEATURE:
<223> OTHER INFORMATION: Fd Chain; 3CX4B08

<400> SEQUENCE: 78
caggtgcaat tggtggaaag cggcggcggc ctggtgcaac cgggcggcag cctgcgtctg      60
agctgcgcgg cctccggatt tacctttttct aattatacta tgaattgggt gcgccaagcc    120
cctgggaagg gtctcgagtg ggtgagcttt atctcttctt cttctagcga gacctattat    180
gcggatagcg tgaaaggccg ttttaccatt tcacgtgata attcgaaaaa cacccctgtat   240
ctgcaaatga acagcctgcg tgcggaagat acggccgtgt attattgcgc gcgtggttat    300
ggtgatatgg ttgatctttg gggccaaggc accctggtga cggttagctc agcgtcgacc   360
aaaggtccaa gcgtgtttcc gctggctccg agcagcaaaa gcaccagcgg cggcacggct   420
gccctgggct gcctggttaa agattatttc ccggaaccag tcaccgtgag ctggaacagc   480
ggggcgctga ccagcggcgt gcataccttt ccggcggtgc tgcaaagcag cggcctgtat   540
agcctgagca gcgttgtgac cgtgccgagc agcagcttag gcactcagac ctatatttgc   600
aacgtgaacc ataaaccgag caacaccaaa gtggataaaa aagtggaacc gaaaagcgaa   660
ttcgagcaga agctgatctc tgaggaggat ctgaacggcg cgccgcacca tcatcaccat   720
cac                                                                  723

<210> SEQ ID NO 79
<211> LENGTH: 117
<212> TYPE: PRT
<213> ORGANISM: Artificial Sequence
<220> FEATURE:
<223> OTHER INFORMATION: VH; 3CX4B08

<400> SEQUENCE: 79

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Thr Met Asn Trp Val Arg Gln Ala Pro Gly Lys Gly Leu Glu Trp Val
        35                  40                  45

Ser Phe Ile Ser Ser Ser Ser Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Gly Asp Met Val Asp Leu Trp Gly Gln Gly Thr Leu
            100                 105                 110

Val Thr Val Ser Ser
        115

<210> SEQ ID NO 80
<211> LENGTH: 351
<212> TYPE: DNA

<213> ORGANISM: Artificial Sequence
<220> FEATURE:
<223> OTHER INFORMATION: VH; 3CX4B08

<400> SEQUENCE: 80

```
caggtgcaat tggtggaaag cggcggcggc ctggtgcaac cgggcggcag cctgcgtctg      60
agctgcgcgg cctccggatt tacctttcct aattatacta tgaattgggt gcgccaagcc     120
cctgggaagg gtctcgagtg ggtgagcttt atctcttctt cttctagcga gacctattat     180
gcggatagcg tgaaaggccg ttttaccatt tcacgtgata attcgaaaaa caccctgtat     240
ctgcaaatga acagcctgcg tgcggaagat acggccgtgt attattgcgc gcgtggttat     300
ggtgatatgg ttgatctttg gggccaaggc accctggtga cggttagctc a              351
```

<210> SEQ ID NO 81
<211> LENGTH: 10
<212> TYPE: PRT
<213> ORGANISM: Artificial Sequence
<220> FEATURE:
<223> OTHER INFORMATION: VH CDR1; 3CX4B08

<400> SEQUENCE: 81

Gly Phe Thr Phe Ser Asn Tyr Thr Met Asn
 1               5                  10

<210> SEQ ID NO 82
<211> LENGTH: 30
<212> TYPE: DNA
<213> ORGANISM: Artificial Sequence
<220> FEATURE:
<223> OTHER INFORMATION: VH CDR1; 3CX4B08

<400> SEQUENCE: 82

```
ggatttacct ttctaatta tactatgaat                                        30
```

<210> SEQ ID NO 83
<211> LENGTH: 17
<212> TYPE: PRT
<213> ORGANISM: Artificial Sequence
<220> FEATURE:
<223> OTHER INFORMATION: VH CDR2; 3CX4B08

<400> SEQUENCE: 83

Phe Ile Ser Ser Ser Ser Ser Glu Thr Tyr Tyr Ala Asp Ser Val Lys
 1               5                  10                  15
Gly

<210> SEQ ID NO 84
<211> LENGTH: 51
<212> TYPE: DNA
<213> ORGANISM: Artificial Sequence
<220> FEATURE:
<223> OTHER INFORMATION: VH CDR2; 3CX4B08

<400> SEQUENCE: 84

```
tttatctctt cttcttctag cgagacctat tatgcggata gcgtgaaagg c               51
```

<210> SEQ ID NO 85
<211> LENGTH: 8
<212> TYPE: PRT
<213> ORGANISM: Artificial Sequence
<220> FEATURE:
<223> OTHER INFORMATION: VH CDR3; 3CX4B08

<400> SEQUENCE: 85

Gly Tyr Gly Asp Met Val Asp Leu
1               5

<210> SEQ ID NO 86
<211> LENGTH: 24
<212> TYPE: DNA
<213> ORGANISM: Artificial Sequence
<220> FEATURE:
<223> OTHER INFORMATION: VH CDR3; 3CX4B08

<400> SEQUENCE: 86
ggttatggtg atatggttga tctt                                            24

<210> SEQ ID NO 87
<211> LENGTH: 326
<212> TYPE: PRT
<213> ORGANISM: Artificial Sequence
<220> FEATURE:
<223> OTHER INFORMATION: Fc domain of IgG2m4

<400> SEQUENCE: 87

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys

```
                    290                 295                 300
Ser Val Met His Glu Ala Leu His Asn His Tyr Thr Gln Lys Ser Leu
305                 310                 315                 320

Ser Leu Ser Pro Gly Lys
                325

<210> SEQ ID NO 88
<211> LENGTH: 978
<212> TYPE: DNA
<213> ORGANISM: Artificial Sequence
<220> FEATURE:
<223> OTHER INFORMATION: constant of IgG2m4

<400> SEQUENCE: 88
gcctccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgacctcca gcaactttgg cacgcagacc     240
tacacctgca acgtagatca caagcccagc aacaccaagg tggacaagac agttgagcgg     300
aaatgctgcg tggagtgccc accatgccca gcacctccag tggccggacc atcagtcttc     360
ctgttccccc caaaacccaa ggacactctc atgatctccc ggaccoctga ggtcacgtgc     420 gtggtggtgg acgtgagcca ggaagacccc gaggtccagt tcaactggta cgtggatggc     480
gtggaggtgc ataatgccaa gacaaagccg cgggaggagc agttcaacag cacgttccgt     540
gtggtcagcg tcctcaccgt cctgcaccag gactggctga acggcaagga gtacaagtgc     600
aaggtctcca acaaaggcct cccgtcctcc atcgagaaaa ccatctccaa aaccaaaggg     660
cagccccgag agccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacgc tcccatgct ggactccgac     840 ggctccttct cctctacag caagctaacc gtggacaaga gcaggtggca gcagggaat     900 gtcttctcat gctccgtgat gcatgaggct ctgcacaacc actacacaca gaagagcctc     960
tccctgtctc ctggtaaa                                                   978

<210> SEQ ID NO 89
<211> LENGTH: 330
<212> TYPE: PRT
<213> ORGANISM: Artificial Sequence
<220> FEATURE:
<223> OTHER INFORMATION: contains Fc domain of IgG1

<400> SEQUENCE: 89

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95
```

-continued

```
Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 90
<211> LENGTH: 326
<212> TYPE: PRT
<213> ORGANISM: Artificial Sequence
<220> FEATURE:
<223> OTHER INFORMATION: contains Fc domain of IgG2

<400> SEQUENCE: 90

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
```

-continued

```
            130                 135                 140
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 91
<211> LENGTH: 327
<212> TYPE: PRT
<213> ORGANISM: Artificial Sequence
<220> FEATURE:
<223> OTHER INFORMATION: contains Fc domain of IgG4

<400> SEQUENCE: 91

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 92
<211> LENGTH: 326
<212> TYPE: PRT
<213> ORGANISM: Artificial Sequence
<220> FEATURE:
<223> OTHER INFORMATION: contains Fc domain of IgG2m4

<400> SEQUENCE: 92

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 93
<211> LENGTH: 109
<212> TYPE: PRT
<213> ORGANISM: Artificial Sequence
<220> FEATURE:
<223> OTHER INFORMATION: VL; 1CX1G08

<400> SEQUENCE: 93

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Thr Tyr Tyr Val
            20                  25                  30

His Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Thr Trp Asp Asn Thr Ser Phe Asn
                85                  90                  95

Leu Val Phe Gly Gly Gly Thr Lys Leu Thr Val Leu Gly
            100                 105

<210> SEQ ID NO 94
<211> LENGTH: 327
<212> TYPE: DNA
<213> ORGANISM: Artificial Sequence
<220> FEATURE:
<223> OTHER INFORMATION: VL; 1CX1G08

<400> SEQUENCE: 94
gatatcgaac tgacccagcc gccttcagtg agcgttgcac caggtcagac cgcgcgtatc      60
tcgtgtagcg gcgataatat tggtacttat tatgttcatt ggtaccagca gaaacccggg     120
caggcgccag ttcttgtgat ttatgatgat tctaatcgtc cctcaggcat cccggaacgc     180
tttagcggat ccaacagcgg caacaccgcg accctgacca ttagcggcac tcaggcggaa     240
gacgaagcgg attattattg cggtacttgg gataatactt cttttaatct tgtgtttggc     300
ggcggcacga agttaaccgt tcttggc                                         327

<210> SEQ ID NO 95
<211> LENGTH: 107

<212> TYPE: PRT
<213> ORGANISM: Artificial Sequence
<220> FEATURE:
<223> OTHER INFORMATION: VL; 3BX5C01

<400> SEQUENCE: 95

Ile Glu Leu Thr Gln Pro Pro Ser Val Ser Val Ala Pro Gly Gln Thr
1               5                   10                  15

Ala Arg Ile Ser Cys Ser Gly Asp Asn Leu Arg Asp Tyr Ile Val His
            20                  25                  30

Trp Tyr Gln Gln Lys Pro Gly Gln Ala Pro Val Leu Val Ile Tyr Asp
        35                  40                  45

Asp Ser Asn Arg Pro Ser Gly Ile Pro Glu Arg Phe Ser Gly Ser Asn
    50                  55                  60

Ser Gly Asn Thr Ala Thr Leu Thr Ile Ser Gly Thr Gln Ala Glu Asp
65                  70                  75                  80

Glu Ala Asp Tyr Tyr Cys Gly Phe Asp Asn Gly Gly Asp Ile Asp Val
                85                  90                  95

Phe Gly Gly Gly Thr Lys Leu Thr Val Leu Gly
            100                 105

<210> SEQ ID NO 96
<211> LENGTH: 324
<212> TYPE: DNA
<213> ORGANISM: Artificial Sequence
<220> FEATURE:
<223> OTHER INFORMATION: VL; 3BX5C01

<400> SEQUENCE: 96
gatatcgaac tgacccagcc gccttcagtg agcgttgcac caggtcagac cgcgcgtatc      60
tcgtgtagcg gcgataatct tcgtgattat attgttcatt ggtaccagca gaaacccggg     120
caggcgccag ttcttgtgat ttatgatgat tctaatcgtc cctcaggcat cccggaacgc     180
tttagcggat ccaacagcgg caacaccgcg accctgacca ttagcggcac tcaggcggaa     240
gacgaagcgg attattattg cggttttgat aatggtggtg atattgatgt gtttggcggc     300
ggcacgaagt taaccgttct tggc                                            324

<210> SEQ ID NO 97
<211> LENGTH: 108
<212> TYPE: PRT
<213> ORGANISM: Artificial Sequence
<220> FEATURE:
<223> OTHER INFORMATION: VL; 3CX2A06

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Thr Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Ser Ser Leu Pro Leu
                85                  90                  95

Thr Phe Gly Gln Gly Thr Lys Val Glu Ile Lys Arg
            100                 105

<210> SEQ ID NO 98
<211> LENGTH: 324
<212> TYPE: DNA
<213> ORGANISM: Artificial Sequence
<220> FEATURE:
<223> OTHER INFORMATION: VL; 3CX2A06

<400> SEQUENCE: 98

```
gatatccaga tgacccagag cccgtctagc ctgagcgcga gcgtgggtga tcgtgtgacc      60
attacctgca gagcgagcca gaatattaat tcttatctga attggtacca gcagaaacca     120
ggtaaagcac cgaaactatt aatttatgct gcttcttctt tgcaaagcgg ggtcccgtcc     180
cgttttagcg gctctggatc cggcactgat tttaccctga ccattagcag cctgcaacct     240
gaagactttg cggtttatta ttgccttcag aattatgatc ttcctaatac ctttggccag     300
ggtacgaaag ttgaaattaa acgt                                            324
```

<210> SEQ ID NO 99
<211> LENGTH: 108
<212> TYPE: PRT
<213> ORGANISM: Artificial Sequence
<220> FEATURE:
<223> OTHER INFORMATION: VL; 3CX3D02

<400> SEQUENCE: 99

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Thr Ile Ser Thr Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Ser Ser Leu Pro Leu
                85                  90                  95

Thr Phe Gly Gln Gly Thr Lys Val Glu Ile Lys Arg
               100                 105
```

<210> SEQ ID NO 100
<211> LENGTH: 324
<212> TYPE: DNA
<213> ORGANISM: Artificial Sequence
<220> FEATURE:
<223> OTHER INFORMATION: VL; 3CX3D02

<400> SEQUENCE: 100

```
gatatccaga tgacccagag cccgtctagc ctgagcgcga gcgtgggtga tcgtgtgacc      60
attacctgca gagcgagcca gactatttct acttggctga attggtacca gcagaaacca     120
ggtaaagcac cgaaactatt aatttatgct gcttcttctt tgcaaagcgg ggtcccgtcc     180
cgttttagcg gctctggatc cggcactgat tttaccctga ccattagcag cctgcaacct     240
gaagactttg cgacttatta ttgccttcag gattcttctc ttcctcttac ctttggccag     300
ggtacgaaag ttgaaattaa acgt                                            324
```

<210> SEQ ID NO 101
<211> LENGTH: 108
<212> TYPE: PRT

```
<213> ORGANISM: Artificial Sequence
<220> FEATURE:
<223> OTHER INFORMATION: VL; 3CX4B08

<400> SEQUENCE: 101

Asp Ile Glu Leu Thr Gln Pro Pro Ser Val Ser Val Ala Pro Gly Gln
 1               5                  10                  15

Thr Ala Arg Ile Ser Cys Ser Gly Asp Ser Ile Pro Thr Tyr Tyr Val
            20                  25                  30

Ala Trp Tyr Gln Gln Lys Pro Gly Gln Ala Pro Val Leu Val Ile Tyr
        35                  40                  45

Ser Asp Thr Asp Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Phe Asp Asn His Gly Tyr His
                85                  90                  95

Val Phe Gly Gly Gly Thr Lys Leu Thr Val Leu Gly
            100                 105

<210> SEQ ID NO 102
<211> LENGTH: 324
<212> TYPE: DNA
<213> ORGANISM: Artificial Sequence
<220> FEATURE:
<223> OTHER INFORMATION: VL; 3CX4B08

<400> SEQUENCE: 102
gatatcgaac tgacccagcc gccttcagtg agcgttgcac caggtcagac cgcgcgtatc      60
tcgtgtagcg gcgattctat tcctacttat tatgttgctt ggtaccagca gaaacccggg     120
caggcgccag ttcttgtgat ttattctgat actgatcgtc cctcaggcat cccggaacgc     180
tttagcggat ccaacagcgg caacaccgcg accctgacca ttagcggcac tcaggcggaa     240
gacgaagcgg attattattg ccagtctttt gataatcatg gttatcatgt gtttggcgga     300
ggcacgaagt taaccgttct tggc                                            324
```